(12) United States Patent
Gonczol et al.

(10) Patent No.: US 6,448,389 B1
(45) Date of Patent: Sep. 10, 2002

(54) HUMAN CYTOMEGALOVIRUS DNA CONSTRUCTS AND USES THEREFOR

(75) Inventors: Eva Gonczol; Klara Berencsi; Csaba Kari, all of Rosemont, PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 0 days.

(21) Appl. No.: 09/171,699

(22) PCT Filed: Apr. 22, 1997

(86) PCT No.: PCT/US97/06866

§ 371 (c)(1),
(2), (4) Date: Jan. 19, 1999

(87) PCT Pub. No.: WO97/40165

PCT Pub. Date: Oct. 30, 1997

Related U.S. Application Data

(60) Provisional application No. 60/015,717, filed on Apr. 23, 1996.

(51) Int. Cl.[7] ............................................... C07H 21/04
(52) U.S. Cl. ................ 536/23.72; 435/69.1; 435/320.1; 424/230.1
(58) Field of Search ....................... 536/23.72; 435/69.1, 435/320.1; 424/230.1

(56) References Cited

U.S. PATENT DOCUMENTS

| | | |
|---|---|---|
| 3,959,466 A | 5/1976 | Plotkin |
| 4,689,225 A | 8/1987 | Pereira |
| 4,920,209 A | 4/1990 | Davis |
| 5,124,440 A | 6/1992 | Gehrz |
| 5,552,143 A | 9/1996 | Plotkin |
| 5,591,439 A | 1/1997 | Plotkin |

FOREIGN PATENT DOCUMENTS

| | | |
|---|---|---|
| EP | 180288 | 5/1986 |
| EP | 236145 | 9/1987 |
| EP | 252302 | 1/1988 |
| EP | 252531 | 1/1988 |
| EP | 268014 | 5/1988 |
| EP | 271201 | 6/1988 |
| EP | 277773 | 8/1988 |
| EP | 389286 | 9/1990 |
| EP | 609580 | 8/1994 |
| WO | WO89/07143 | 8/1989 |
| WO | WO90/00062 | 1/1990 |
| WO | WO90/01497 | 2/1990 |
| WO | WO90/06771 | 6/1990 |
| WO | WO90/11302 | 10/1990 |
| WO | WO91/02004 | 2/1991 |
| WO | WO91/18088 | 11/1991 |
| WO | WO92/00323 | 1/1992 |
| WO | WO92/02628 | 2/1992 |
| WO | WO93/19191 | 9/1993 |
| WO | WO94/17810 | 8/1994 |
| WO | WO94/23744 | 10/1994 |
| WO | WO96/01321 | 1/1996 |
| WO | WO97/40165 | 10/1997 |

OTHER PUBLICATIONS

Plachter, B., et al., 1990, "Procaryotic expression of phosphorylated tegument protein pp65 of human cytomegalovirus and application of recombinant peptides for immunoblot analyses", J. Clin. Microbiol. 28(6):1229–1235.*

Pande, H., et al., 1991, "Human cytomegalovirus strain Towne pp65 gene: nucleotide sequence and expression in *Escherichia coli*", Virol. 182:220–228.*

Pande, H., et al., 1995, "Direct DNA immunization of mice with plasmid DNA encoding the tegument protein pp65 (ppUL83) of human cytomegalovirus induces high levels of circulating antibody to the encoded protein", Scandanav. J. Infect. Dis. 99:117–20.*

Hayashi, I., et al., 1993, "A point mutation of alanine 163 to threonine is responsible for the defective secretion of high molecular weight kininogen by the liver or brown Norway Katholiek rats", J. Biol. Chem. 268(23):17219–17224.*

Baier, G., et al., 1994, "An efficient expression, purification, and immunodetection system for recombinant gene products", Bio Tech. 17(1):94, 96, 98, and 99.*

Ulmer, J. B., et al., 1994, "Protective immunity by intramuscular injection of low doses of influenza virus DNA vaccines", Vaccine 12(16):1541–1544.*

Invitrogen catalog, 1994, p. 51.*

M. Cranage et al, "Identification of the Human Cytomegalovirus Glycoprotein B Gene and Induction of Neutralizing Antibodies via its Expression in Recombinant Vaccinia Virus", *EMBO J.*, 5(11):3057–3063 (Nov., 1986).

K. Berencsi et al, "Murine Cytotoxic T Cell Response Specific for Human Cytomegalovirus Glycoprotein B (gB) Induced by Adenovirus and Vaccinia Virus Recombinants Expressing gB", *J. Gen. Virol.*, 74(11):2507–2512 (Nov., 1993) [Berencsi I].

S. Plotkin et al, "Towne–Vaccine–Induced Prevention of Cytomegalovirus Disease After Renal Transplants", *Lancet*, 1:528–530 (Mar. 10, 1984) [Plotkin I].

S. Plotkin et al, "Prevention of Cytomegalovirus Disease by Towne Strain Live Attenuated Vaccine", *Birth Defects: Original Article Series*, 20(1):271–287 (1984) [Plotkin II].

S. Plotkin et al, "Clinical Trials of Immunization with the Towne 125 Strain of Human Cytomegalovirus", *J. Infect. Dis.*, 134(5):470–475 (Nov., 1976) [Plotkin III].

(List continued on next page.)

*Primary Examiner*—Laurie Scheiner
*Assistant Examiner*—Jeffrey S. Parkin
(74) *Attorney, Agent, or Firm*—Howson and Howson

(57) ABSTRACT

Novel DNA molecules for in vitro and in vivo expression of HCMV gB, gB transmembrane deleted derivatives, pp65, pp150, and IE-exon-4 proteins are described. Preferably, the molecules are plasmids. Also described are methods of using these DNA molecules to induce immune responses to HCMV, and the use of a plasmid of the invention to prime immune responses to HCMV vaccines.

3 Claims, 27 Drawing Sheets

OTHER PUBLICATIONS

J. Glazer et al, "Live Cytomegalovirus Vaccination of Renal Transplant Candidates", *Annals of Internal Medicine*, 91:676–683 (Nov., 1979).

E. Gonczol et al, "Preclinical Evaluation of an ALVAC (canarypox)–Human Cytomegalovirus Glycoprotein B Vaccine Candidate", *Vaccine*, 13(12):1080–1085 (1995) [Gonczol I].

K. Berencsi et al, "The N–terminal 303 Amino Acids of the Human Cytomegalovirus Envelope Glycoprotein B (UL55) and the Exon 4 Region of the Major Immediate Early Protein 1 (UL123) Induce a Cytotoxic T–Cell Response", *Vaccine*, 14(5):369–374 (Apr., 1996) [Berencsi II].

E. Gonczol et al, "Preclinical Evaluation of an ALVAC (canarypox)–Human Cytomegalovirus Glycoprotein B Vaccine Candidate; Immune Response Elicited in a Prime/Boost Protocol with the Glycoprotein B Subunit", *Scand. J. Infect. Dis., Suppl.* 99:110–112 (1995) [Gonczol II].

J. Dhawan et al, "Tetracycline–Regulated Gene Expression Following Direct Gene Transfer into Mouse Skeletal Muscle", *Somatic Cell and Molecular Genetics*, 21(4):233–240 (1995).

K. Berencsi et al, "Murine Cytotoxic T Cell Response Specific for Human Cytomegalovirus Glycoprotein B (gB) Induced by Adenovirus and Vaccinia Virus Recombinants Expressing gB", *J. Gen. Virol.*, 74:2507–2512 (1993) [Berencsi III].

H. Pande et al, "Human Cytomegalovirus Strain Towne pp65 Gene: Nucleotide Sequence and Expression in *Escherichia coli*", *Virology*, 182:220–228 (1991) [Pande I].

M. Gossen et al, "Tight Control of Gene Expression in Mammalian Cells by Tetracycline–Responsive Promoters", *Proc. Natl. Acad. Sci. USA*, 89:5547–5551 (Jun., 1992).

J. Hanshaw, "Congenital Cytomegalovirus Infection: A Fifteen Year Perspective", *J. Infect. Dis.*, 123(5):555–561 (May, 1971).

D. Johnson et al, "Abundant Expression of Herpes Simplex Virus Glycoprotein gB Using an Adenovirus Vector", *Virology*, 164:1–14 (1988).

R. Dewar et al, "Synthesis and Processing of Human Immunodeficiency Virus Type 1 Envelope Proteins Encoded by a Recombinant Human Adenovirus", *J. Virol.*, 63(1):129–136 (Jan., 1989).

A. Davis et al, "Expression of Hepatitis B Surface Antigen with a Recombinant Adenovirus", *Proc. Natl. Acad. Sci. USA*, 82:7560–7564 (Nov., 1985).

J. Morin et al, "Recombinant Adenovirus Induces Antibody Response to Hepatitis B Virus Surface Antigen in Hamsters", *Proc. Natl. Acad. Sci. USA*, 84:4626–4630 (Jul., 1987).

R. Couch et al, "Immunization with Types 4 and 7 Adenovirus by Selective Infection of the Intestinal Tract", *Am. Rev. Respir. Dis.*, 88:394–403 (1963).

E. Takafuji et al, "Simultaneous Administration of Live, Enteric–Coated Adenovirus Types 4, 7, and 21 Vaccines: Safety and Immunogenicity", *J. Infect. Dis.*, 140(1):48–53 (Jul., 1979).

P. Collis et al, "Adenovirus Vaccines in Military Recruit Populations: A Cost–Benefit Analysis", *J. Infect. Dis.*, 128(6):745–752 (Dec., 1973).

R. Stenberg et al, "Structural Analysis of the Major Immediate Early Gene of Human Cytomegalovirus", *J. Virol.*, 49(1):190–199 (Jan., 1984).

N. Alp et al, "Fine Specificity of Cellular Immune Responses in Humans to Human Cytomegalovirus Immediate–Early 1 Protein", *J. Virol.*, 65(9):4812–4820 (Sep., 1991).

H. Volkmer et al, "Cytolytic T Lymphocyte Recognition of the Murine Cytomegalovirus Nonstructural Immediate–Early Protein PP89 Expressed by Recombinant Vaccinia Virus", *J. Exp. Med.*, 166(3):668–688 (Sep., 1987) (Abstract only).

R. Lerner et al, "The Development of Synthetic Vaccines", in *The Biology of Immunologic Disease*, Chapter 31, pp. 331–338 (Spring, 1983).

GenBank Data Entry, Access #M11630, Code #HS5MIE4 (Sep. 15, 1989).

G. Marshall et al, "An Adenovirus Recombinant that Expresses the Human Cytomegalovirus Major Envelope Glycoprotein and Induces Neutralizing Antibodies", *J. Infect. Dis.*, 162:1177–1181 (Nov. 1990).

Y-N. Liu et al, "The N–Terminal 513 Amino Acids of the Envelope Glycoprotein gB of Human Cytomegalovirus Stimulates Both B– and T–Cell Immune Responses in Humans", *J. Virol.*, 65(3):1644–1648 (Mar., 1991).

K. Berencsi et al, "Human Cytomegalovirus (HCMV) Glycoprotein–B (gB)–Specific Cell–Mediated Immunity in Experimental Animals", *Acta Microbiologica Hungarica*, 38(3–4):170–171 (1991) [Berencsi IV].

E. Gonczol et al, "DNA Immunization Induces Human Cytomegalovirus (HCMV)–Glycoprotein B (gB)–Specific Neutralizing Antibody as Well as Phosphoprotein 65 (pp65)–Specific Cytotoxic T Lymphocyte Responses and Primes Immune Responses to HCMV Proteins", 6$^{th}$ International Cytomegalovirus Workshop, Orange Beach, Alabama (Mar. 5–9, 1997) (Abstract only) [Gonczol III].

G. Jahn et al, "Map Position and Nucleotide Sequence of the Gene for the Large Structural Phosphoprotein of Human Cytomegalovirus", *J. Virol.*, 61(5):1358–1367 (1987) (Abstract only) [Jahn I].

G. Jahn et al, "The Two Major Structural Phosproteins pp65 and pp150 of Human Cytomegalovirus and Their Antigenic Properties", *J. Gen. Virol.*, 68(5):1327–1338 (1987) (Abstract only) [Jahn II].

H. Pande et al, "Direct DNA Immunization of Mice with Plasmid DNA Encoding the Tegument Protein pp65 (ppUL83) of Human Cytomegalovirus Induces High Levels of Circulating Antibody to the Encoded Protein", *Scand. J. Infect. Dis., Suppl.* 99:117–120 (1995) [Pande II].

R. Giannella et al, "Invasion of HeLa Cells by *Salmonella typhinurium*: a Model for Study of Invasiveness of Salmonella", *J. Infect. Dis.*, 128(1):69–75 (Jul., 1973).

\* cited by examiner

FIGURE 3A

| | | | | | | | | | | | | | | | |
|---|---|---|---|---|---|---|---|---|---|---|---|---|---|---|---|
| ATG | GAA | TCC | AGG | ATC | TGG | TGC | CTG | GTA | GTC | TGC | GTT | AAC | TTG | TGT | 45 |
| Met | Glu | Ser | Arg | Ile | Trp | Cys | Leu | Val | Val | Cys | Val | Asn | Leu | Cys | |
| 1 | | | | 5 | | | | | 10 | | | | | 15 | |

```
ATG GAA TCC AGG ATC TGG TGC CTG GTA GTC TGC GTT AAC TTG TGT       45
Met Glu Ser Arg Ile Trp Cys Leu Val Val Cys Val Asn Leu Cys
  1           5                  10                   15

ATC GTC TGT CTG GGT GCT GCG GTT TCC TCA TCT TCT ACT CGT GGA       90
Ile Val Cys Leu Gly Ala Ala Val Ser Ser Ser Ser Thr Arg Gly
                 20                  25                  30

ACT TCT GCT ACT CAC AGT CAC CAT TCC TCT CAT ACG ACG TCT GCT      135
Thr Ser Ala Thr His Ser His His Ser Ser His Thr Thr Ser Ala
                 35                  40                  45

GCT CAT TCT CGA TCC GGT TCA GTC TCT CAA CGC GTA ACT TCT TCC      180
Ala His Ser Arg Ser Gly Ser Val Ser Gln Arg Val Thr Ser Ser
                 50                  55                  60

CAA ACG GTC AGC CAT GGT GTT AAC GAG ACC ATC TAC AAC ACT ACC      225
Gln Thr Val Ser His Gly Val Asn Glu Thr Ile Tyr Asn Thr Thr
                 65                  70                  75

CTC AAG TAC GGA GAT GTG GTG GGG GTC AAC ACC ACC AAG TAC CCC      270
Leu Lys Tyr Gly Asp Val Val Gly Val Asn Thr Thr Lys Tyr Pro
                 80                  85                  90

TAT CGC GTG TGT TCT ATG GCA CAG GGT ACG GAT CTT ATT CGC TTT      315
Tyr Arg Val Cys Ser Met Ala Gln Gly Thr Asp Leu Ile Arg Phe
                 95                 100                 105

GAA CGT AAT ATC GTC TGC ACC TCG ATG AAG CCC ATC AAT GAA GAC      360
Glu Arg Asn Ile Val Cys Thr Ser Met Lys Pro Ile Asn Glu Asp
                110                 115                 120

CTG GAC GAG GGC ATC ATG GTG GTC TAC AAA CGC AAC ATC GTC GCG      405
Leu Asp Glu Gly Ile Met Val Val Tyr Lys Arg Asn Ile Val Ala
                125                 130                 135

CAC ACC TTT AAG GTA CGA GTC TAC CAG AAG GTT TTG ACG TTT CGT      450
His Thr Phe Lys Val Arg Val Tyr Gln Lys Val Leu Thr Phe Arg
                140                 145                 150

CGT AGC TAC GCT TAC ATC CAC ACC ACT TAT CTG CTG GGC AGC AAC      495
Arg Ser Tyr Ala Tyr Ile His Thr Thr Tyr Leu Leu Gly Ser Asn
                155                 160                 165

ACG GAA TAC GTG GCG CCT CCT ATG TGG GAG ATT CAT CAT ATC AAC      540
Thr Glu Tyr Val Ala Pro Pro Met Trp Glu Ile His His Ile Asn
                170                 175                 180

AGT CAC AGT CAG TGC TAC AGT TCC TAC AGC CGC GTT ATA GCA GGC      585
Ser His Ser Gln Cys Tyr Ser Ser Tyr Ser Arg Val Ile Ala Gly
                185                 190                 195

ACG GTT TTC GTG GCT TAT CAT AGG GAC AGC TAT GAA AAC AAA ACC      630
Thr Val Phe Val Ala Tyr His Arg Asp Ser Tyr Glu Asn Lys Thr
                200                 205                 210
```

FIGURE 3B

```
ATG CAA TTA ATG CCC GAC GAT TAT TCC AAC ACC CAC AGT ACC CGT    675
Met Gln Leu Met Pro Asp Asp Tyr Ser Asn Thr His Ser Thr Arg
            215                 220                 225

TAC GTG ACG GTC AAG GAT CAA TGG CAC AGC CGC GGC AGC ACC TGG    720
Tyr Val Thr Val Lys Asp Gln Trp His Ser Arg Gly Ser Thr Trp
            230                 235                 240

CTC TAT CGT GAG ACC TGT AAT CTG AAT TGT ATG GTG ACC ATC ACT    765
Leu Tyr Arg Glu Thr Cys Asn Leu Asn Cys Met Val Thr Ile Thr
            245                 250                 255

ACT GCG CGC TCC AAG TAT CCC TAT CAT TTT TTC GCA ACT TCC ACG    810
Thr Ala Arg Ser Lys Tyr Pro Tyr His Phe Phe Ala Thr Ser Thr
            260                 265                 270

GGT GAT GTG GTT GAC ATT TCT CCT TTC TAC AAC GGA ACT AAT CGC    855
Gly Asp Val Val Asp Ile Ser Pro Phe Tyr Asn Gly Thr Asn Arg
            275                 280                 285

AAT GCC AGC TAT TTT GGA GAA AAC GCC GAC AAG TTT TTC ATT TTT    900
Asn Ala Ser Tyr Phe Gly Glu Asn Ala Asp Lys Phe Phe Ile Phe
            290                 295                 300

CCG AAC TAC ACT ATC GTC TCC GAC TTT GGA AGA CCG AAT TCT GCG    945
Pro Asn Tyr Thr Ile Val Ser Asp Phe Gly Arg Pro Asn Ser Ala
            305                 310                 315

TTA GAG ACC CAC AGG TTG GTG GCT TTT CTT GAA CGT GCG GAC TCA    990
Leu Glu Thr His Arg Leu Val Ala Phe Leu Glu Arg Ala Asp Ser
            320                 325                 330

GTG ATC TCC TGG GAT ATA CAG GAC GAG AAG AAT GTT ACT TGT CAA   1035
Val Ile Ser Trp Asp Ile Gln Asp Glu Lys Asn Val Thr Cys Gln
            335                 340                 345

CTC ACT TTC TGG GAA GCC TCG GAA CGC ACC ATT CGT TCC GAA GCC   1080
Leu Thr Phe Trp Glu Ala Ser Glu Arg Thr Ile Arg Ser Glu Ala
            350                 355                 360

GAG GAC TCG TAT CAC TTT TCT TCT GCC AAA ATG ACC GCC ACT TTC   1125
Glu Asp Ser Tyr His Phe Ser Ser Ala Lys Met Thr Ala Thr Phe
            365                 370                 375

TTA TCT AAG AAG CAA GAG GTG AAC ATG TCC GAC TCT GCG CTG GAC   1170
Leu Ser Lys Lys Gln Glu Val Asn Met Ser Asp Ser Ala Leu Asp
            380                 385                 390

TGT GTA CGT GAT GAG GCC ATA AAT AAG TTA CAG CAG ATT TTC AAT   1215
Cys Val Arg Asp Glu Ala Ile Asn Lys Leu Gln Gln Ile Phe Asn
            395                 400                 405

ACT TCA TAC AAT CAA ACA TAT GAA AAA TAT GGA AAC GTG TCC GTC   1260
Thr Ser Tyr Asn Gln Thr Tyr Glu Lys Tyr Gly Asn Val Ser Val
            410                 415                 420
```

FIGURE 3C

| | | | | | | | | | | | | | |
|---|---|---|---|---|---|---|---|---|---|---|---|---|---|
| TTT | GAA | ACC | ACT | GGT | GGT | TTG | GTG | GTG | TTC | TGG | CAA | GGT | ATC | AAG | 1305
| Phe | Glu | Thr | Thr | Gly | Gly | Leu | Val | Val | Phe | Trp | Gln | Gly | Ile | Lys |
| | | | 425 | | | | 430 | | | | | | 435 |

```
TTT GAA ACC ACT GGT GGT TTG GTG GTG TTC TGG CAA GGT ATC AAG     1305
Phe Glu Thr Thr Gly Gly Leu Val Val Phe Trp Gln Gly Ile Lys
             425             430                         435

CAA AAA TCT CTG GTG GAA CTC GAA CGT TTG GCC AAC CGC TCC AGT     1350
Gln Lys Ser Leu Val Glu Leu Glu Arg Leu Ala Asn Arg Ser Ser
             440             445                         450

CTG AAT CTT ACT CAT AAT AGA ACC AAA AGA AGT ACA GAT GGC AAC     1395
Leu Asn Leu Thr His Asn Arg Thr Lys Arg Ser Thr Asp Gly Asn
             455             460                         465

AAT GCA ACT CAT TTA TCC AAC ATG GAG TCG GTG CAC AAT CTG GTC     1440
Asn Ala Thr His Leu Ser Asn Met Glu Ser Val His Asn Leu Val
             470             475                         480

TAC GCC CAG CTG CAG TTC ACC TAT GAC ACG TTG CGC GGT TAC ATC     1485
Tyr Ala Gln Leu Gln Phe Thr Tyr Asp Thr Leu Arg Gly Tyr Ile
             485             490                         495

AAC CGG GCG CTG GCG CAA ATC GCA GAA GCC TGG TGT GTG GAT CAA     1530
Asn Arg Ala Leu Ala Gln Ile Ala Glu Ala Trp Cys Val Asp Gln
             500             505                         510

CGG CGC ACC CTA GAG GTC TTC AAG GAA CTT AGC AAG ATC AAC CCG     1575
Arg Arg Thr Leu Glu Val Phe Lys Glu Leu Ser Lys Ile Asn Pro
             515             520                         525

TCA GCT ATT CTC TCG GCC ATC TAC AAC AAA CCG ATT GCC GCG CGT     1620
Ser Ala Ile Leu Ser Ala Ile Tyr Asn Lys Pro Ile Ala Ala Arg
             530             535                         540

TTC ATG GGT GAT GTC CTG GGT CTG GCC AGC TGC GTG ACC ATT AAC     1665
Phe Met Gly Asp Val Leu Gly Leu Ala Ser Cys Val Thr Ile Asn
             545             550                         555

CAA ACC AGC GTC AAG GTG CTG CGT GAT ATG AAT GTG AAG GAA TCG     1710
Gln Thr Ser Val Lys Val Leu Arg Asp Met Asn Val Lys Glu Ser
             560             565                         570

CCA GGA CGC TGC TAC TCA CGA CCA GTG GTC ATC TTT AAT TTC GCC     1755
Pro Gly Arg Cys Tyr Ser Arg Pro Val Val Ile Phe Asn Phe Ala
             575             580                         585

AAC AGC TCG TAC GTG CAG TAC GGT CAA CTG GGC GAG GAT AAC GAA     1800
Asn Ser Ser Tyr Val Gln Tyr Gly Gln Leu Gly Glu Asp Asn Glu
             590             595                         600

ATC CTG TTG GGC AAC CAC CGC ACT GAG GAA TGT CAG CTT CCC AGC     1845
Ile Leu Leu Gly Asn His Arg Thr Glu Glu Cys Gln Leu Pro Ser
             605             610                         615

CTC AAG ATC TTC ATC GCC GGC AAC TCG GCC TAC GAG TAC GTG GAC     1890
Leu Lys Ile Phe Ile Ala Gly Asn Ser Ala Tyr Glu Tyr Val Asp
             620             625                         630
```

FIGURE 3D

```
TAC CTC TTC AAA CGC ATG ATT GAC CTC AGC AGC ATC TCC ACC GTC    1935
Tyr Leu Phe Lys Arg Met Ile Asp Leu Ser Ser Ile Ser Thr Val
            635             640             645

GAC AGC ATG ATC GCC CTA GAC ATC GAC CCG CTG GAA AAC ACC GAC    1980
Asp Ser Met Ile Ala Leu Asp Ile Asp Pro Leu Glu Asn Thr Asp
            650             655             660

TTC AGG GTA CTG GAA CTT TAC TCG CAG AAA GAA TTG CGT TCC AGC    2025
Phe Arg Val Leu Glu Leu Tyr Ser Gln Lys Glu Leu Arg Ser Ser
            665             670             675

AAC GTT TTT GAT CTC GAG GAG ATC ATG CGC GAG TTC AAT TCG TAT    2070
Asn Val Phe Asp Leu Glu Glu Ile Met Arg Glu Phe Asn Ser Tyr
            680             685             690

AAG CAG CGG GTA AAG TAC GTG GAG GAC AAG GTA GTC GAC CCG CTG    2115
Lys Gln Arg Val Lys Tyr Val Glu Asp Lys Val Val Asp Pro Leu
            695             700             705

CCG CCC TAC CTC AAG GGT CTG GAC GAC CTC ATG AGC GGC CTG GGC    2160
Pro Pro Tyr Leu Lys Gly Leu Asp Asp Leu Met Ser Gly Leu Gly
            710             715             720

GCC GCG GGA AAG GCC GTT GGC GTA GCC ATT GGG GCC GTG GGT GGC    2205
Ala Ala Gly Lys Ala Val Gly Val Ala Ile Gly Ala Val Gly Gly
            725             730             735

GCG GTG GCC TCC GTG GTC GAA GGC GTT GCC ACC TTC CTC AAA AAC    2250
Ala Val Ala Ser Val Val Glu Gly Val Ala Thr Phe Leu Lys Asn
            740             745             750

CCC TTC GGA GCC TTC ACC ATC ATC CTC GTG GCC ATA GCC GTC GTC    2295
Pro Phe Gly Ala Phe Thr Ile Ile Leu Val Ala Ile Ala Val Val
            755             760             765

ATT ATC ATT TAT TTG ATC TAT ACT CGA CAG CGG CGT CTC TGC ATG    2340
Tyr Leu Ile Tyr Thr Arg Gln Arg Arg Leu Cys Met Gln Pro Leu
            770             775             780

CAG CCG CTG CAG AAC CTC TTT CCC TAT CTG GTG TCC GCC GAC GGG    2385
Ile Ile Ile Gln Asn Leu Phe Pro Tyr Leu Val Ser Ala Asp Gly
            785             790             795

ACC ACC GTG ACG TCG GGC AAC ACC AAA GAC ACG TCG TTA CAG GCT    2430
Thr Thr Val Thr Ser Gly Asn Thr Lys Asp Thr Ser Leu Gln Ala
            800             805             810

CCG CCT TCC TAC GAG GAA AGT GTT TAT AAT TCT GGT CGC AAA GGA    2475
Pro Pro Ser Tyr Glu Glu Ser Val Tyr Asn Ser Gly Arg Lys Gly
            815             820             825

CCG GGA CCA CCG TCG TCT GAT GCA TCC ACG GCG GCT CCG CCT TAC    2520
Pro Gly Pro Pro Ser Ser Asp Ala Ser Thr Ala Ala Pro Pro Tyr
            830             835             840
```

FIGURE 3E

```
ACC AAC GAG CAG GCT TAC CAG ATG CTT CTG GCC CTG GTC CGT CTG    2565
Thr Asn Glu Gln Ala Tyr Gln Met Leu Leu Ala Leu Val Arg Leu
            845             850                         855

GAC GCA GAG CAG CGA GCG CAG CAG AAC GGT ACA GAT TCT TTG GAC    2610
Asp Ala Glu Gln Arg Ala Gln Gln Asn Gly Thr Asp Ser Leu Asp
            860             865                         870

GGA CAG ACT GGC ACG CAG GAC AAG GGA CAG AAG CCC AAC CTG CTA    2655
Gly Gln Thr Gly Thr Gln Asp Lys Gly Gln Lys Pro Asn Leu Leu
            875             880                         885

GAC CGA CTG CGA CAC CGC AAA AAC GGC TAC CGA CAC TTG AAA GAC    2700
Asp Arg Leu Arg His Arg Lys Asn Gly Tyr Arg His Leu Lys Asp
            890             895                         900

TCC GAC GAA GAA GAG AAC GTC TGA                                2724
Ser Asp Glu Glu Glu Asn Val
            905
```

FIGURE 4A

| | | | | | | | | | | | | | |
|---|---|---|---|---|---|---|---|---|---|---|---|---|---|
| ATG | AAA | CAG | ATT | AAG | GTT | CGA | GTG | GAC | ATG | CTG | CGG | CAT AGA ATC | 45 |
| Met | Lys | Gln | Ile | Lys | Val | Arg | Val | Asp | Met | Leu | Arg | His Arg Ile | |
| 1 | | | | 5 | | | | | 10 | | | 15 | |

```
ATG AAA CAG ATT AAG GTT CGA GTG GAC ATG CTG CGG CAT AGA ATC      45
Met Lys Gln Ile Lys Val Arg Val Asp Met Leu Arg His Arg Ile
 1               5                   10                  15

AAG GAG CAC ATG CTG AAA AAA TAT ACC CAG ACG GAA GAG AAA TTC      90
Lys Glu His Met Leu Lys Lys Tyr Thr Gln Thr Glu Glu Lys Phe
                20                  25                  30

ACT GGC GCC TTT AAT ATG ATG GGA GGA TGT TTG CAG AAT GCC TTA     135
Thr Gly Ala Phe Asn Met Met Gly Gly Cys Leu Gln Asn Ala Leu
                35                  40                  45

GAT ATC TTA GAT AAG GTT CAT GAG CCT TTC GAG GAG ATG AAG TGT     180
Asp Ile Leu Asp Lys Val His Glu Pro Phe Glu Glu Met Lys Cys
                50                  55                  60

ATT GGG CTA ACT ATG CAG AGC ATG TAT GAG AAC TAC ATT GTA CCT     225
Ile Gly Leu Thr Met Gln Ser Met Tyr Glu Asn Tyr Ile Val Pro
                65                  70                  75

GAG GAT AAG CGG GAG ATG TGG ATG GCT TGT ATT AAG GAG CTG CAT     270
Glu Asp Lys Arg Glu Met Trp Met Ala Cys Ile Lys Glu Leu His
                80                  85                  90

GAT GTG AGC AAG GGC GCC GCT AAC AAG TTG GGG GGT GCA CTG CAG     315
Asp Val Ser Lys Gly Ala Ala Asn Lys Leu Gly Gly Ala Leu Gln
                95                 100                 105

GCT AAG GCC CGT GCT AAA AAG GAT GAA CTT AGG AGA AAG ATG ATG     360
Ala Lys Ala Arg Ala Lys Lys Asp Glu Leu Arg Arg Lys Met Met
               110                 115                 120

TAT ATG TGC TAC AGG AAT ATA GAG TTC TTT ACC AAG AAC TCA GCC     405
Tyr Met Cys Tyr Arg Asn Ile Glu Phe Phe Thr Lys Asn Ser Ala
               125                 130                 135

TTC CCT AAG ACC ACC AAT GGC TGC AGT CAG GCC ATG GCG GCA TTG     450
Phe Pro Lys Thr Thr Asn Gly Cys Ser Gln Ala Met Ala Ala Leu
               140                 145                 150

CAG AAC TTG CCT CAG TGC TCC CCT GAT GAG ATT ATG GCT TAT GCC     495
Gln Asn Leu Pro Gln Cys Ser Pro Asp Glu Ile Met Ala Tyr Ala
               155                 160                 165

CAG AAA ATA TTT AAG ATT TTG GAT GAG GAG AGA GAC AAG GTG CTC     540
Gln Lys Ile Phe Lys Ile Leu Asp Glu Glu Arg Asp Lys Val Leu
               170                 175                 180

ACG CAC ATT GAT CAC ATA TTT ATG GAT ATC CTC ACT ACA TGT GTG     585
Thr His Ile Asp His Ile Phe Met Asp Ile Leu Thr Thr Cys Val
               185                 190                 195

GAA ACA ATG TGT AAT GAG TAC AAG GTC ACT AGT GAC GCT TGT ATG     630
Glu Thr Met Cys Asn Glu Tyr Lys Val Thr Ser Asp Ala Cys Met
               200                 205                 210
```

FIGURE 4B

```
ATG ACC ATG TAC GGG GGC ATC TCT CTC TTA AGT GAG TTC TGT CGG      675
Met Thr Met Tyr Gly Gly Ile Ser Leu Leu Ser Glu Phe Cys Arg
            215                 220                 225

GTG CTG TCC TGC TAT GTC TTA GAG GAG ACT AGT GTG ATG CTG GCC      720
Val Leu Ser Cys Tyr Val Leu Glu Glu Thr Ser Val Met Leu Ala
            230                 235                 240

AAG CGG CCT CTG ATA ACC AAG CCT GAG GTT ATC AGT GTA ATG AAG      765
Lys Arg Pro Leu Ile Thr Lys Pro Glu Val Ile Ser Val Met Lys
            245                 250                 255

CGC CGC ATT GAG GAG ATC TGC ATG AAG GTC TTT GCC CAG TAC ATT      810
Arg Arg Ile Glu Glu Ile Cys Met Lys Val Phe Ala Gln Tyr Ile
            260                 265                 270

CTG GGG GCC GAT CCT CTG AGA GTC TGC TCT CCT AGT GTG GAT GAC      855
Leu Gly Ala Asp Pro Leu Arg Val Cys Ser Pro Ser Val Asp Asp
            275                 280                 285

CTA CGG GCC ATC GCC GAG GAG TCA GAT GAG GAA GAG GCT ATT GTA      900
Leu Arg Ala Ile Ala Glu Glu Ser Asp Glu Glu Glu Ala Ile Val
            290                 295                 300

GCC TAC ACT TTG GCC ACC CGT GGT GCC AGC TCC TCT GAT TCT CTG      945
Ala Tyr Thr Leu Ala Thr Arg Gly Ala Ser Ser Ser Asp Ser Leu
            305                 310                 315

GTG TCA CCC CCA GAG TCC CCT GTA CCC GCG ACT ATC CCT CTG TCC      990
Val Ser Pro Pro Glu Ser Pro Val Pro Ala Thr Ile Pro Leu Ser
            320                 325                 330

TCA GTA ATT GTG GCT GAG AAC AGT GAT CAG GAA GAA AGT GAG CAG     1035
Ser Val Ile Val Ala Glu Asn Ser Asp Gln Glu Glu Ser Glu Gln
            335                 340                 345

AGT GAT GAG GAA GAG GAG GAG GGT GCT CAG GAG GAG CGG GAG GAC     1080
Ser Asp Glu Glu Glu Glu Glu Gly Ala Gln Glu Glu Arg Glu Asp
            350                 355                 360

ACT GTG TCT GTC AAG TCT GAG CCA GTG TCT GAG ATA GAG GAA GTT     1125
Thr Val Ser Val Lys Ser Glu Pro Val Ser Glu Ile Glu Glu Val
            365                 370                 375

GCC CCA GAG GAA GAG GAG GAT GGT GCT GAG GAA CCC ACC GCC TCT     1170
Ala Pro Glu Glu Glu Glu Asp Gly Ala Glu Glu Pro Thr Ala Ser
            380                 385                 390

GGA GGC AAG AGC ACC CAC CCT ATG GTG ACT AGA AGC AAG GCT GAC     1215
Gly Gly Lys Ser Thr His Pro Met Val Thr Arg Ser Lys Ala Asp
            395                 400                 405

CAG TAA                                                          1221
Gln
```

FIGURE 5A

```
GCC ATG GCA TCC GTA CTG GGT CCC ATT TCG GGG CAC GTG CTG AAA        45
    Met Ala Ser Val Leu Gly Pro Ile Ser Gly His Val Leu Lys
     1           5                       10
        ATA
        Ile

GCC GTG TTT AGT CGC GGC GAC ACG CCG GTG CTG CCG CAC GAG ACG        90
Ala Val Phe Ser Arg Gly Asp Thr Pro Val Leu Pro His Glu Thr
 15              20                      25
                     T

CGA CTC CTG CAG ACG GGT ATC CAC GTG CGC GTG AGC CAG CCC TCG       135
Arg Leu Leu Gln Thr Gly Ile His Val Arg Val Ser Gln Pro Ser
 30              35                      40
                             A

CTG ATC CTG GTG TCG CAG TAC ACG CCC GAC TCG ACG CCA TGC CAC       180
Leu Ile Leu Val Ser Gln Tyr Thr Pro Asp Ser Thr Pro Cys His
 45              50                      55
         T   A

CGC GGC GAC AAT CAG CTG CAG GTG CAG CAC ACG TAC TTT ACG GGC       225
Arg Gly Asp Asn Gln Leu Gln Val Gln His Thr Tyr Phe Thr Gly
 60              65                      70

┌ 5' splice-donor
AGC GAG GTG GAG AAC GTG TCG GTC AAC│GTG CAC AAC CCC ACG GGC       270
Ser Glu Val Glu Asn Val Ser Val Asn│Val His Asn Pro Thr Gly
 75              80                └     85

3' splice-acceptor ┐
CGG AGC ATC TGC CCC AGC CAA│GAG CCC ATG TCG ATC TAT GTG TAC       315
Arg Ser Ile Cys Pro Ser Gln│Glu Pro Met Ser Ile Tyr Val Tyr
 90              95        ┘           100
 A                          G GCG CTG CCG CTC AAG ATG CTG AAC ATC CCC AGC ATC AAC GTG CAC       360
Ala Leu Pro Leu Lys Met Leu Asn Ile Pro Ser Ile Asn Val His
105             110                     115

CAC TAC CCG TCG GCG GCC GAG CGC AAA CAC CGA CAC CTG CCC GTA       405
His Tyr Pro Ser Ala Ala Glu Arg Lys His Arg His Leu Pro Val
120             125                     130

GCT GAC GCT GTG ATT CAC GCG TCG GGC AAG CAG ATG TGG CAG GCG       450
Ala Asp Ala Val Ile His Ala Ser Gly Lys Gln Met Trp Gln Ala
135             140                     145

CGT CTC ACG GTC TCG GGA CTG GCC TGG ACG CGT CAG CAG AAC CAG       495
Arg Leu Thr Val Ser Gly Leu Ala Trp Thr Arg Gln Gln Asn Gln
150             155                     160
```

FIGURE 5B

| | | | | | | | | | | | | | | |
|---|---|---|---|---|---|---|---|---|---|---|---|---|---|---|
| TGG | AAA | GAG | CCC | GAC | GTC | TAC | TAC | ACG | TCA | GCG | TTC | GTG | TTT | CCC | 540
| Trp | Lys | Glu | Pro | Asp | Val | Tyr | Tyr | Thr | Ser | Ala | Phe | Val | Phe | Pro |
| 165 | | | | 170 | | | | | 175 | | | | | |

```
TGG AAA GAG CCC GAC GTC TAC TAC ACG TCA GCG TTC GTG TTT CCC        540
Trp Lys Glu Pro Asp Val Tyr Tyr Thr Ser Ala Phe Val Phe Pro
165             170             175

ACC AAG GAC GTG GCA CTG CGG CAC GTG GTG TGC GCG CAC GAG CTG        585
Thr Lys Asp Val Ala Leu Arg His Val Val Cys Ala His Glu Leu
180             185             190

GTT TGC TCC ATG GAG AAC ACG CGC GCA ACC AAG ATG CAG GTG ATA        630
Val Cys Ser Met Glu Asn Thr Arg Ala Thr Lys Met Gln Val Ile
195             200             205

GGT GAC CAG TAC GTC AAG GTG TAC CTG GAG TCC TTC TGC GAG GAC        675
Gly Asp Gln Tyr Val Lys Val Tyr Leu Glu Ser Phe Cys Glu Asp
210             215             220

GTG CCC TCC GGC AAG CTC TTT ATG CAC GTC ACG CTG GGC TCT GAC        720
Val Pro Ser Gly Lys Leu Phe Met His Val Thr Leu Gly Ser Asp
225             230             235

GTG GAA GAG GAC CTG ACG ATG ACC CGC AAC CCG CAA CCC TTC ATG        765
Val Glu Glu Asp Leu Thr Met Thr Arg Asn Pro Gln Pro Phe Met
240             245             250

CGC CCC CAC GAG CGC AAC GGC TTT ACG GTG TTG TGT CCC AAA AAT        810
Arg Pro His Glu Arg Asn Gly Phe Thr Val Leu Cys Pro Lys Asn
255             260             265

ATG ATA ATC AAA CCG GGC AAG ATC TCG CAC ATC ATG CTG GAT GTG        855
Met Ile Ile Lys Pro Gly Lys Ile Ser His Ile Met Leu Asp Val
270             275             280

GCT TTT ACC TCA CAC GAG CAT TTT GGG CTG CTG TGT CCC AAG AGC        900
Ala Phe Thr Ser His Glu His Phe Gly Leu Leu Cys Pro Lys Ser
285             290             295

ATC CCG GGC CTG AGC ATC TCA GGT AAC CTA TTG ATG AAC GGG CAG        945
Ile Pro Gly Leu Ser Ile Ser Gly Asn Leu Leu Met Asn Gly Gln
300             305             310
                                      G

CAG ATC TTC CTG GAG GTG CAA GCG ATA CGC GAG ACC GTG GAA CTG        990
Gln Ile Phe Leu Glu Val Gln Ala Ile Arg Glu Thr Val Glu Leu
315             320             325
                  A     C

CGT CAG TAC GAT CCC GTG GCT GCG CTC TTC TTT TTC GAT ATC GAC       1035
Arg Gln Tyr Asp Pro Val Ala Ala Leu Phe Phe Phe Asp Ile Asp
330             335             340
```

FIGURE 5C

```
TTG CTG CTG CAG CGC GGG CCT CAG TAC AGC GAA CAC CCC ACC TTC    1080
Leu Leu Leu Gln Arg Gly Pro Gln Tyr Ser Glu His Pro Thr Phe
345             350                 355
                                    G

ACC AGC CAG TAT CGC ATC CAG GGC AAG CTT GAG TAC CGA CAC ACC    1125
Thr Ser Gln Tyr Arg Ile Gln Gly Lys Leu Glu Tyr Arg His Thr
360             365                 370

TGG GAC CGG CAC GAC GAG GGT GCC GCC CAG GGC GAC GAC GAC GTC    1170
Trp Asp Arg His Asp Glu Gly Ala Ala Gln Gly Asp Asp Asp Val
375             380                 385

TGG ACC AGC GGA TCG GAC TCC GAC GAG GAA CTC GTA ACC ACC GAG    1215
Trp Thr Ser Gly Ser Asp Ser Asp Glu Glu Leu Val Thr Thr Glu
390             395                 400
                        A

CGC AAG ACG CCC CGC GTT ACC GGC GGC GGC GCC ATG GCG GGC GCC    1260
Arg Lys Thr Pro Arg Val Thr Gly Gly Gly Ala Met Ala Gly Ala
405             410                 415
                    C

TCC ACT TCC GCG GGC CGC AAA CGC AAA TCA GCA TCC TCG GCG ACG    1305
Ser Thr Ser Ala Gly Arg Lys Arg Lys Ser Ala Ser Ser Ala Thr
420             425                 430

GCG TGC ACG GCG GGC GTT ATG ACA CGC GGC CGC CTT AAG GCC GAG    1350
Ala Cys Thr Ala Gly Val Met Thr Arg Gly Arg Leu Lys Ala Glu
435             440                 445
        T
        Ser

TCC ACC GTC GCG CCC GAA GAG GAC ACC GAC GAG GAT TCC GAC AAC    1395
Ser Thr Val Ala Pro Glu Glu Asp Thr Asp Glu Asp Ser Asp Asn
450             455                 460

GAA ATC CAC AAT CCG GCC GTG TTC ACC TGG CCG CCC TGG CAG GCC    1440
Glu Ile His Asn Pro Ala Val Phe Thr Trp Pro Pro Trp Gln Ala
465             470                 475

GGC ATC CTG GCC CGC AAC CTG GTG CCC ATG GTT GCT ACG GTT CAG    1485
Gly Ile Leu Ala Arg Asn Leu Val Pro Met Val Ala Thr Val Gln
480             485                 490

GGT CAG AAT CTG AAG TAC CAG GAG TTC TTC TGG GAC GCC AAC GAC    1530
Gly Gln Asn Leu Lys Tyr Gln Glu Phe Phe Trp Asp Ala Asn Asp
495             500                 505
                        A
```

FIGURE 5D

```
ATC TAC CGC ATC TTC GCC GAA TTG GAA GGC GTA TGG CAG CCC GCT      1575
Ile Tyr Arg Ile Phe Ala Glu Leu Glu Gly Val Trp Gln Pro Ala
510                 515                 520

GCG CAA CCC AAA CGT CGC CGC CAC CGG CAA GAC GCC TTG CCC GGG      1620
Ala Gln Pro Lys Arg Arg Arg His Arg Gln Asp Ala Leu Pro Gly
525                 530                 535

CCA TGC ATC GCC TCG ACG CCC AAA AAG CAC CGA GGT TGAGCCACCC       1666
Pro Cys Ile Ala Ser Thr Pro Lys Lys His Arg Gly
540                 545                 550

GCCGCGCACG CTTAGGACGA CTCTATAAAA ACCCACGTCC ACTCAGACAC            1716
      A G

GCGACTTTTG GCCGCCACAC CTGTCGCCGC TGCTATATTT GCGACAGTTG            1766
   A                       A

CCGGAACCCT TCCCGACCTC CCACGAAGAC CCGTTCACCT TTGCGCATCC            1816

CCTGACCCCC CCCCTCATCC CGCCTTCGCG ATG TCT CAG GCA TCG TCC TCG     1867
                                  Met Ser Gln Ala Ser Ser Ser
                                                        555
        T         C           A

CCC GGT GAG GGA CCC TCG TCG GAA GCG GCC GCG ATC AGC GAG GCC      1912
Pro Gly Glu Gly Pro Ser Ser Glu Ala Ala Ala Ile Ser Glu Ala
    560                 565                 570

Hind III
GAA GCC GCC AGC GGA AGC TT                                       1932
Glu Ala Ala Ser Gly Ser
    575
```

FIGURE 6A

```
TAGATCACCG ATAGAAATTT ACACGAGGCC ACGCCGGCCG GCAACAGCCA        50

CTGGTTGCTG AGTACGATAA AGGGTAGCAC AGTAAGCGTG AGAAAATTAG       100

TAGAGTAGAG GTTGGTCATG TAAATGGTGG GCGTCGAATA GCCAAGCACG       150

CGATTCGTGA GCAGCTGCGT GATCAACACT ATGGCGTTAA GTGGACCGCC       200

CACGAAGATG ATGAATGTGT TGAGTACGGC TTCGGTGGTT CGAATGGCGA       250

ATAGCGGCCC TGTCATGTTG CAAGTGTCAT TGATGTGCGG AGGAGTGTTG       300

TTGCGGGTCT GGGCGGAACA GCACACGGGG CGAAAAAACA GAAGAAACAA       350

>>>>>>>
GTCAGCGGCG CTTAAAAGAA AACCGCGTAT CCGCCTCCGC TATTAAACTA       400

--------->
CCCCCCCTCC CTCTAGGTGG GGCGCTCACC GAGTTGTGGA TGATGGTGTC       450

Sac II
CATCGTGGGC GAATAGCAGA CCGCGGGCGC AGTCCGGGGC GACGACGCTT       500
```

```
CCGGGTTCTG GAGAAAGCC AGC ATG AGT TTG CAG TTT ATC GGT CTA CAG  550
                        Met Ser Leu Gln Phe Ile Gly Leu Gln
                         1                  5

CGG CGC GAT GTG GTA GCC CTG GTC AAC TTT CTG CGC CAT CTC ACG   595
Arg Arg Asp Val Val Ala Leu Val Asn Phe Leu Arg His Leu Thr
 10              15                  20

CAA AAG CCC GAC GTG GAT CTC GAG GCA CAC CCC AAG ATC CTG AAA   640
Gln Lys Pro Asp Val Asp Leu Glu Ala His Pro Lys Ile Leu Lys
 25              30                  35

AAA TGT GGC GAA AAA CGC CTG CAC CGG CGT ACG GTG CTG TTC AAC   685
Lys Cys Gly Glu Lys Arg Leu His Arg Arg Thr Val Leu Phe Asn
 40              45                  50

GAG CTC ATG CTT TGG TTG GGA TAC TAC CGC GAG CTG CGT TTT CAC   730
Glu Leu Met Leu Trp Leu Gly Tyr Tyr Arg Glu Leu Arg Phe His
 55              60                  65

AAC CCC GAC CTC TCC TCA GTG CTC GAG GAG TTC GAG GTG CGT TGC   775
Asn Pro Asp Leu Ser Ser Val Leu Glu Glu Phe Glu Val Arg Cys
 70              75                  80

GTG GCC GTG GCG CGT CGC GGC TAC ACT TAC CCG TTC GGT GAT CGT   820
Val Ala Val Ala Arg Arg Gly Tyr Thr Tyr Pro Phe Gly Asp Arg
 85              90                  95
```

FIGURE 6B

```
                                                    Eco RI
GGT AAG GCG CGT GAC CAC CTG GCT GTG CTA GAC CGT ACC GAA TTC    865
Gly Lys Ala Arg Asp His Leu Ala Val Leu Asp Arg Thr Glu Phe
100             105                 110

GAT ACG GAC GTG CGC CAC GAT GCC GAG ATC GTG GAA CGC GCG CTC    910
Asp Thr Asp Val Arg His Asp Ala Glu Ile Val Glu Arg Ala Leu
115             120                 125

GTA AGC GCG GTC ATT CTG GCC AAG ATG TCG GTG CGC GAG ACG CTG    955
Val Ser Ala Val Ile Leu Ala Lys Met Ser Val Arg Glu Thr Leu
130             135                 140

GTC ACA GCC ATC GGC CAG ACG GAA CCC ATC GCC TTT GTG CAC CTC    1000
Val Thr Ala Ile Gly Gln Thr Glu Pro Ile Ala Phe Val His Leu
145             150                 155

AAG GAT ACG GAG GTG CAG CGC ATT GAA GAA AAC CTG GAG GGT GTG    1045
Lys Asp Thr Glu Val Gln Arg Ile Glu Glu Asn Leu Glu Gly Val
160             165                 170

CGC CGT AAC ATG TTC TGC GTG AAA CCG CTC GAC CTT AAC CTG GAC    1090
Arg Arg Asn Met Phe Cys Val Lys Pro Leu Asp Leu Asn Leu Asp
175             180                 185

CGG CAC GCC AAC ACG GCG CTG GTC AAC GCC GTC AAC AAG CTC GTG    1135
Arg His Ala Asn Thr Ala Leu Val Asn Ala Val Asn Lys Leu Val
190             195                 200

TAC ACG GGC CGT CTC ATC ATG AAC GTG CGC AGG TCT TGG GAG GAG    1180
Tyr Thr Gly Arg Leu Ile Met Asn Val Arg Arg Ser Trp Glu Glu
205             210                 215

CTG GAG CGC AAA TGT CTG GCG CGC ATT CAG GAG CGC TGC AAG CTG    1225
Leu Glu Arg Lys Cys Leu Ala Arg Ile Gln Glu Arg Cys Lys Leu
220             225                 230

CTG GTC AAG GAG CTG CGC ATG TGC CTT TCC TTT GAT TCC AAC TAC    1270
Leu Val Lys Glu Leu Arg Met Cys Leu Ser Phe Asp Ser Asn Tyr
235             240                 245

TGT CGC AAT ATC CTC AAG CAC GCC GTG GAA AAC GGC GAC TCG GCC    1315
Cys Arg Asn Ile Leu Lys His Ala Val Glu Asn Gly Asp Ser Ala
250             255                 260

GAC ACG CTG TTG GAG CTG CTC ATC GAG GAC TTT GAT ATC TAC GTG    1360
Asp Thr Leu Leu Glu Leu Leu Ile Glu Asp Phe Asp Ile Tyr Val
265             270                 275
```

FIGURE 6C

```
GAC AGC TTC CCA CAG TCG GCG CAC ACG TTT TTG GGC GCG CGC TCG    1405
Asp Ser Phe Pro Gln Ser Ala His Thr Phe Leu Gly Ala Arg Ser
280             285                 290

CCG TCG TTG GAG TTT GAC GAT GAC GCC AAT CTC CTC TCG CTC GGC    1450
Pro Ser Leu Glu Phe Asp Asp Asp Ala Asn Leu Leu Ser Leu Gly
295             300                 305

GGC GGT TCG GCC TTC TCG TCG GTA CCC AAG AAA CAT GTC CCC ACG    1495
Gly Gly Ser Ala Phe Ser Ser Val Pro Lys Lys His Val Pro Thr
310             315                 320

CAG CCG CTG GAC GGC TGG AGC TGG ATC GCC AGT CCC TGG AAG GGA    1540
Gln Pro Leu Asp Gly Trp Ser Trp Ile Ala Ser Pro Trp Lys Gly
325             330                 335

CAC AAA CCG TTC CGC TTC GAG GCC CAT GGT TCT CTG GCA CCG GCC    1585
His Lys Pro Phe Arg Phe Glu Ala His Gly Ser Leu Ala Pro Ala
340             345                 350

GCC GAA GCC CAC GCT GCC CGT TCG GCG GCC GTC GGC TAT TAC GAC    1630
Ala Glu Ala His Ala Ala Arg Ser Ala Ala Val Gly Tyr Tyr Asp
355             360                 365

GAA GAG GAA AAG CGT CGC GAG CGG CAG AAA CGG GTG GAC GAC GAG    1675
Glu Glu Glu Lys Arg Arg Glu Arg Gln Lys Arg Val Asp Asp Glu
370             375                 380

GTG GTG CAG CGT GAG AAA CAG CAG CTG AAG GCT TGG GAG GAG AGG    1720
Val Val Gln Arg Glu Lys Gln Gln Leu Lys Ala Trp Glu Glu Arg
385             390                 395
            Pst I
CAG CAG AAC CTG CAG CAA CGT CAG CAG CAA CCA CCG CCC CCG GCA    1765
Gln Gln Asn Leu Gln Gln Arg Gln Gln Gln Pro Pro Pro Pro Ala
400             405                 410

CGT AAA CCG AGC GCC TCC CGG AGG CTC TTT GGC TCC AGT GCC GAT    1810
Arg Lys Pro Ser Ala Ser Arg Arg Leu Phe Gly Ser Ser Ala Asp
415             420                 425

GAG GAC GAC GAC GAT GAT GAC GAG AAA AAC ATC TTT ACG CCC        1855
Glu Asp Asp Asp Asp Asp Asp Glu Lys Asn Ile Phe Thr Pro
430             435                 440

ATC AAG AAA CCG GGA ACT AGC GGC AAG GGC GCC GCT AGT GGT GGC    1900
Ile Lys Lys Pro Gly Thr Ser Gly Lys Gly Ala Ala Ser Gly Gly
445             450                 455

GGT GTT TCC AGC ATT TTC AGC GGC CTG TTA TCC TCG GGC AGT CAG    1945
Gly Val Ser Ser Ile Phe Ser Gly Leu Leu Ser Ser Gly Ser Gln
460             465                 470
```

FIGURE 6D

| | | | | | | | | | | | | |
|---|---|---|---|---|---|---|---|---|---|---|---|---|
| AAA | CCG | ACC | AGC | GGT | CCC | TTG | AAC | ATC | CCG | CAA | CAA | CAA CAG CGT | 1990
| Lys | Pro | Thr | Ser | Gly | Pro | Leu | Asn | Ile | Pro | Gln | Gln | Gln Gln Arg |
| 475 | | | | | 480 | | | | | 485 | | |

```
AAA CCG ACC AGC GGT CCC TTG AAC ATC CCG CAA CAA CAA CAG CGT    1990
Lys Pro Thr Ser Gly Pro Leu Asn Ile Pro Gln Gln Gln Gln Arg
475             480             485

CAC GCG GCT TTC AGT CTC GTC TCC CCG CAG GTG ACC AAG GCC AGC    2035
His Ala Ala Phe Ser Leu Val Ser Pro Gln Val Thr Lys Ala Ser
490             495             500

CCG GGA AGG GTC CGT CGG GAC AGC GCG TGG GAC GTG AGG CCG CTC    2080
Pro Gly Arg Val Arg Arg Asp Ser Ala Trp Asp Val Arg Pro Leu
505             510             515

ACG GAG ACC AGA GGG GAT CTT TTC TCG GGC GAC GAG GAT TCC GAC    2125
Thr Glu Thr Arg Gly Asp Leu Phe Ser Gly Asp Glu Asp Ser Asp
520             525             530

AGC TCG GAT GGC TAT CCC CCC AAC CGT CAA GAT CCG CGT TTC ACC    2170
Ser Ser Asp Gly Tyr Pro Pro Asn Arg Gln Asp Pro Arg Phe Thr
535             540             545

GAC ACG CTG GTG GAC ATC ACG GAT ACC GAG ACG AGC GCC AAA CCG    2215
Asp Thr Leu Val Asp Ile Thr Asp Thr Glu Thr Ser Ala Lys Pro
550             555             560

CCC GTC ACC ACC GCG TAC AAG TTC GAG CAA CCG ACG TTG ACG TTC    2260
Pro Val Thr Thr Ala Tyr Lys Phe Glu Gln Pro Thr Leu Thr Phe
565             570             575

GGC GCC GGA GTT AAC GTT CCT GCT GGC GCC GGC GCC ATC CTC        2305
Gly Ala Gly Val Asn Val Pro Ala Gly Ala Gly Ala Ala Ile Leu
580             585             590

ACG CCG ACG CCT GTC AAT CCT TCC ACG GCC CCC GCT CCG GCC CCG    2350
Thr Pro Thr Pro Val Asn Pro Ser Thr Ala Pro Ala Pro Ala Pro
595             600             605

ACA CCT ACC TTC GCG GGT ACC CAA ACC CCG GTC AAC GGT AAC TCG    2395
Thr Pro Thr Phe Ala Gly Thr Gln Thr Pro Val Asn Gly Asn Ser
610             615             620

CCC TGG GCT CCG ACG GCG CCG TTG CCC GGG GAT ATG AAC CCC GCC    2440
Pro Trp Ala Pro Thr Ala Pro Leu Pro Gly Asp Met Asn Pro Ala
625             630             635

AAC TGG CCG CGC GAA CGC GCG TGG GCC CTC AAG AAT CCT CAC CTG    2485
Asn Trp Pro Arg Glu Arg Ala Trp Ala Leu Lys Asn Pro His Leu
640             645             650

GCT TAC AAT CCC TTC AGG ATG CCT ACG ACT TCC ACG GCT TCT CAA    2530
Ala Tyr Asn Pro Phe Arg Met Pro Thr Thr Ser Thr Ala Ser Gln
655             660             665
```

FIGURE 6E

```
AAC ACC GTG TCC ACC ACC CCT CGG AGG CCG TCG ACT CCA CGC GCC    2575
Asn Thr Val Ser Thr Thr Pro Arg Arg Pro Ser Thr Pro Arg Ala
670             675                 680

GCG GTG ACA CAA ACA GCG TCT CGG GAC GCC GCT GAT GAG GTT TGG    2620
Ala Val Thr Gln Thr Ala Ser Arg Asp Ala Ala Asp Glu Val Trp
685             690                 695
                        Pst I
GCT TTA AGG GAC CAA ACT GCA GAG TCA CCG GTC GAA GAC AGC GAG    2665
Ala Leu Arg Asp Gln Thr Ala Glu Ser Pro Val Glu Asp Ser Glu
700             705                 710

GAG GAA GAC GAC GAC TCC TCG GAC ACC GGC TCC GTC GTC AGC CTG    2710
Glu Glu Asp Asp Asp Ser Ser Asp Thr Gly Ser Val Val Ser Leu
715             720                 725

GGA CAC ACA ACA CCG TCG TCC GAT TAC AAC AAC GAC GTC ATT TCG    2755
Gly His Thr Thr Pro Ser Ser Asp Tyr Asn Asn Asp Val Ile Ser
730             735                 740

CCT CCC AGT CAG ACG CCC GAG CAG TCG ACG CCG TCC AGA ATA CGT    2800
Pro Pro Ser Gln Thr Pro Glu Gln Ser Thr Pro Ser Arg Ile Arg
745             750                 755

AAA GCT AAG TTA TCG TCT CCA ATG ACG ACG ACA TCC ACG AGC CAG    2845
Lys Ala Lys Leu Ser Ser Pro Met Thr Thr Thr Ser Thr Ser Gln
760             765                 770

AAA CCG GTG CTG GGC AAG CGA GTC GCG ACG CCG CAC GCG TCC GCC    2890
Lys Pro Val Leu Gly Lys Arg Val Ala Thr Pro His Ala Ser Ala
775             780                 785

CGA GCG CAG ACG GTG ACG TCG ACG CCG GTT CAG GGA AGG CTA GAG    2935
Arg Ala Gln Thr Val Thr Ser Thr Pro Val Gln Gly Arg Leu Glu
790             795                 800

AAA CAG GTG TCG GGC ACG CCG TCG ACG GTA CCC GCC ACG CTG TTG    2980
Lys Gln Val Ser Gly Thr Pro Ser Thr Val Pro Ala Thr Leu Leu
805             810                 815

CAA CCT CAA CCG GCT TCG TCT AAA ACG ACG TCA TCA AGG AAC GTG    3025
Gln Pro Gln Pro Ala Ser Ser Lys Thr Thr Ser Ser Arg Asn Val
820             825                 830

ACT TCT GGC GCG GGA ACC TCT TCC GCT TCT TCG GCT CGA CAG CCG    3070
Thr Ser Gly Ala Gly Thr Ser Ser Ala Ser Ser Ala Arg Gln Pro
835             840                 845
```

FIGURE 6F

```
TCA GCC TCG GCG TCC GTT TTG TCG CCC ACG GAG GAT GAT GTC GTG   3115
Ser Ala Ser Ala Ser Val Leu Ser Pro Thr Glu Asp Asp Val Val
850                 855                 860

TCC CCC GCC ACA TCG CCG CTG TCC ATG CTT TCG TCA GCC TCT CCG   3160
Ser Pro Ala Thr Ser Pro Leu Ser Met Leu Ser Ser Ala Ser Pro
865                 870                 875

TCC CCG GCC AAG AGT GCC CCC CCG TCT CCG GTG AAA GGC CGG GGC   3205
Ser Pro Ala Lys Ser Ala Pro Pro Ser Pro Val Lys Gly Arg Gly
880                 885                 890

AGC CGC GTC GGT GTT CCT TCC TTG AAA CCT ACT TTG GGC GGC AAG   3250
Ser Arg Val Gly Val Pro Ser Leu Lys Pro Thr Leu Gly Gly Lys
895                 900                 905

GCG GTG GTA GGT CGA CCG CCC TCG GTC CCC GTG AGC GGT AGC GCG   3295
Ala Val Val Gly Arg Pro Pro Ser Val Pro Val Ser Gly Ser Ala
910                 915                 920

CCG GGT CGC CTG TCC GGC AGC AGC CGG GCC GCC TCG ACC ACG CCG   3340
Pro Gly Arg Leu Ser Gly Ser Ser Arg Ala Ala Ser Thr Thr Pro
925                 930                 935

ACG TAT CCC GCG GTA ACC ACC GTT TAC CCA CCG TCG TCT ACG GCC   3385
Thr Tyr Pro Ala Val Thr Thr Val Tyr Pro Pro Ser Ser Thr Ala
940                 945                 950

AAA AGC AGC GTA TCG AAT GCG CCG CCT GTG GCC TCC CCC TCC ATC   3430
Lys Ser Ser Val Ser Asn Ala Pro Pro Val Ala Ser Pro Ser Ile
955                 960                 965

CTG AAA CCG GGG GCG AGC GCG GCT TTG CAA TCA CGC CGC TCG ACG   3475
Leu Lys Pro Gly Ala Ser Ala Ala Leu Gln Ser Arg Arg Ser Thr
970                 975                 980

GGG ACC GCC GCC GTA GGT TCC CCC GTC AAG AGC ACG ACG GGC ATG   3520
Gly Thr Ala Ala Val Gly Ser Pro Val Lys Ser Thr Thr Gly Met
985                 990                 995

AAA ACG GTG GCT TTC GAC CTA TCG TCG CCC CAG AAG AGC GGT ACG   3565
Lys Thr Val Ala Phe Asp Leu Ser Ser Pro Gln Lys Ser Gly Thr
1000                1005                1010

GGG CCG CAA CCG GGT TCT GCC GGC ATG GGG GGC GCC AAA ACG CCG   3610
Gly Pro Gln Pro Gly Ser Ala Gly Met Gly Gly Ala Lys Thr Pro
1015                1020                1025

TCG GAC GCC GTG CAG AAC ATC CTC CAA AAG ATC GAG AAG ATT AAG   3655
Ser Asp Ala Val Gln Asn Ile Leu Gln Lys Ile Glu Lys Ile Lys
1030                1035                1040
```

FIGURE 6G

| | | | | |
|---|---|---|---|---|
| AAC ACG GAG GAA | TAGTTAAGAA | ACACACACGC | AGACGTACTT | TTTAATGAAA | 3707
| Asn Thr Glu Glu | | | | |
| 1045 | | | | |

```
CCATCGGATA GTGACGTGTC GGGAAAGGAG GACGGACGGA GGGTCAGGGA   3757
TGGGGAGACG TGAGAAAGTT GTCCGCGGGC AATTGCATGT CGCCCAGAAA   3807
GAACGTGGTT GTTCCGGCGG CGTGCATCTG CCGAAACACC GTGTGGTGGT   3857
TGTACGAGTA CACGTTACCG TCGCCCTCGG TAATTTGATA CAACGTGGCG   3907
ATGGGGGTGC CCTGCGGGAT CACGATGGAA CGCGTGCGCG TCCACAGCGT   3957
GACTTTGAGC GGCTCGCCGC CGCGCCACAC GCTGAGCCCC GTGTAAAAGG   4007
CGTCCTCGTG TGGCAAGTTG GCCACCAAGA ACACCGGTC  TGTGATCTGC   4057
ACGTAGCGCA AGTCCAACTC CACCGTCTGC CGCGGTTGCA CCCCGAAGTG   4107
GATATCGTAA GGCGCGTGCA CCGTGAGCGA AAACACGTTG GGCTCATTGA   4157
GAAGCGGACA GTTGAGCGCG TCGCCGCTAA AAAGAGTGA  CGGGTTGCGG   4207
CTGAATCGCA GGTCGTACCC GCGCTGCGCG CTCGTCAGCA GGTAGAAGGA   4257
AAAAGCGCGC GGCATGTTGC GCGCCGTGAT CTTGTCCGAG ACGCGGTGAC   4307
AGAAGGAGGT GGCCACGGTG CCCAGCAGTT GGCGCTGTTC CGCGTCCACG   4357
                                           Eco RI
CATAGTGAAT CCACGTTGAC GGTGAAAATG AGACCCATGA ATTCGTACTG   4407
CACGTTTTTG GACGCGATCC ACGCTTCGTC CTCGCCGGGT AGCGCTGCCT   4457
CGTCGTCGTC CATCGTGCCG CGGAACTGCG CGAGGTAGCG CGTAATTTTT   4507
TTGTGTCCGT ACGTGGTTAC GCGCTTACTG ATCCAGGTCA GATGGTCCAC   4557
GCGACATAGC AGCGTCGCGC CATGCCGCGT GACGCTGACC CGTCCAAGG    4607
GCGCCGCCTC CTCCAACCCC GCAACGCCGC TCGGAGCACC GCCGCAGCCC   4657
GGCTTTCCCG GCGTCGTGAA AGGCACGGCG TAATGCGGGC AGGCGTGCGG   4707
CACGAAGGGC ACCATGACCA GTTGTGTGTG CAGAAACCG  ATCTGCACCG   4757
CCTGCGACTG CCGCATGGTT TCCTCGTCGT AAACCGCCAT GGACGAGCAG   4807
AGCCCGCCCT TGGTGATGAG CGGTTGCAGC ACCACGGAGC TCTCGCTGGT   4857
```

FIGURE 6H

```
GGAGCAGAGC AGAAAGAAGA GCTCGGCGTA CGCCGCCTTG GGCGTCACCA      4907
CGTTGGACCA GTCGTACTTG TAGCCGCAGC CCTGCGTGTT GTTGTAAATG      4957
                                         Hind III
ACGGGAAACG AGAGAAAGAT GCAGCCCTGC ACGTACGAAG CTTTCTCCGT      5007
CACGTTCGAG GCCGTGTTGT ACTGCTCGGT GATGGACACC AAGTACGACT      5057
CGTAGGCCGT CAGGTGCGAG GCCGAACGGT GAATCTTGGC GTGGCGCACG      5107
CAGCGACCGT AGTTGTCGCG GTCCGCGTCG CGTAGCGCTT CGATCCACGA      5157
GGTCACCACG TCCTGCGCCG GCAGACGATA GTCCTGCTCG GGTCCATGT       5207
GGCGGCACAG CCGCAGGCGC TCTGCCAGTT GGCGAGGGAT ACCGTCGTGC      5257
GACCTTTTGA CCGCGGTGGT GCCTGTCGTC CTCGTCTCCC CTCCTTCGTT      5307
                                    Bam HI
CTCCCTGTTT TCTCTTCTCT CATTCCCGGT CTCCGGATCC GCAGCCGCTA      5357
CCTCTTGCTC CGCGGTTTTC TCGCCCACCT CGCTCGTCGC TGTCGCCGCC      5407
ACCGCAGCGG CGGCGACGGA CGGCGGCGGT AACAACAGCT CCGTGAAGCT      5457
GACGAGCGGC AGCGGCGACG ACGGTGGCGG CGACGACACG GCGACGGTCA      5507
ACAGGGTCAC AAGCGTGGGT TTGTCCCCCA TAATCTGGTC GCCGCCACCG      5557
CCGTCGTTGC CGGTCCCCGT TTCCTCCGGC GTCGCGGTTT CCGCCGTCTC      5607
CGGATGAGCG GCCGCGGCGC GGGCTCGGCG TCCCGCCGTC CGAGACGGTG      5657
TATATAAACC GCGTCGGCCT CGCCGGCCCG AGCGCGCCGG GGAGAAGAAC      5707
CTCTTCCCGG GCCCCGCGTT CAAGACGGCG TGCCGTGACG CTCGATGGGT      5757
CCGCTTCATC AGACTGCGTA CGCTTTGGAG CGTCAGACCC AGGGCGCATG      5807
TAGCCGACTT GGAGGACTTT GCCGCCTTTT ATCGCACCCT CTCGGACAGT      5857
GAGCAGCAGG AGTTCGAGCA AGAAGCCGAA CTCGCCTCCC GCTCACAACG      5907
CGTGCAACAC CTGCGCGAGG CCCGGCGCCA GCTCAAGATG GACCTGATGT      5957
GTCACGGCGG TTGAAAACGC GCATGATCTC GCGAAGCCAT CTACGCGCCT      6007
GTCAGGGCGA TGACGACATC AGCGATGACG GCTCCTGATA CGCGCCGGCA      6057
```

FIGURE 6I

```
 Pst I
GCTGCAGCAC GTGGAGACGC TGCGTCGGTT TCTGCGCGGC GACAGCTGCT      6107

TTGTGCACGA TCTCCCGGGC ATGATGGACT ATCACGACGG GCTCTCGCGC      6157

CGTCAACAGC GTGCCTTTTG CCGCGCGAGT CGCGTGTTGA CGGACCCGGA      6207

**  ****              --
GCCCATCCAG AGCGAAGCGG AGGGGGAGAA TAAACAGTTT ACGGAGCACA      6257

_____]                   ******                ---
CACACAAAGT AGTCTCGTTT TTTATTAAAA GTGTCTTTGT ATTTCCCTAT      6307

___]
CTTGTGTTGC CCAACTGCTG TCAGGTCTCC GTAGATCGCT CCCGGGTGCC CGA  6360
```

2255-2920: hCMV IE1 enhancer/promoter
2923-2951: Multiple cloning sites
2952-3650: BGH terminator
3651-4051 and 1-2254: pUC19

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 2724 base pairs
      (B) TYPE: nucleic acid
      (C) STRANDEDNESS: double
      (D) TOPOLOGY: unknown (ii) MOLECULE TYPE: cDNA (ix) FEATURE:
      (A) NAME/KEY: CDS
      (B) LOCATION: 1..2721

(xi) SEQUENCE DESCRIPTION: SEQ ID NO: 1:

```
ATG GAA TCC AGG ATC TGG TGC CTG GTA GTC TGC GTT AAC TTG TGT ATC      48
Met Glu Ser Arg Ile Trp Cys Leu Val Val Cys Val Asn Leu Cys Ile
  1               5                  10                  15

GTC TGT CTG GGT GCT GCG GTT TCC TCA TCT TCT ACT CGT GGA ACT TCT      96
Val Cys Leu Gly Ala Ala Val Ser Ser Ser Ser Thr Arg Gly Thr Ser
             20                  25                  30

GCT ACT CAC AGT CAC CAT TCC TCT CAT ACG ACG TCT GCT GCT CAT TCT     144
Ala Thr His Ser His His Ser Ser His Thr Thr Ser Ala Ala His Ser
         35                  40                  45
```

```
CGA TCC GGT TCA GTC TCT CAA CGC GTA ACT TCT TCC CAA ACG GTC AGC      192
Arg Ser Gly Ser Val Ser Gln Arg Val Thr Ser Ser Gln Thr Val Ser
 50                  55                  60

CAT GGT GTT AAC GAG ACC ATC TAC AAC ACT ACC CTC AAG TAC GGA GAT      240
His Gly Val Asn Glu Thr Ile Tyr Asn Thr Thr Leu Lys Tyr Gly Asp
 65                  70                  75                  80

GTG GTG GGG GTC AAC ACC ACC AAG TAC CCC TAT CGC GTG TGT TCT ATG      288
Val Val Gly Val Asn Thr Thr Lys Tyr Pro Tyr Arg Val Cys Ser Met
                 85                  90                  95

GCA CAG GGT ACG GAT CTT ATT CGC TTT GAA CGT AAT ATC GTC TGC ACC      336
Ala Gln Gly Thr Asp Leu Ile Arg Phe Glu Arg Asn Ile Val Cys Thr
            100                 105                 110

TCG ATG AAG CCC ATC AAT GAA GAC CTG GAC GAG GGC ATC ATG GTG GTC      384
Ser Met Lys Pro Ile Asn Glu Asp Leu Asp Glu Gly Ile Met Val Val
                115                 120                 125

TAC AAA CGC AAC ATC GTC GCG CAC ACC TTT AAG GTA CGA GTC TAC CAG      432
Tyr Lys Arg Asn Ile Val Ala His Thr Phe Lys Val Arg Val Tyr Gln
130                 135                 140

AAG GTT TTG ACG TTT CGT CGT AGC TAC GCT TAC ATC CAC ACC ACT TAT      480
Lys Val Leu Thr Phe Arg Arg Ser Tyr Ala Tyr Ile His Thr Thr Tyr
145                 150                 155                 160

CTG CTG GGC AGC AAC ACG GAA TAC GTG GCG CCT CCT ATG TGG GAG ATT      528
Leu Leu Gly Ser Asn Thr Glu Tyr Val Ala Pro Pro Met Trp Glu Ile
                165                 170                 175

CAT CAT ATC AAC AGT CAC AGT CAG TGC TAC AGT TCC TAC AGC CGC GTT      576
His His Ile Asn Ser His Ser Gln Cys Tyr Ser Ser Tyr Ser Arg Val
            180                 185                 190

ATA GCA GGC ACG GTT TTC GTG GCT TAT CAT AGG GAC AGC TAT GAA AAC      624
Ile Ala Gly Thr Val Phe Val Ala Tyr His Arg Asp Ser Tyr Glu Asn
        195                 200                 205

AAA ACC ATG CAA TTA ATG CCC GAC GAT TAT TCC AAC ACC CAC AGT ACC      672
Lys Thr Met Gln Leu Met Pro Asp Asp Tyr Ser Asn Thr His Ser Thr
210                 215                 220

CGT TAC GTG ACG GTC AAG GAT CAA TGG CAC AGC CGC GGC AGC ACC TGG      720
Arg Tyr Val Thr Val Lys Asp Gln Trp His Ser Arg Gly Ser Thr Trp
225                 230                 235                 240

CTC TAT CGT GAG ACC TGT AAT CTG AAT TGT ATG GTG ACC ATC ACT ACT      768
Leu Tyr Arg Glu Thr Cys Asn Leu Asn Cys Met Val Thr Ile Thr Thr
                245                 250                 255

GCG CGC TCC AAG TAT CCC TAT CAT TTT TTC GCA ACT TCC ACG GGT GAT      816
Ala Arg Ser Lys Tyr Pro Tyr His Phe Phe Ala Thr Ser Thr Gly Asp
            260                 265                 270

GTG GTT GAC ATT TCT CCT TTC TAC AAC GGA ACT AAT CGC AAT GCC AGC      864
Val Val Asp Ile Ser Pro Phe Tyr Asn Gly Thr Asn Arg Asn Ala Ser
        275                 280                 285

TAT TTT GGA GAA AAC GCC GAC AAG TTT TTC ATT TTT CCG AAC TAC ACT      912
Tyr Phe Gly Glu Asn Ala Asp Lys Phe Phe Ile Phe Pro Asn Tyr Thr
290                 295                 300

ATC GTC TCC GAC TTT GGA AGA CCG AAT TCT GCG TTA GAG ACC CAC AGG      960
Ile Val Ser Asp Phe Gly Arg Pro Asn Ser Ala Leu Glu Thr His Arg
305                 310                 315                 320

TTG GTG GCT TTT CTT GAA CGT GCG GAC TCA GTG ATC TCC TGG GAT ATA     1008
Leu Val Ala Phe Leu Glu Arg Ala Asp Ser Val Ile Ser Trp Asp Ile
                325                 330                 335

CAG GAC GAG AAG AAT GTT ACT TGT CAA CTC ACT TTC TGG GAA GCC TCG     1056
Gln Asp Glu Lys Asn Val Thr Cys Gln Leu Thr Phe Trp Glu Ala Ser
            340                 345                 350

GAA CGC ACC ATT CGT TCC GAA GCC GAG GAC TCG TAT CAC TTT TCT TCT     1104
Glu Arg Thr Ile Arg Ser Glu Ala Glu Asp Ser Tyr His Phe Ser Ser
        355                 360                 365
```

```
GCC AAA ATG ACC GCC ACT TTC TTA TCT AAG AAG CAA GAG GTG AAC ATG    1152
Ala Lys Met Thr Ala Thr Phe Leu Ser Lys Lys Gln Glu Val Asn Met
    370                 375                 380

TCC GAC TCT GCG CTG GAC TGT GTA CGT GAT GAG GCC ATA AAT AAG TTA    1200
Ser Asp Ser Ala Leu Asp Cys Val Arg Asp Glu Ala Ile Asn Lys Leu
385                 390                 395                 400

CAG CAG ATT TTC AAT ACT TCA TAC AAT CAA ACA TAT GAA AAA TAT GGA    1248
Gln Gln Ile Phe Asn Thr Ser Tyr Asn Gln Thr Tyr Glu Lys Tyr Gly
                405                 410                 415

AAC GTG TCC GTC TTT GAA ACC ACT GGT GGT TTG GTG GTG TTC TGG CAA    1296
Asn Val Ser Val Phe Glu Thr Thr Gly Gly Leu Val Val Phe Trp Gln
            420                 425                 430

GGT ATC AAG CAA AAA TCT CTG GTG GAA CTC GAA CGT TTG GCC AAC CGC    1344
Gly Ile Lys Gln Lys Ser Leu Val Glu Leu Glu Arg Leu Ala Asn Arg
        435                 440                 445

TCC AGT CTG AAT CTT ACT CAT AAT AGA ACC AAA AGA AGT ACA GAT GGC    1392
Ser Ser Leu Asn Leu Thr His Asn Arg Thr Lys Arg Ser Thr Asp Gly
    450                 455                 460

AAC AAT GCA ACT CAT TTA TCC AAC ATG GAG TCG GTG CAC AAT CTG GTC    1440
Asn Asn Ala Thr His Leu Ser Asn Met Glu Ser Val His Asn Leu Val
465                 470                 475                 480

TAC GCC CAG CTG CAG TTC ACC TAT GAC ACG TTG CGC GGT TAC ATC AAC    1488
Tyr Ala Gln Leu Gln Phe Thr Tyr Asp Thr Leu Arg Gly Tyr Ile Asn
                485                 490                 495

CGG GCG CTG GCG CAA ATC GCA GAA GCC TGG TGT GTG GAT CAA CGG CGC    1536
Arg Ala Leu Ala Gln Ile Ala Glu Ala Trp Cys Val Asp Gln Arg Arg
            500                 505                 510

ACC CTA GAG GTC TTC AAG GAA CTT AGC AAG ATC AAC CCG TCA GCT ATT    1584
Thr Leu Glu Val Phe Lys Glu Leu Ser Lys Ile Asn Pro Ser Ala Ile
        515                 520                 525

CTC TCG GCC ATC TAC AAC AAA CCG ATT GCC GCG CGT TTC ATG GGT GAT    1632
Leu Ser Ala Ile Tyr Asn Lys Pro Ile Ala Ala Arg Phe Met Gly Asp
    530                 535                 540

GTC CTG GGT CTG GCC AGC TGC GTG ACC ATT AAC CAA ACC AGC GTC AAG    1680
Val Leu Gly Leu Ala Ser Cys Val Thr Ile Asn Gln Thr Ser Val Lys
545                 550                 555                 560

GTG CTG CGT GAT ATG AAT GTG AAG GAA TCG CCA GGA CGC TGC TAC TCA    1728
Val Leu Arg Asp Met Asn Val Lys Glu Ser Pro Gly Arg Cys Tyr Ser
                565                 570                 575

CGA CCA GTG GTC ATC TTT AAT TTC GCC AAC AGC TCG TAC GTG CAG TAC    1776
Arg Pro Val Val Ile Phe Asn Phe Ala Asn Ser Ser Tyr Val Gln Tyr
            580                 585                 590

GGT CAA CTG GGC GAG GAT AAC GAA ATC CTG TTG GGC AAC CAC CGC ACT    1824
Gly Gln Leu Gly Glu Asp Asn Glu Ile Leu Leu Gly Asn His Arg Thr
        595                 600                 605

GAG GAA TGT CAG CTT CCC AGC CTC AAG ATC TTC ATC GCC GGC AAC TCG    1872
Glu Glu Cys Gln Leu Pro Ser Leu Lys Ile Phe Ile Ala Gly Asn Ser
    610                 615                 620

GCC TAC GAG TAC GTG GAC TAC CTC TTC AAA CGC ATG ATT GAC CTC AGC    1920
Ala Tyr Glu Tyr Val Asp Tyr Leu Phe Lys Arg Met Ile Asp Leu Ser
625                 630                 635                 640

AGC ATC TCC ACC GTC GAC AGC ATG ATC GCC CTA GAC ATC GAC CCG CTG    1968
Ser Ile Ser Thr Val Asp Ser Met Ile Ala Leu Asp Ile Asp Pro Leu
                645                 650                 655

GAA AAC ACC GAC TTC AGG GTA CTG GAA CTT TAC TCG CAG AAA GAA TTG    2016
Glu Asn Thr Asp Phe Arg Val Leu Glu Leu Tyr Ser Gln Lys Glu Leu
            660                 665                 670

CGT TCC AGC AAC GTT TTT GAT CTC GAG GAG ATC ATG CGC GAG TTC AAT    2064
Arg Ser Ser Asn Val Phe Asp Leu Glu Glu Ile Met Arg Glu Phe Asn
```

```
                675                 680                      685
TCG TAT AAG CAG CGG GTA AAG TAC GTG GAG GAC AAG GTA GTC GAC CCG      2112
Ser Tyr Lys Gln Arg Val Lys Tyr Val Glu Asp Lys Val Val Asp Pro
    690                 695                      700

CTG CCG CCC TAC CTC AAG GGT CTG GAC GAC CTC ATG AGC GGC CTG GGC      2160
Leu Pro Pro Tyr Leu Lys Gly Leu Asp Asp Leu Met Ser Gly Leu Gly
705                 710                      715                 720

GCC GCG GGA AAG GCC GTT GGC GTA GCC ATT GGG GCC GTG GGT GGC GCG      2208
Ala Ala Gly Lys Ala Val Gly Val Ala Ile Gly Ala Val Gly Gly Ala
                725                      730                 735

GTG GCC TCC GTG GTC GAA GGC GTT GCC ACC TTC CTC AAA AAC CCC TTC      2256
Val Ala Ser Val Val Glu Gly Val Ala Thr Phe Leu Lys Asn Pro Phe
                740                      745                 750

GGA GCC TTC ACC ATC ATC CTC GTG GCC ATA GCC GTC GTC ATT ATC ATT      2304
Gly Ala Phe Thr Ile Ile Leu Val Ala Ile Ala Val Val Ile Ile Ile
                755                      760                 765

TAT TTG ATC TAT ACT CGA CAG CGG CGT CTC TGC ATG CAG CCG CTG CAG      2352
Tyr Leu Ile Tyr Thr Arg Gln Arg Arg Leu Cys Met Gln Pro Leu Gln
            770                  775                 780

AAC CTC TTT CCC TAT CTG GTG TCC GCC GAC GGG ACC ACC GTG ACG TCG      2400
Asn Leu Phe Pro Tyr Leu Val Ser Ala Asp Gly Thr Thr Val Thr Ser
785                 790                      795                 800

GGC AAC ACC AAA GAC ACG TCG TTA CAG GCT CCG CCT TCC TAC GAG GAA      2448
Gly Asn Thr Lys Asp Thr Ser Leu Gln Ala Pro Pro Ser Tyr Glu Glu
                805                      810                 815

AGT GTT TAT AAT TCT GGT CGC AAA GGA CCG GGA CCA CCG TCG TCT GAT      2496
Ser Val Tyr Asn Ser Gly Arg Lys Gly Pro Gly Pro Pro Ser Ser Asp
                820                      825                 830

GCA TCC ACG GCG GCT CCG CCT TAC ACC AAC GAG CAG GCT TAC CAG ATG      2544
Ala Ser Thr Ala Ala Pro Pro Tyr Thr Asn Glu Gln Ala Tyr Gln Met
                835                      840                 845

CTT CTG GCC CTG GTC CGT CTG GAC GCA GAG CAG CGA GCG CAG CAG AAC      2592
Leu Leu Ala Leu Val Arg Leu Asp Ala Glu Gln Arg Ala Gln Gln Asn
850                 855                      860

GGT ACA GAT TCT TTG GAC GGA CAG ACT GGC ACG CAG GAC AAG GGA CAG      2640
Gly Thr Asp Ser Leu Asp Gly Gln Thr Gly Thr Gln Asp Lys Gly Gln
865                 870                      875                 880

AAG CCC AAC CTG CTA GAC CGA CTG CGA CAC CGC AAA AAC GGC TAC CGA      2688
Lys Pro Asn Leu Leu Asp Arg Leu Arg His Arg Lys Asn Gly Tyr Arg
                885                      890                 895

CAC TTG AAA GAC TCC GAC GAA GAA GAG AAC GTC TGA                      2724
His Leu Lys Asp Ser Asp Glu Glu Glu Asn Val
                900                      905

(2) INFORMATION FOR SEQ ID NO: 2:

(i) SEQUENCE CHARACTERISTICS:
        (A) LENGTH: 907 amino acids
        (B) TYPE: amino acid
        (D) TOPOLOGY: linear (ii) MOLECULE TYPE: protein (xi) SEQUENCE DESCRIPTION: SEQ ID NO: 2:

Met Glu Ser Arg Ile Trp Cys Leu Val Val Cys Val Asn Leu Cys Ile
1               5                   10                  15

Val Cys Leu Gly Ala Ala Val Ser Ser Ser Thr Arg Gly Thr Ser
            20                  25                  30

Ala Thr His Ser His His Ser Ser His Thr Thr Ser Ala Ala His Ser
        35                  40                  45
```

-continued

```
Arg Ser Gly Ser Val Ser Gln Arg Val Thr Ser Ser Gln Thr Val Ser
     50                  55                  60

His Gly Val Asn Glu Thr Ile Tyr Asn Thr Thr Leu Lys Tyr Gly Asp
 65                  70                  75                  80

Val Val Gly Val Asn Thr Thr Lys Tyr Pro Tyr Arg Val Cys Ser Met
                 85                  90                  95

Ala Gln Gly Thr Asp Leu Ile Arg Phe Glu Arg Asn Ile Val Cys Thr
                100                 105                 110

Ser Met Lys Pro Ile Asn Glu Asp Leu Asp Glu Gly Ile Met Val Val
            115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
        195                 200                 205

Lys Thr Met Gln Leu Met Pro Asp Asp Tyr Ser Asn Thr His Ser Thr
    210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Val Thr Ile Thr Thr
                245                 250                 255

Ala Arg Ser Lys Tyr Pro Tyr His Phe Phe Ala Thr Ser Thr Gly Asp
            260                 265                 270

Val Val Asp Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
    290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
    370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Thr Gly Gly Leu Val Val Phe Trp Gln
            420                 425                 430

Gly Ile Lys Gln Lys Ser Leu Val Glu Leu Glu Arg Leu Ala Asn Arg
        435                 440                 445

Ser Ser Leu Asn Leu Thr His Asn Arg Thr Lys Arg Ser Thr Asp Gly
450                 455                 460

Asn Asn Ala Thr His Leu Ser Asn Met Glu Ser Val His Asn Leu Val
```

-continued

```
465                 470                 475                 480
Tyr Ala Gln Leu Gln Phe Thr Tyr Asp Thr Leu Arg Gly Tyr Ile Asn
                    485                 490                 495
Arg Ala Leu Ala Gln Ile Ala Glu Ala Trp Cys Val Asp Gln Arg Arg
                500                 505                 510
Thr Leu Glu Val Phe Lys Glu Leu Ser Lys Ile Asn Pro Ser Ala Ile
            515                 520                 525
Leu Ser Ala Ile Tyr Asn Lys Pro Ile Ala Arg Phe Met Gly Asp
        530                 535                 540
Val Leu Gly Leu Ala Ser Cys Val Thr Ile Asn Gln Thr Ser Val Lys
545                 550                 555                 560
Val Leu Arg Asp Met Asn Val Lys Glu Ser Pro Gly Arg Cys Tyr Ser
                565                 570                 575
Arg Pro Val Val Ile Phe Asn Phe Ala Asn Ser Ser Tyr Val Gln Tyr
                580                 585                 590
Gly Gln Leu Gly Glu Asp Asn Glu Ile Leu Leu Gly Asn His Arg Thr
            595                 600                 605
Glu Glu Cys Gln Leu Pro Ser Leu Lys Ile Phe Ile Ala Gly Asn Ser
        610                 615                 620
Ala Tyr Glu Tyr Val Asp Tyr Leu Phe Lys Arg Met Ile Asp Leu Ser
625                 630                 635                 640
Ser Ile Ser Thr Val Asp Ser Met Ile Ala Leu Asp Ile Asp Pro Leu
                645                 650                 655
Glu Asn Thr Asp Phe Arg Val Leu Glu Leu Tyr Ser Gln Lys Glu Leu
                660                 665                 670
Arg Ser Ser Asn Val Phe Asp Leu Glu Glu Ile Met Arg Glu Phe Asn
            675                 680                 685
Ser Tyr Lys Gln Arg Val Lys Tyr Val Glu Asp Lys Val Val Asp Pro
        690                 695                 700
Leu Pro Pro Tyr Leu Lys Gly Leu Asp Asp Leu Met Ser Gly Leu Gly
705                 710                 715                 720
Ala Ala Gly Lys Ala Val Gly Val Ala Ile Gly Ala Val Gly Gly Ala
                725                 730                 735
Val Ala Ser Val Val Glu Gly Val Ala Thr Phe Leu Lys Asn Pro Phe
                740                 745                 750
Gly Ala Phe Thr Ile Ile Leu Val Ala Ile Ala Val Val Ile Ile Ile
            755                 760                 765
Tyr Leu Ile Tyr Thr Arg Gln Arg Arg Leu Cys Met Gln Pro Leu Gln
        770                 775                 780
Asn Leu Phe Pro Tyr Leu Val Ser Ala Asp Gly Thr Thr Val Thr Ser
785                 790                 795                 800
Gly Asn Thr Lys Asp Thr Ser Leu Gln Ala Pro Pro Ser Tyr Glu Glu
                805                 810                 815
Ser Val Tyr Asn Ser Gly Arg Lys Gly Pro Gly Pro Pro Ser Ser Asp
                820                 825                 830
Ala Ser Thr Ala Ala Pro Pro Tyr Thr Asn Glu Gln Ala Tyr Gln Met
            835                 840                 845
Leu Leu Ala Leu Val Arg Leu Asp Ala Glu Gln Arg Ala Gln Gln Asn
        850                 855                 860
Gly Thr Asp Ser Leu Asp Gly Gln Thr Gly Thr Gln Asp Lys Gly Gln
865                 870                 875                 880
Lys Pro Asn Leu Leu Asp Arg Leu Arg His Arg Lys Asn Gly Tyr Arg
                885                 890                 895
```

His Leu Lys Asp Ser Asp Glu Glu Glu Asn Val
            900                     905

(2) INFORMATION FOR SEQ ID NO: 3:

(i) SEQUENCE CHARACTERISTICS:
        (A) LENGTH: 1221 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..1218

(ix) FEATURE:
        (A) NAME/KEY: mat_peptide
        (B) LOCATION: 1

(xi) SEQUENCE DESCRIPTION: SEQ ID NO: 3:

```
ATG AAA CAG ATT AAG GTT CGA GTG GAC ATG CTG CGG CAT AGA ATC AAG         48
Met Lys Gln Ile Lys Val Arg Val Asp Met Leu Arg His Arg Ile Lys
  1               5                  10                  15

GAG CAC ATG CTG AAA AAA TAT ACC CAG ACG GAA GAG AAA TTC ACT GGC         96
Glu His Met Leu Lys Lys Tyr Thr Gln Thr Glu Glu Lys Phe Thr Gly
                 20                  25                  30

GCC TTT AAT ATG ATG GGA GGA TGT TTG CAG AAT GCC TTA GAT ATC TTA        144
Ala Phe Asn Met Met Gly Gly Cys Leu Gln Asn Ala Leu Asp Ile Leu
             35                  40                  45

GAT AAG GTT CAT GAG CCT TTC GAG GAG ATG AAG TGT ATT GGG CTA ACT        192
Asp Lys Val His Glu Pro Phe Glu Glu Met Lys Cys Ile Gly Leu Thr
 50                  55                  60

ATG CAG AGC ATG TAT GAG AAC TAC ATT GTA CCT GAG GAT AAG CGG GAG        240
Met Gln Ser Met Tyr Glu Asn Tyr Ile Val Pro Glu Asp Lys Arg Glu
 65                  70                  75                  80

ATG TGG ATG GCT TGT ATT AAG GAG CTG CAT GAT GTG AGC AAG GGC GCC        288
Met Trp Met Ala Cys Ile Lys Glu Leu His Asp Val Ser Lys Gly Ala
                 85                  90                  95

GCT AAC AAG TTG GGG GGT GCA CTG CAG GCT AAG GCC CGT GCT AAA AAG        336
Ala Asn Lys Leu Gly Gly Ala Leu Gln Ala Lys Ala Arg Ala Lys Lys
            100                 105                 110

GAT GAA CTT AGG AGA AAG ATG ATG TAT ATG TGC TAC AGG AAT ATA GAG        384
Asp Glu Leu Arg Arg Lys Met Met Tyr Met Cys Tyr Arg Asn Ile Glu
        115                 120                 125

TTC TTT ACC AAG AAC TCA GCC TTC CCT AAG ACC ACC AAT GGC TGC AGT        432
Phe Phe Thr Lys Asn Ser Ala Phe Pro Lys Thr Thr Asn Gly Cys Ser
    130                 135                 140

CAG GCC ATG GCG GCA TTG CAG AAC TTG CCT CAG TGC TCC CCT GAT GAG        480
Gln Ala Met Ala Ala Leu Gln Asn Leu Pro Gln Cys Ser Pro Asp Glu
145                 150                 155                 160

ATT ATG GCT TAT GCC CAG AAA ATA TTT AAG ATT TTG GAT GAG GAG AGA        528
Ile Met Ala Tyr Ala Gln Lys Ile Phe Lys Ile Leu Asp Glu Glu Arg
                165                 170                 175

GAC AAG GTG CTC ACG CAC ATT GAT CAC ATA TTT ATG GAT ATC CTC ACT        576
Asp Lys Val Leu Thr His Ile Asp His Ile Phe Met Asp Ile Leu Thr
            180                 185                 190

ACA TGT GTG GAA ACA ATG TGT AAT GAG TAC AAG GTC ACT AGT GAC GCT        624
Thr Cys Val Glu Thr Met Cys Asn Glu Tyr Lys Val Thr Ser Asp Ala
        195                 200                 205

TGT ATG ATG ACC ATG TAC GGG GGC ATC TCT CTC TTA AGT GAG TTC TGT        672
Cys Met Met Thr Met Tyr Gly Gly Ile Ser Leu Leu Ser Glu Phe Cys
```

```
                210                 215                 220
CGG GTG CTG TCC TGC TAT GTC TTA GAG GAG ACT AGT GTG ATG CTG GCC      720
Arg Val Leu Ser Cys Tyr Val Leu Glu Glu Thr Ser Val Met Leu Ala
225                 230                 235                 240

AAG CGG CCT CTG ATA ACC AAG CCT GAG GTT ATC AGT GTA ATG AAG CGC      768
Lys Arg Pro Leu Ile Thr Lys Pro Glu Val Ile Ser Val Met Lys Arg
                245                 250                 255

CGC ATT GAG GAG ATC TGC ATG AAG GTC TTT GCC CAG TAC ATT CTG GGG      816
Arg Ile Glu Glu Ile Cys Met Lys Val Phe Ala Gln Tyr Ile Leu Gly
                260                 265                 270

GCC GAT CCT CTG AGA GTC TGC TCT CCT AGT GTG GAT GAC CTA CGG GCC      864
Ala Asp Pro Leu Arg Val Cys Ser Pro Ser Val Asp Asp Leu Arg Ala
            275                 280                 285

ATC GCC GAG GAG TCA GAT GAG GAA GAG GCT ATT GTA GCC TAC ACT TTG      912
Ile Ala Glu Glu Ser Asp Glu Glu Glu Ala Ile Val Ala Tyr Thr Leu
        290                 295                 300

GCC ACC CGT GGT GCC AGC TCC TCT GAT TCT CTG GTG TCA CCC CCA GAG      960
Ala Thr Arg Gly Ala Ser Ser Ser Asp Ser Leu Val Ser Pro Pro Glu
305                 310                 315                 320

TCC CCT GTA CCC GCG ACT ATC CCT CTG TCC TCA GTA ATT GTG GCT GAG     1008
Ser Pro Val Pro Ala Thr Ile Pro Leu Ser Ser Val Ile Val Ala Glu
                325                 330                 335

AAC AGT GAT CAG GAA GAA AGT GAG CAG AGT GAT GAG GAA GAG GAG GAG     1056
Asn Ser Asp Gln Glu Glu Ser Glu Gln Ser Asp Glu Glu Glu Glu Glu
                340                 345                 350

GGT GCT CAG GAG GAG CGG GAG GAC ACT GTG TCT GTC AAG TCT GAG CCA     1104
Gly Ala Gln Glu Glu Arg Glu Asp Thr Val Ser Val Lys Ser Glu Pro
            355                 360                 365

GTG TCT GAG ATA GAG GAA GTT GCC CCA GAG GAA GAG GAG GAT GGT GCT     1152
Val Ser Glu Ile Glu Glu Val Ala Pro Glu Glu Glu Glu Asp Gly Ala
        370                 375                 380

GAG GAA CCC ACC GCC TCT GGA GGC AAG AGC ACC CAC CCT ATG GTG ACT     1200
Glu Glu Pro Thr Ala Ser Gly Gly Lys Ser Thr His Pro Met Val Thr
385                 390                 395                 400

AGA AGC AAG GCT GAC CAG TAA                                         1221
Arg Ser Lys Ala Asp Gln
                405
```

(2) INFORMATION FOR SEQ ID NO: 4:

(i) SEQUENCE CHARACTERISTICS:
        (A) LENGTH: 406 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Lys Gln Ile Lys Val Arg Val Asp Met Leu Arg His Arg Ile Lys
1               5                   10                  15

Glu His Met Leu Lys Lys Tyr Thr Gln Thr Glu Glu Lys Phe Thr Gly
                20                  25                  30

Ala Phe Asn Met Met Gly Gly Cys Leu Gln Asn Ala Leu Asp Ile Leu
            35                  40                  45

Asp Lys Val His Glu Pro Phe Glu Glu Met Lys Cys Ile Gly Leu Thr
        50                  55                  60

Met Gln Ser Met Tyr Glu Asn Tyr Ile Val Pro Glu Asp Lys Arg Glu
65                  70                  75                  80

Met Trp Met Ala Cys Ile Lys Glu Leu His Asp Val Ser Lys Gly Ala
                85                  90                  95
```

```
Ala Asn Lys Leu Gly Gly Ala Leu Gln Ala Lys Ala Arg Ala Lys Lys
            100                 105                 110

Asp Glu Leu Arg Arg Lys Met Met Tyr Met Cys Tyr Arg Asn Ile Glu
            115                 120                 125

Phe Phe Thr Lys Asn Ser Ala Phe Pro Lys Thr Thr Asn Gly Cys Ser
            130                 135                 140

Gln Ala Met Ala Ala Leu Gln Asn Leu Pro Gln Cys Ser Pro Asp Glu
145                 150                 155                 160

Ile Met Ala Tyr Ala Gln Lys Ile Phe Lys Ile Leu Asp Glu Glu Arg
                165                 170                 175

Asp Lys Val Leu Thr His Ile Asp His Ile Phe Met Asp Ile Leu Thr
            180                 185                 190

Thr Cys Val Glu Thr Met Cys Asn Glu Tyr Lys Val Thr Ser Asp Ala
            195                 200                 205

Cys Met Met Thr Met Tyr Gly Gly Ile Ser Leu Leu Ser Glu Phe Cys
            210                 215                 220

Arg Val Leu Ser Cys Tyr Val Leu Glu Glu Thr Ser Val Met Leu Ala
225                 230                 235                 240

Lys Arg Pro Leu Ile Thr Lys Pro Glu Val Ile Ser Val Met Lys Arg
                245                 250                 255

Arg Ile Glu Glu Ile Cys Met Lys Val Phe Ala Gln Tyr Ile Leu Gly
            260                 265                 270

Ala Asp Pro Leu Arg Val Cys Ser Pro Ser Val Asp Asp Leu Arg Ala
            275                 280                 285

Ile Ala Glu Glu Ser Asp Glu Glu Ala Ile Val Ala Tyr Thr Leu
290                 295                 300

Ala Thr Arg Gly Ala Ser Ser Ser Asp Ser Leu Val Ser Pro Pro Glu
305                 310                 315                 320

Ser Pro Val Pro Ala Thr Ile Pro Leu Ser Ser Val Ile Val Ala Glu
                325                 330                 335

Asn Ser Asp Gln Glu Glu Ser Gly Gln Ser Asp Glu Glu Glu Glu
            340                 345                 350

Gly Ala Gln Glu Glu Arg Glu Asp Thr Val Ser Val Lys Ser Glu Pro
            355                 360                 365

Val Ser Glu Ile Glu Glu Val Ala Pro Glu Glu Glu Asp Gly Ala
370                 375                 380

Glu Glu Pro Thr Ala Ser Gly Gly Lys Ser Thr His Pro Met Val Thr
385                 390                 395                 400

Arg Ser Lys Ala Asp Gln
                405

(2) INFORMATION FOR SEQ ID NO: 5:

(i) SEQUENCE CHARACTERISTICS:
        (A) LENGTH: 1932 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: mat_peptide
        (B) LOCATION: 4

(ix) FEATURE:
        (A) NAME/KEY: CDS
        (B) LOCATION: join(4..1656, 1847..1930)
```

(xi) SEQUENCE DESCRIPTION: SEQ ID NO: 5:

```
GCC ATG GCA TCC GTA CTG GGT CCC ATT TCG GGG CAC GTG CTG AAA GCC         48
    Met Ala Ser Val Leu Gly Pro Ile Ser Gly His Val Leu Lys Ala
    1               5                  10                  15

GTG TTT AGT CGC GGC GAC ACG CCG GTG CTG CCG CAC GAG ACG CGA CTC         96
Val Phe Ser Arg Gly Asp Thr Pro Val Leu Pro His Glu Thr Arg Leu
                    20                  25                  30

CTG CAG ACG GGT ATC CAC GTG CGC GTG AGC CAG CCC TCG CTG ATC CTG        144
Leu Gln Thr Gly Ile His Val Arg Val Ser Gln Pro Ser Leu Ile Leu
                35                  40                  45

GTG TCG CAG TAC ACG CCC GAC TCG ACG CCA TGC CAC CGC GGC GAC AAT        192
Val Ser Gln Tyr Thr Pro Asp Ser Thr Pro Cys His Arg Gly Asp Asn
            50                  55                  60

CAG CTG CAG GTG CAG CAC ACG TAC TTT ACG GGC AGC GAG GTG GAG AAC        240
Gln Leu Gln Val Gln His Thr Tyr Phe Thr Gly Ser Glu Val Glu Asn
65                  70                  75

GTG TCG GTC AAC GTG CAC AAC CCC ACG GGC CGG AGC ATC TGC CCC AGC        288
Val Ser Val Asn Val His Asn Pro Thr Gly Arg Ser Ile Cys Pro Ser
80                  85                  90                  95

CAA GAG CCC ATG TCG ATC TAT GTG TAC GCG CTG CCG CTC AAG ATG CTG        336
Gln Glu Pro Met Ser Ile Tyr Val Tyr Ala Leu Pro Leu Lys Met Leu
                100                 105                 110

AAC ATC CCC AGC ATC AAC GTG CAC CAC TAC CCG TCG GCG GCC GAG CGC        384
Asn Ile Pro Ser Ile Asn Val His His Tyr Pro Ser Ala Ala Glu Arg
                115                 120                 125

AAA CAC CGA CAC CTG CCC GTA GCT GAC GCT GTG ATT CAC GCG TCG GGC        432
Lys His Arg His Leu Pro Val Ala Asp Ala Val Ile His Ala Ser Gly
                130                 135                 140

AAG CAG ATG TGG CAG GCG CGT CTC ACG GTC TCG GGA CTG GCC TGG ACG        480
Lys Gln Met Trp Gln Ala Arg Leu Thr Val Ser Gly Leu Ala Trp Thr
145                 150                 155

CGT CAG CAG AAC CAG TGG AAA GAG CCC GAC GTC TAC TAC ACG TCA GCG        528
Arg Gln Gln Asn Gln Trp Lys Glu Pro Asp Val Tyr Tyr Thr Ser Ala
160                 165                 170                 175

TTC GTG TTT CCC ACC AAG GAC GTG GCA CTG CGG CAC GTG GTG TGC GCG        576
Phe Val Phe Pro Thr Lys Asp Val Ala Leu Arg His Val Val Cys Ala
                180                 185                 190

CAC GAG CTG GTT TGC TCC ATG GAG AAC ACG CGC GCA ACC AAG ATG CAG        624
His Glu Leu Val Cys Ser Met Glu Asn Thr Arg Ala Thr Lys Met Gln
                195                 200                 205

GTG ATA GGT GAC CAG TAC GTC AAG GTG TAC CTG GAG TCC TTC TGC GAG        672
Val Ile Gly Asp Gln Tyr Val Lys Val Tyr Leu Glu Ser Phe Cys Glu
                210                 215                 220

GAC GTG CCC TCC GGC AAG CTC TTT ATG CAC GTC ACG CTG GGC TCT GAC        720
Asp Val Pro Ser Gly Lys Leu Phe Met His Val Thr Leu Gly Ser Asp
225                 230                 235

GTG GAA GAG GAC CTG ACG ATG ACC CGC AAC CCG CAA CCC TTC ATG CGC        768
Val Glu Glu Asp Leu Thr Met Thr Arg Asn Pro Gln Pro Phe Met Arg
240                 245                 250                 255

CCC CAC GAG CGC AAC GGC TTT ACG GTG TTG TGT CCC AAA AAT ATG ATA        816
Pro His Glu Arg Asn Gly Phe Thr Val Leu Cys Pro Lys Asn Met Ile
                260                 265                 270

ATC AAA CCG GGC AAG ATC TCG CAC ATC ATG CTG GAT GTG GCT TTT ACC        864
Ile Lys Pro Gly Lys Ile Ser His Ile Met Leu Asp Val Ala Phe Thr
                275                 280                 285

TCA CAC GAG CAT TTT GGG CTG CTG TGT CCC AAG AGC ATC CCG GGC CTG        912
Ser His Glu His Phe Gly Leu Leu Cys Pro Lys Ser Ile Pro Gly Leu
                290                 295                 300
```

```
AGC ATC TCA GGT AAC CTA TTG ATG AAC GGG CAG CAG ATC TTC CTG GAG        960
Ser Ile Ser Gly Asn Leu Leu Met Asn Gly Gln Gln Ile Phe Leu Glu
    305                 310                 315

GTG CAA GCG ATA CGC GAG ACC GTG GAA CTG CGT CAG TAC GAT CCC GTG       1008
Val Gln Ala Ile Arg Glu Thr Val Glu Leu Arg Gln Tyr Asp Pro Val
320                 325                 330                 335

GCT GCG CTC TTC TTT TTC GAT ATC GAC TTG CTG CTG CAG CGC GGG CCT      1056
Ala Ala Leu Phe Phe Phe Asp Ile Asp Leu Leu Leu Gln Arg Gly Pro
                340                 345                 350

CAG TAC AGC GAA CAC CCC ACC TTC ACC AGC CAG TAT CGC ATC CAG GGC      1104
Gln Tyr Ser Glu His Pro Thr Phe Thr Ser Gln Tyr Arg Ile Gln Gly
            355                 360                 365

AAG CTT GAG TAC CGA CAC ACC TGG GAC CGG CAC GAC GAG GGT GCC GCC      1152
Lys Leu Glu Tyr Arg His Thr Trp Asp Arg His Asp Glu Gly Ala Ala
        370                 375                 380

CAG GGC GAC GAC GAC GTC TGG ACC AGC GGA TCG GAC TCC GAC GAG GAA      1200
Gln Gly Asp Asp Asp Val Trp Thr Ser Gly Ser Asp Ser Asp Glu Glu
385                 390                 395

CTC GTA ACC ACC GAG CGC AAG ACG CCC CGC GTT ACC GGC GGC GGC GCC      1248
Leu Val Thr Thr Glu Arg Lys Thr Pro Arg Val Thr Gly Gly Gly Ala
400                 405                 410                 415

ATG GCG GGC GCC TCC ACT TCC GCG GGC CGC AAA CGC AAA TCA GCA TCC      1296
Met Ala Gly Ala Ser Thr Ser Ala Gly Arg Lys Arg Lys Ser Ala Ser
                420                 425                 430

TCG GCG ACG GCG TGC ACG GCG GGC GTT ATG ACA CGC GGC CGC CTT AAG      1344
Ser Ala Thr Ala Cys Thr Ala Gly Val Met Thr Arg Gly Arg Leu Lys
            435                 440                 445

GCC GAG TCC ACC GTC GCG CCC GAA GAG GAC ACC GAC GAG GAT TCC GAC      1392
Ala Glu Ser Thr Val Ala Pro Glu Glu Asp Thr Asp Glu Asp Ser Asp
        450                 455                 460

AAC GAA ATC CAC AAT CCG GCC GTG TTC ACC TGG CCG CCC TGG CAG GCC      1440
Asn Glu Ile His Asn Pro Ala Val Phe Thr Trp Pro Pro Trp Gln Ala
465                 470                 475

GGC ATC CTG GCC CGC AAC CTG GTG CCC ATG GTT GCT ACG GTT CAG GGT      1488
Gly Ile Leu Ala Arg Asn Leu Val Pro Met Val Ala Thr Val Gln Gly
480                 485                 490                 495

CAG AAT CTG AAG TAC CAG GAG TTC TTC TGG GAC GCC AAC GAC ATC TAC      1536
Gln Asn Leu Lys Tyr Gln Glu Phe Phe Trp Asp Ala Asn Asp Ile Tyr
                500                 505                 510

CGC ATC TTC GCC GAA TTG GAA GGC GTA TGG CAG CCC GCT GCG CAA CCC      1584
Arg Ile Phe Ala Glu Leu Glu Gly Val Trp Gln Pro Ala Ala Gln Pro
            515                 520                 525

AAA CGT CGC CGC CAC CGG CAA GAC GCC TTG CCC GGG CCA TGC ATC GCC      1632
Lys Arg Arg Arg His Arg Gln Asp Ala Leu Pro Gly Pro Cys Ile Ala
        530                 535                 540

TCG ACG CCC AAA AAG CAC CGA GGT TGAGCCACCC GCCGCGCACG CTTAGGACGA     1686
Ser Thr Pro Lys Lys His Arg Gly
    545                 550

CTCTATAAAA ACCCACGTCC ACTCAGACAC GCGACTTTTG GCCGCCACAC CTGTCGCCGC    1746

TGCTATATTT GCGACAGTTG CCGGAACCCT TCCCGACCTC CCACGAAGAC CCGTTCACCT    1806

TTGCGCATCC CCTGACCCCC CCCCTCATCC CGCCTTCGCG ATG TCT CAG GCA TCG     1861
                                             Met Ser Gln Ala Ser
                                                             555

TCC TCG CCC GGT GAG GGA CCC TCG TCG GAA GCG GCC GCG ATC AGC GAG     1909
Ser Ser Pro Gly Glu Gly Pro Ser Ser Glu Ala Ala Ala Ile Ser Glu
                560                 565                 570

GCC GAA GCC GCC AGC GGA AGC TT                                        1932
Ala Glu Ala Ala Ser Gly Ser
            575
```

(2) INFORMATION FOR SEQ ID NO: 6:

(i) SEQUENCE CHARACTERISTICS:
       (A) LENGTH: 579 amino acids
       (B) TYPE: amino acid
       (D) TOPOLOGY: linear (ii) MOLECULE TYPE: protein (xi) SEQUENCE DESCRIPTION: SEQ ID NO: 6:

```
Met Ala Ser Val Leu Gly Pro Ile Ser Gly His Val Leu Lys Ala Val
 1               5                  10                  15

Phe Ser Arg Gly Asp Thr Pro Val Leu Pro His Glu Thr Arg Leu Leu
             20                  25                  30

Gln Thr Gly Ile His Val Arg Val Ser Gln Pro Ser Leu Ile Leu Val
         35                  40                  45

Ser Gln Tyr Thr Pro Asp Ser Thr Pro Cys His Arg Gly Asp Asn Gln
     50                  55                  60

Leu Gln Val Gln His Thr Tyr Phe Thr Gly Ser Glu Val Glu Asn Val
 65                  70                  75                  80

Ser Val Asn Val His Asn Pro Thr Gly Arg Ser Ile Cys Pro Ser Gln
                 85                  90                  95

Glu Pro Met Ser Ile Tyr Val Tyr Ala Leu Pro Leu Lys Met Leu Asn
            100                 105                 110

Ile Pro Ser Ile Asn Val His His Tyr Pro Ser Ala Ala Glu Arg Lys
        115                 120                 125

His Arg His Leu Pro Val Ala Asp Ala Val Ile His Ala Ser Gly Lys
    130                 135                 140

Gln Met Trp Gln Ala Arg Leu Thr Val Ser Gly Leu Ala Trp Thr Arg
145                 150                 155                 160

Gln Gln Asn Gln Trp Lys Glu Pro Asp Val Tyr Tyr Thr Ser Ala Phe
                165                 170                 175

Val Phe Pro Thr Lys Asp Val Ala Leu Arg His Val Val Cys Ala His
            180                 185                 190

Glu Leu Val Cys Ser Met Glu Asn Thr Arg Ala Thr Lys Met Gln Val
        195                 200                 205

Ile Gly Asp Gln Tyr Val Lys Val Tyr Leu Glu Ser Phe Cys Glu Asp
    210                 215                 220

Val Pro Ser Gly Lys Leu Phe Met His Val Thr Leu Gly Ser Asp Val
225                 230                 235                 240

Glu Glu Asp Leu Thr Met Thr Arg Asn Pro Gln Pro Phe Met Arg Pro
                245                 250                 255

His Glu Arg Asn Gly Phe Thr Val Leu Cys Pro Lys Asn Met Ile Ile
            260                 265                 270

Lys Pro Gly Lys Ile Ser His Ile Met Leu Asp Val Ala Phe Thr Ser
        275                 280                 285

His Glu His Phe Gly Leu Leu Cys Pro Lys Ser Ile Pro Gly Leu Ser
    290                 295                 300

Ile Ser Gly Asn Leu Leu Met Asn Gly Gln Gln Ile Phe Leu Glu Val
305                 310                 315                 320

Gln Ala Ile Arg Glu Thr Val Glu Leu Arg Gln Tyr Asp Pro Val Ala
                325                 330                 335

Ala Leu Phe Phe Phe Asp Ile Asp Leu Leu Leu Gln Arg Gly Pro Gln
            340                 345                 350
```

-continued

```
Tyr Ser Glu His Pro Thr Phe Thr Ser Gln Tyr Arg Ile Gln Gly Lys
        355                 360                 365

Leu Glu Tyr Arg His Thr Trp Asp Arg His Asp Glu Gly Ala Ala Gln
    370                 375                 380

Gly Asp Asp Asp Val Trp Thr Ser Gly Ser Asp Ser Asp Glu Glu Leu
385                 390                 395                 400

Val Thr Thr Glu Arg Lys Thr Pro Arg Val Thr Gly Gly Gly Ala Met
                405                 410                 415

Ala Gly Ala Ser Thr Ser Ala Gly Arg Lys Arg Lys Ser Ala Ser Ser
            420                 425                 430

Ala Thr Ala Cys Thr Ala Gly Val Met Thr Arg Gly Arg Leu Lys Ala
        435                 440                 445

Glu Ser Thr Val Ala Pro Glu Glu Asp Thr Asp Glu Asp Ser Asp Asn
    450                 455                 460

Glu Ile His Asn Pro Ala Val Phe Thr Trp Pro Pro Trp Gln Ala Gly
465                 470                 475                 480

Ile Leu Ala Arg Asn Leu Val Pro Met Val Ala Thr Val Gln Gly Gln
                485                 490                 495

Asn Leu Lys Tyr Gln Glu Phe Phe Trp Asp Ala Asn Asp Ile Tyr Arg
            500                 505                 510

Ile Phe Ala Glu Leu Glu Gly Val Trp Gln Pro Ala Ala Gln Pro Lys
        515                 520                 525

Arg Arg Arg His Arg Gln Asp Ala Leu Pro Gly Pro Cys Ile Ala Ser
    530                 535                 540

Thr Pro Lys Lys His Arg Gly Met Ser Gln Ala Ser Ser Ser Pro Gly
545                 550                 555                 560

Glu Gly Pro Ser Ser Glu Ala Ala Ile Ser Glu Ala Glu Ala Ala Ala
                565                 570                 575

Ser Gly Ser
```

(2) INFORMATION FOR SEQ ID NO: 7:

(i) SEQUENCE CHARACTERISTICS:
  (A) LENGTH: 1932 base pairs
  (B) TYPE: nucleic acid
  (C) STRANDEDNESS: double
  (D) TOPOLOGY: unknown (ii) MOLECULE TYPE: cDNA (ix) FEATURE:
  (A) NAME/KEY: mat_peptide
  (B) LOCATION: 4

(ix) FEATURE:
  (A) NAME/KEY: CDS
  (B) LOCATION: join(4..1656, 1847..1930)

(xi) SEQUENCE DESCRIPTION: SEQ ID NO: 7:

```
GCC ATG ATA TCC GTA CTG GGT CCC ATT TCG GGG CAC GTG CTG AAA GCC      48
    Met Ile Ser Val Leu Gly Pro Ile Ser Gly His Val Leu Lys Ala
    1               5                  10                  15

GTG TTT AGT CGC GGC GAT ACG CCG GTG CTG CCG CAC GAG ACG CGA CTC      96
Val Phe Ser Arg Gly Asp Thr Pro Val Leu Pro His Glu Thr Arg Leu
            20                  25                  30

CTG CAG ACG GGT ATC CAC GTA CGC GTG AGC CAG CCC TCG CTG ATC TTG     144
Leu Gln Thr Gly Ile His Val Arg Val Ser Gln Pro Ser Leu Ile Leu
        35                  40                  45

GTA TCG CAG TAC ACG CCC GAC TCG ACG CCA TGC CAC CGC GGC GAC AAT     192
Val Ser Gln Tyr Thr Pro Asp Ser Thr Pro Cys His Arg Gly Asp Asn
```

-continued

```
                50                      55                      60
CAG CTG CAG GTG CAG CAC ACG TAC TTT ACG GGC AGC GAG GTG GAG AAC      240
Gln Leu Gln Val Gln His Thr Tyr Phe Thr Gly Ser Glu Val Glu Asn
     65                      70                      75

GTG TCG GTC AAC GTG CAC AAC CCC ACG GGC CGA AGC ATC TGC CCC AGC     288
Val Ser Val Asn Val His Asn Pro Thr Gly Arg Ser Ile Cys Pro Ser
 80                      85                      90                  95

CAG GAG CCC ATG TCG ATC TAT GTG TAC GCG CTG CCG CTC AAG ATG CTG     336
Gln Glu Pro Met Ser Ile Tyr Val Tyr Ala Leu Pro Leu Lys Met Leu
                    100                     105                     110

AAC ATC CCC AGC ATC AAC GTG CAC CAC TAC CCG TCG GCG GCC GAG CGC     384
Asn Ile Pro Ser Ile Asn Val His His Tyr Pro Ser Ala Ala Glu Arg
             115                     120                     125

AAA CAC CGA CAC CTG CCC GTA GCT GAC GCT GTG ATT CAC GCG TCG GGC     432
Lys His Arg His Leu Pro Val Ala Asp Ala Val Ile His Ala Ser Gly
         130                     135                     140

AAG CAG ATG TGG CAG GCG CGT CTC ACG GTC TCG GGA CTG GCC TGG ACG     480
Lys Gln Met Trp Gln Ala Arg Leu Thr Val Ser Gly Leu Ala Trp Thr
 145                     150                     155

CGT CAG CAG AAC CAG TGG AAA GAG CCC GAC GTC TAC TAC ACG TCA GCG     528
Arg Gln Gln Asn Gln Trp Lys Glu Pro Asp Val Tyr Tyr Thr Ser Ala
160                     165                     170                 175

TTC GTG TTT CCC ACC AAG GAC GTG GCA CTG CGG CAC GTG GTG TGC GCG     576
Phe Val Phe Pro Thr Lys Asp Val Ala Leu Arg His Val Val Cys Ala
                    180                     185                     190

CAC GAG CTG GTT TGC TCC ATG GAG AAC ACG CGC GCA ACC AAG ATG CAG     624
His Glu Leu Val Cys Ser Met Glu Asn Thr Arg Ala Thr Lys Met Gln
             195                     200                     205

GTG ATA GGT GAC CAG TAC GTC AAG GTG TAC CTG GAG TCC TTC TGC GAG     672
Val Ile Gly Asp Gln Tyr Val Lys Val Tyr Leu Glu Ser Phe Cys Glu
         210                     215                     220

GAC GTG CCC TCC GGC AAG CTC TTT ATG CAC GTC ACG CTG GGC TCT GAC     720
Asp Val Pro Ser Gly Lys Leu Phe Met His Val Thr Leu Gly Ser Asp
 225                     230                     235

GTG GAA GAG GAC CTG ACG ATG ACC CGC AAC CCG CAA CCC TTC ATG CGC     768
Val Glu Glu Asp Leu Thr Met Thr Arg Asn Pro Gln Pro Phe Met Arg
240                     245                     250                 255

CCC CAC GAG CGC AAC GGC TTT ACG GTG TTG TGT CCC AAA AAT ATG ATA     816
Pro His Glu Arg Asn Gly Phe Thr Val Leu Cys Pro Lys Asn Met Ile
                    260                     265                     270

ATC AAA CCG GGC AAG ATC TCG CAC ATC ATG CTG GAT GTG GCT TTT ACC     864
Ile Lys Pro Gly Lys Ile Ser His Ile Met Leu Asp Val Ala Phe Thr
             275                     280                     285

TCA CAC GAG CAT TTT GGG CTG CTG TGT CCC AAG AGC ATC CCG GGC CTG     912
Ser His Glu His Phe Gly Leu Leu Cys Pro Lys Ser Ile Pro Gly Leu
         290                     295                     300

AGC ATC TCA GGT AAC CTG TTG ATG AAC GGG CAG CAG ATC TTC CTG GAG     960
Ser Ile Ser Gly Asn Leu Leu Met Asn Gly Gln Gln Ile Phe Leu Glu
 305                     310                     315

GTA CAA GCC ATA CGC GAG ACC GTG GAA CTG CGT CAG TAC GAT CCC GTG    1008
Val Gln Ala Ile Arg Glu Thr Val Glu Leu Arg Gln Tyr Asp Pro Val
320                     325                     330                 335

GCT GCG CTC TTC TTT TTC GAT ATC GAC TTG CTG CTG CAG CGC GGG CCT    1056
Ala Ala Leu Phe Phe Phe Asp Ile Asp Leu Leu Leu Gln Arg Gly Pro
                    340                     345                     350

CAG TAC AGC GAG CAC CCC ACC TTC ACC AGC CAG TAT CGC ATC CAG GGC    1104
Gln Tyr Ser Glu His Pro Thr Phe Thr Ser Gln Tyr Arg Ile Gln Gly
             355                     360                     365

AAG CTT GAG TAC CGA CAC ACC TGG GAC CGG CAC GAC GAG GGT GCC GCC    1152
```

```
Lys Leu Glu Tyr Arg His Thr Trp Asp Arg His Asp Glu Gly Ala Ala
            370                 375                 380

CAG GGC GAC GAC GAC GTC TGG ACC AGC GGA TCG GAC TCC GAC GAA GAA      1200
Gln Gly Asp Asp Asp Val Trp Thr Ser Gly Ser Asp Ser Asp Glu Glu
        385                 390                 395

CTC GTA ACC ACC GAG CGC AAG ACG CCC CGC GTC ACC GGC GGC GGC GCC      1248
Leu Val Thr Thr Glu Arg Lys Thr Pro Arg Val Thr Gly Gly Gly Ala
400                 405                 410                 415

ATG GCG GGC GCC TCC ACT TCC GCG GGC CGC AAA CGC AAA TCA GCA TCC      1296
Met Ala Gly Ala Ser Thr Ser Ala Gly Arg Lys Arg Lys Ser Ala Ser
                420                 425                 430

TCG GCG ACG GCG TGC ACG TCG GGC GTT ATG ACA CGC GGC CGC CTT AAG      1344
Ser Ala Thr Ala Cys Thr Ser Gly Val Met Thr Arg Gly Arg Leu Lys
            435                 440                 445

GCC GAG TCC ACC GTC GCG CCC GAA GAG GAC ACC GAC GAG GAT TCC GAC      1392
Ala Glu Ser Thr Val Ala Pro Glu Glu Asp Thr Asp Glu Asp Ser Asp
        450                 455                 460

AAC GAA ATC CAC AAT CCG GCC GTG TTC ACC TGG CCG CCC TGG CAG GCC      1440
Asn Glu Ile His Asn Pro Ala Val Phe Thr Trp Pro Pro Trp Gln Ala
    465                 470                 475

GGC ATC CTG GCC CGC AAC CTG GTG CCC ATG GTT GCT ACG GTT CAG GGT      1488
Gly Ile Leu Ala Arg Asn Leu Val Pro Met Val Ala Thr Val Gln Gly
480                 485                 490                 495

CAG AAT CTG AAG TAC CAG GAA TTC TTC TGG GAC GCC AAC GAC ATC TAC      1536
Gln Asn Leu Lys Tyr Gln Glu Phe Phe Trp Asp Ala Asn Asp Ile Tyr
                500                 505                 510

CGC ATC TTC GCC GAA TTG GAA GGC GTA TGG CAG CCC GCT GCG CAA CCC      1584
Arg Ile Phe Ala Glu Leu Glu Gly Val Trp Gln Pro Ala Ala Gln Pro
            515                 520                 525

AAA CGT CGC CGC CAC CGG CAA GAC GCC TTG CCC GGG CCA TGC ATC GCC      1632
Lys Arg Arg Arg His Arg Gln Asp Ala Leu Pro Gly Pro Cys Ile Ala
        530                 535                 540

TCG ACG CCC AAA AAG CAC CGA GGT TGAGCCACCC GCCGCACGCG CTTAGGACGA     1686
Ser Thr Pro Lys Lys His Arg Gly
    545                 550

CTCTATAAAA ACCCACGTCC ACTCAGACAC GCAACTTTTG GCCGCCACAC CTGTCACCGC    1746

TGCTATATTT GCGACAGTTG CCGGAACCCT TCCCGACCTC CCACGAAGAC CCGTTCACCT    1806

TTGCGCATCC CCTGACCCTC CCCCCCATCC CGCCTTCGCA ATG TCT CAG GCA TCG     1861
                                            Met Ser Gln Ala Ser
                                                            555

TCC TCG CCC GGT GAG GGA CCC TCG TCG GAA GCG GCC GCG ATC AGC GAG      1909
Ser Ser Pro Gly Glu Gly Pro Ser Ser Glu Ala Ala Ala Ile Ser Glu
                560                 565                 570

GCC GAA GCC GCC AGC GGA AGC TT                                       1932
Ala Glu Ala Ala Ser Gly Ser
        575

(2) INFORMATION FOR SEQ ID NO: 8:

(i) SEQUENCE CHARACTERISTICS:
        (A) LENGTH: 579 amino acids
        (B) TYPE: amino acid
        (D) TOPOLOGY: linear (ii) MOLECULE TYPE: protein (xi) SEQUENCE DESCRIPTION: SEQ ID NO: 8:

Met Ile Ser Val Leu Gly Pro Ile Ser Gly His Val Leu Lys Ala Val
 1               5                  10                  15

Phe Ser Arg Gly Asp Thr Pro Val Leu Pro His Glu Thr Arg Leu Leu
```

```
                    20                  25                  30
Gln Thr Gly Ile His Val Arg Val Ser Gln Pro Ser Leu Ile Leu Val
                35                  40                  45
Ser Gln Tyr Thr Pro Asp Ser Thr Pro Cys His Arg Gly Asp Asn Gln
 50                  55                  60
Leu Gln Val Gln His Thr Tyr Phe Thr Gly Ser Glu Val Glu Asn Val
 65                  70                  75                  80
Ser Val Asn Val His Asn Pro Thr Gly Arg Ser Ile Cys Pro Ser Gln
                 85                  90                  95
Glu Pro Met Ser Ile Tyr Val Tyr Ala Leu Pro Leu Lys Met Leu Asn
                100                 105                 110
Ile Pro Ser Ile Asn Val His His Tyr Pro Ser Ala Ala Glu Arg Lys
                115                 120                 125
His Arg His Leu Pro Val Ala Asp Ala Val Ile His Ala Ser Gly Lys
                130                 135                 140
Gln Met Trp Gln Ala Arg Leu Thr Val Ser Gly Leu Ala Trp Thr Arg
145                 150                 155                 160
Gln Gln Asn Gln Trp Lys Glu Pro Asp Val Tyr Tyr Thr Ser Ala Phe
                165                 170                 175
Val Phe Pro Thr Lys Asp Val Ala Leu Arg His Val Val Cys Ala His
                180                 185                 190
Glu Leu Val Cys Ser Met Glu Asn Thr Arg Ala Thr Lys Met Gln Val
                195                 200                 205
Ile Gly Asp Gln Tyr Val Lys Val Tyr Leu Glu Ser Phe Cys Glu Asp
                210                 215                 220
Val Pro Ser Gly Lys Leu Phe Met His Val Thr Leu Gly Ser Asp Val
225                 230                 235                 240
Glu Glu Asp Leu Thr Met Thr Arg Asn Pro Gln Pro Phe Met Arg Pro
                245                 250                 255
His Glu Arg Asn Gly Phe Thr Val Leu Cys Pro Lys Asn Met Ile Ile
                260                 265                 270
Lys Pro Gly Lys Ile Ser His Ile Met Leu Asp Val Ala Phe Thr Ser
                275                 280                 285
His Glu His Phe Gly Leu Leu Cys Pro Lys Ser Ile Pro Gly Leu Ser
                290                 295                 300
Ile Ser Gly Asn Leu Leu Met Asn Gly Gln Gln Ile Phe Leu Glu Val
305                 310                 315                 320
Gln Ala Ile Arg Glu Thr Val Glu Leu Arg Gln Tyr Asp Pro Val Ala
                325                 330                 335
Ala Leu Phe Phe Phe Asp Ile Asp Leu Leu Leu Gln Arg Gly Pro Gln
                340                 345                 350
Tyr Ser Glu His Pro Thr Phe Thr Ser Gln Tyr Arg Ile Gln Gly Lys
                355                 360                 365
Leu Glu Tyr Arg His Thr Trp Asp Arg His Asp Glu Gly Ala Ala Gln
                370                 375                 380
Gly Asp Asp Asp Val Trp Thr Ser Gly Ser Asp Ser Asp Glu Glu Leu
385                 390                 395                 400
Val Thr Thr Glu Arg Lys Thr Pro Arg Val Thr Gly Gly Gly Ala Met
                405                 410                 415
Ala Gly Ala Ser Thr Ser Ala Gly Arg Lys Arg Lys Ser Ala Ser Ser
                420                 425                 430
Ala Thr Ala Cys Thr Ser Gly Val Met Thr Arg Gly Arg Leu Lys Ala
                435                 440                 445
```

```
Glu Ser Thr Val Ala Pro Glu Glu Asp Thr Asp Glu Asp Ser Asp Asn
          450                 455                 460

Glu Ile His Asn Pro Ala Val Phe Thr Trp Pro Pro Trp Gln Ala Gly
465                 470                 475                 480

Ile Leu Ala Arg Asn Leu Val Pro Met Val Ala Thr Val Gln Gly Gln
                485                 490                 495

Asn Leu Lys Tyr Gln Glu Phe Phe Trp Asp Ala Asn Asp Ile Tyr Arg
            500                 505                 510

Ile Phe Ala Glu Leu Gly Val Trp Gln Pro Ala Ala Gln Pro Lys
            515                 520                 525

Arg Arg Arg His Arg Gln Asp Ala Leu Pro Gly Pro Cys Ile Ala Ser
530                 535                 540

Thr Pro Lys Lys His Arg Gly Met Ser Gln Ala Ser Ser Pro Gly
545                 550                 555                 560

Glu Gly Pro Ser Ser Glu Ala Ala Ile Ser Glu Ala Glu Ala Ala
                565                 570                 575

Ser Gly Ser
```

(2) INFORMATION FOR SEQ ID NO: 9:

(i) SEQUENCE CHARACTERISTICS:
        (A) LENGTH: 6360 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 524..3667

(ix) FEATURE:
        (A) NAME/KEY: mat_peptide
        (B) LOCATION: 524

(xi) SEQUENCE DESCRIPTION: SEQ ID NO: 9:

```
TAGATCACCG ATAGAAATTT ACACGAGGCC ACGCCGGCCG GCAACAGCCA CTGGTTGCTG      60

AGTACGATAA AGGGTAGCAC AGTAAGCGTG AGAAAATTAG TAGAGTAGAG GTTGGTCATG     120

TAAATGGTGG GCGTCGAATA GCCAAGCACG CGATTCGTGA GCAGCTGCGT GATCAACACT     180

ATGGCGTTAA GTGGACCGCC CACGAAGATG ATGAATGTGT TGAGTACGGC TTCGGTGGTT     240

CGAATGGCGA ATAGCGGCCC TGTCATGTTG CAAGTGTCAT TGATGTGCGG AGGAGTGTTG     300

TTGCGGGTCT GGGCGGAACA GCACACGGGG CGAAAAAACA GAAGAAACAA GTCAGCGGCG     360

CTTAAAAGAA AACCGCGTAT CCGCCTCCGC TATTAAACTA CCCCCCCTCC CTCTAGGTGG     420

GGCGCTCACC GAGTTGTGGA TGATGGTGTC CATCGTGGGC GAATAGCAGA CCGCGGGCGC     480

AGTCCGGGGC GACGACGCTT CCGGGTTCTG GAGAAAAGCC AGC ATG AGT TTG CAG      535
                                              Met Ser Leu Gln
                                                1

TTT ATC GGT CTA CAG CGG CGC GAT GTG GTA GCC CTG GTC AAC TTT CTG      583
Phe Ile Gly Leu Gln Arg Arg Asp Val Val Ala Leu Val Asn Phe Leu
  5              10                  15                  20

CGC CAT CTC ACG CAA AAG CCC GAC GTG GAT CTC GAG GCA CAC CCC AAG      631
Arg His Leu Thr Gln Lys Pro Asp Val Asp Leu Glu Ala His Pro Lys
                25                  30                  35

ATC CTG AAA AAA TGT GGC GAA AAA CGC CTG CAC CGG CGT ACG GTG CTG      679
Ile Leu Lys Lys Cys Gly Glu Lys Arg Leu His Arg Arg Thr Val Leu
            40                  45                  50
```

```
TTC AAC GAG CTC ATG CTT TGG TTG GGA TAC TAC CGC GAG CTG CGT TTT        727
Phe Asn Glu Leu Met Leu Trp Leu Gly Tyr Tyr Arg Glu Leu Arg Phe
         55                  60                  65

CAC AAC CCC GAC CTC TCC TCA GTG CTC GAG GAG TTC GAG GTG CGT TGC        775
His Asn Pro Asp Leu Ser Ser Val Leu Glu Glu Phe Glu Val Arg Cys
         70                  75                  80

GTG GCC GTG GCG CGT CGC GGC TAC ACT TAC CCG TTC GGT GAT CGT GGT        823
Val Ala Val Ala Arg Arg Gly Tyr Thr Tyr Pro Phe Gly Asp Arg Gly
 85                  90                  95                 100

AAG GCG CGT GAC CAC CTG GCT GTG CTA GAC CGT ACC GAA TTC GAT ACG        871
Lys Ala Arg Asp His Leu Ala Val Leu Asp Arg Thr Glu Phe Asp Thr
                105                 110                 115

GAC GTG CGC CAC GAT GCC GAG ATC GTG GAA CGC GCG CTC GTA AGC GCG        919
Asp Val Arg His Asp Ala Glu Ile Val Glu Arg Ala Leu Val Ser Ala
                120                 125                 130

GTC ATT CTG GCC AAG ATG TCG GTG CGC GAG ACG CTG GTC ACA GCC ATC        967
Val Ile Leu Ala Lys Met Ser Val Arg Glu Thr Leu Val Thr Ala Ile
            135                 140                 145

GGC CAG ACG GAA CCC ATC GCC TTT GTG CAC CTC AAG GAT ACG GAG GTG       1015
Gly Gln Thr Glu Pro Ile Ala Phe Val His Leu Lys Asp Thr Glu Val
    150                 155                 160

CAG CGC ATT GAA GAA AAC CTG GAG GGT GTG CGC CGT AAC ATG TTC TGC       1063
Gln Arg Ile Glu Glu Asn Leu Glu Gly Val Arg Arg Asn Met Phe Cys
165                 170                 175                 180

GTG AAA CCG CTC GAC CTT AAC CTG GAC CGG CAC GCC AAC ACG GCG CTG       1111
Val Lys Pro Leu Asp Leu Asn Leu Asp Arg His Ala Asn Thr Ala Leu
                185                 190                 195

GTC AAC GCC GTC AAC AAG CTC GTG TAC ACG GGC CGT CTC ATC ATG AAC       1159
Val Asn Ala Val Asn Lys Leu Val Tyr Thr Gly Arg Leu Ile Met Asn
                200                 205                 210

GTG CGC AGG TCT TGG GAG GAG CTG GAG CGC AAA TGT CTG GCG CGC ATT       1207
Val Arg Arg Ser Trp Glu Glu Leu Glu Arg Lys Cys Leu Ala Arg Ile
            215                 220                 225

CAG GAG CGC TGC AAG CTG CTG GTC AAG GAG CTG CGC ATG TGC CTT TCC       1255
Gln Glu Arg Cys Lys Leu Leu Val Lys Glu Leu Arg Met Cys Leu Ser
    230                 235                 240

TTT GAT TCC AAC TAC TGT CGC AAT ATC CTC AAG CAC GCC GTG GAA AAC       1303
Phe Asp Ser Asn Tyr Cys Arg Asn Ile Leu Lys His Ala Val Glu Asn
245                 250                 255                 260

GGC GAC TCG GCC GAC ACG CTG TTG GAG CTG CTC ATC GAG GAC TTT GAT       1351
Gly Asp Ser Ala Asp Thr Leu Leu Glu Leu Leu Ile Glu Asp Phe Asp
                265                 270                 275

ATC TAC GTG GAC AGC TTC CCA CAG TCG GCG CAC ACG TTT TTG GGC GCG       1399
Ile Tyr Val Asp Ser Phe Pro Gln Ser Ala His Thr Phe Leu Gly Ala
                280                 285                 290

CGC TCG CCG TCG TTG GAG TTT GAC GAT GAC GCC AAT CTC CTC TCG CTC       1447
Arg Ser Pro Ser Leu Glu Phe Asp Asp Asp Ala Asn Leu Leu Ser Leu
            295                 300                 305

GGC GGC GGT TCG GCC TTC TCG TCG GTA CCC AAG AAA CAT GTC CCC ACG       1495
Gly Gly Gly Ser Ala Phe Ser Ser Val Pro Lys Lys His Val Pro Thr
    310                 315                 320

CAG CCG CTG GAC GGC TGG AGC TGG ATC GCC AGT CCC TGG AAG GGA CAC       1543
Gln Pro Leu Asp Gly Trp Ser Trp Ile Ala Ser Pro Trp Lys Gly His
325                 330                 335                 340

AAA CCG TTC CGC TTC GAG GCC CAT GGT TCT CTG GCA CCG GCC GCC GAA       1591
Lys Pro Phe Arg Phe Glu Ala His Gly Ser Leu Ala Pro Ala Ala Glu
                345                 350                 355

GCC CAC GCT GCC CGT TCG GCG GCC GTC GGC TAT TAC GAC GAA GAG GAA       1639
Ala His Ala Ala Arg Ser Ala Ala Val Gly Tyr Tyr Asp Glu Glu Glu
```

```
                    360                 365                 370
AAG CGT CGC GAG CGG CAG AAA CGG GTG GAC GAC GAG GTG GTG CAG CGT    1687
Lys Arg Arg Glu Arg Gln Lys Arg Val Asp Asp Glu Val Val Gln Arg
        375                 380                 385

GAG AAA CAG CAG CTG AAG GCT TGG GAG GAG AGG CAG CAG AAC CTG CAG    1735
Glu Lys Gln Gln Leu Lys Ala Trp Glu Glu Arg Gln Gln Asn Leu Gln
    390                 395                 400

CAA CGT CAG CAG CAA CCA CCG CCC CCG GCA CGT AAA CCG AGC GCC TCC    1783
Gln Arg Gln Gln Gln Pro Pro Pro Pro Ala Arg Lys Pro Ser Ala Ser
405                 410                 415                 420

CGG AGG CTC TTT GGC TCC AGT GCC GAT GAG GAC GAC GAC GAT GAT GAT    1831
Arg Arg Leu Phe Gly Ser Ser Ala Asp Glu Asp Asp Asp Asp Asp Asp
                425                 430                 435

GAC GAG AAA AAC ATC TTT ACG CCC ATC AAG AAA CCG GGA ACT AGC GGC    1879
Asp Glu Lys Asn Ile Phe Thr Pro Ile Lys Lys Pro Gly Thr Ser Gly
            440                 445                 450

AAG GGC GCC GCT AGT GGT GGC GGT GTT TCC AGC ATT TTC AGC GGC CTG    1927
Lys Gly Ala Ala Ser Gly Gly Gly Val Ser Ser Ile Phe Ser Gly Leu
        455                 460                 465

TTA TCC TCG GGC AGT CAG AAA CCG ACC AGC GGT CCC TTG AAC ATC CCG    1975
Leu Ser Ser Gly Ser Gln Lys Pro Thr Ser Gly Pro Leu Asn Ile Pro
    470                 475                 480

CAA CAA CAA CAG CGT CAC GCG GCT TTC AGT CTC GTC TCC CCG CAG GTG    2023
Gln Gln Gln Gln Arg His Ala Ala Phe Ser Leu Val Ser Pro Gln Val
485                 490                 495                 500

ACC AAG GCC AGC CCG GGA AGG GTC CGT CGG GAC AGC GCG TGG GAC GTG    2071
Thr Lys Ala Ser Pro Gly Arg Val Arg Arg Asp Ser Ala Trp Asp Val
                505                 510                 515

AGG CCG CTC ACG GAG ACC AGA GGG GAT CTT TTC TCG GGC GAC GAG GAT    2119
Arg Pro Leu Thr Glu Thr Arg Gly Asp Leu Phe Ser Gly Asp Glu Asp
            520                 525                 530

TCC GAC AGC TCG GAT GGC TAT CCC CCC AAC CGT CAA GAT CCG CGT TTC    2167
Ser Asp Ser Ser Asp Gly Tyr Pro Pro Asn Arg Gln Asp Pro Arg Phe
        535                 540                 545

ACC GAC ACG CTG GTG GAC ATC ACG GAT ACC GAG ACG AGC GCC AAA CCG    2215
Thr Asp Thr Leu Val Asp Ile Thr Asp Thr Glu Thr Ser Ala Lys Pro
    550                 555                 560

CCC GTC ACC ACC GCG TAC AAG TTC GAG CAA CCG ACG TTG ACG TTC GGC    2263
Pro Val Thr Thr Ala Tyr Lys Phe Glu Gln Pro Thr Leu Thr Phe Gly
565                 570                 575                 580

GCC GGA GTT AAC GTT CCT GCT GGC GCC GGC GCT GCC ATC CTC ACG CCG    2311
Ala Gly Val Asn Val Pro Ala Gly Ala Gly Ala Ala Ile Leu Thr Pro
                585                 590                 595

ACG CCT GTC AAT CCT TCC ACG GCC CCC GCT CCG GCC CCG ACA CCT ACC    2359
Thr Pro Val Asn Pro Ser Thr Ala Pro Ala Pro Ala Pro Thr Pro Thr
            600                 605                 610

TTC GCG GGT ACC CAA ACC CCG GTC AAC GGT AAC TCG CCC TGG GCT CCG    2407
Phe Ala Gly Thr Gln Thr Pro Val Asn Gly Asn Ser Pro Trp Ala Pro
        615                 620                 625

ACG GCG CCG TTG CCC GGG GAT ATG AAC CCC GCC AAC TGG CCG CGC GAA    2455
Thr Ala Pro Leu Pro Gly Asp Met Asn Pro Ala Asn Trp Pro Arg Glu
    630                 635                 640

CGC GCG TGG GCC CTC AAG AAT CCT CAC CTG GCT TAC AAT CCC TTC AGG    2503
Arg Ala Trp Ala Leu Lys Asn Pro His Leu Ala Tyr Asn Pro Phe Arg
645                 650                 655                 660

ATG CCT ACG ACT TCC ACG GCT TCT CAA AAC ACC GTG TCC ACC ACC CCT    2551
Met Pro Thr Thr Ser Thr Ala Ser Gln Asn Thr Val Ser Thr Thr Pro
                665                 670                 675

CGG AGG CCG TCG ACT CCA CGC GCC GCG GTG ACA CAA ACA GCG TCT CGG    2599
Arg Arg Pro Ser Thr Pro Arg Ala Ala Val Thr Gln Thr Ala Ser Arg
```

```
                                                -continued

Arg Arg Pro Ser Thr Pro Arg Ala Ala Val Thr Gln Thr Ala Ser Arg
            680                 685                 690

GAC GCC GCT GAT GAG GTT TGG GCT TTA AGG GAC CAA ACT GCA GAG TCA    2647
Asp Ala Ala Asp Glu Val Trp Ala Leu Arg Asp Gln Thr Ala Glu Ser
        695                 700                 705

CCG GTC GAA GAC AGC GAG GAG GAA GAC GAC GAC TCC TCG GAC ACC GGC    2695
Pro Val Glu Asp Ser Glu Glu Glu Asp Asp Asp Ser Ser Asp Thr Gly
    710                 715                 720

TCC GTC GTC AGC CTG GGA CAC ACA ACA CCG TCG TCC GAT TAC AAC AAC    2743
Ser Val Val Ser Leu Gly His Thr Thr Pro Ser Ser Asp Tyr Asn Asn
725                 730                 735                 740

GAC GTC ATT TCG CCT CCC AGT CAG ACG CCC GAG CAG TCG ACG CCG TCC    2791
Asp Val Ile Ser Pro Pro Ser Gln Thr Pro Glu Gln Ser Thr Pro Ser
            745                 750                 755

AGA ATA CGT AAA GCT AAG TTA TCG TCT CCA ATG ACG ACG ACA TCC ACG    2839
Arg Ile Arg Lys Ala Lys Leu Ser Ser Pro Met Thr Thr Thr Ser Thr
        760                 765                 770

AGC CAG AAA CCG GTG CTG GGC AAG CGA GTC GCG ACG CCG CAC GCG TCC    2887
Ser Gln Lys Pro Val Leu Gly Lys Arg Val Ala Thr Pro His Ala Ser
    775                 780                 785

GCC CGA GCG CAG ACG GTG ACG TCG ACG CCG GTT CAG GGA AGG CTA GAG    2935
Ala Arg Ala Gln Thr Val Thr Ser Thr Pro Val Gln Gly Arg Leu Glu
790                 795                 800

AAA CAG GTG TCG GGC ACG CCG TCG ACG GTA CCC GCC ACG CTG TTG CAA    2983
Lys Gln Val Ser Gly Thr Pro Ser Thr Val Pro Ala Thr Leu Leu Gln
805                 810                 815                 820

CCT CAA CCG GCT TCG TCT AAA ACG ACG TCA TCA AGG AAC GTG ACT TCT    3031
Pro Gln Pro Ala Ser Ser Lys Thr Thr Ser Ser Arg Asn Val Thr Ser
            825                 830                 835

GGC GCG GGA ACC TCT TCC GCT TCT TCG GCT CGA CAG CCG TCA GCC TCG    3079
Gly Ala Gly Thr Ser Ser Ala Ser Ser Ala Arg Gln Pro Ser Ala Ser
        840                 845                 850

GCG TCC GTT TTG TCG CCC ACG GAG GAT GAT GTC GTG TCC CCC GCC ACA    3127
Ala Ser Val Leu Ser Pro Thr Glu Asp Asp Val Val Ser Pro Ala Thr
    855                 860                 865

TCG CCG CTG TCC ATG CTT TCG TCA GCC TCT CCG TCC CCG GCC AAG AGT    3175
Ser Pro Leu Ser Met Leu Ser Ser Ala Ser Pro Ser Pro Ala Lys Ser
870                 875                 880

GCC CCC CCG TCT CCG GTG AAA GGC CGG GGC AGC CGC GTC GGT GTT CCT    3223
Ala Pro Pro Ser Pro Val Lys Gly Arg Gly Ser Arg Val Gly Val Pro
885                 890                 895                 900

TCC TTG AAA CCT ACT TTG GGC GGC AAG GCG GTG GTA GGT CGA CCG CCC    3271
Ser Leu Lys Pro Thr Leu Gly Gly Lys Ala Val Val Gly Arg Pro Pro
            905                 910                 915

TCG GTC CCC GTG AGC GGT AGC GCG CCG GGT CGC CTG TCC GGC AGC AGC    3319
Ser Val Pro Val Ser Gly Ser Ala Pro Gly Arg Leu Ser Gly Ser Ser
        920                 925                 930

CGG GCC GCC TCG ACC ACG CCG ACG TAT CCC GCG GTA ACC ACC GTT TAC    3367
Arg Ala Ala Ser Thr Thr Pro Thr Tyr Pro Ala Val Thr Thr Val Tyr
    935                 940                 945

CCA CCG TCG TCT ACG GCC AAA AGC AGC GTA TCG AAT GCG CCG CCT GTG    3415
Pro Pro Ser Ser Thr Ala Lys Ser Ser Val Ser Asn Ala Pro Pro Val
950                 955                 960

GCC TCC CCC TCC ATC CTG AAA CCG GGG GCG AGC GCG GCT TTG CAA TCA    3463
Ala Ser Pro Ser Ile Leu Lys Pro Gly Ala Ser Ala Ala Leu Gln Ser
965                 970                 975                 980

CGC CGC TCG ACG GGG ACC GCC GCC GTA GGT TCC CCC GTC AAG AGC ACG    3511
Arg Arg Ser Thr Gly Thr Ala Ala Val Gly Ser Pro Val Lys Ser Thr
            985                 990                 995
```

| | | |
|---|---|---|
| ACG GGC ATG AAA ACG GTG GCT TTC GAC CTA TCG TCG CCC CAG AAG AGC<br>Thr Gly Met Lys Thr Val Ala Phe Asp Leu Ser Ser Pro Gln Lys Ser<br>              1000                      1005                      1010 | 3559 |
| GGT ACG GGG CCG CAA CCG GGT TCT GCC GGC ATG GGG GGC GCC AAA ACG<br>Gly Thr Gly Pro Gln Pro Gly Ser Ala Gly Met Gly Gly Ala Lys Thr<br>    1015                      1020                      1025 | 3607 |
| CCG TCG GAC GCC GTG CAG AAC ATC CTC CAA AAG ATC GAG AAG ATT AAG<br>Pro Ser Asp Ala Val Gln Asn Ile Leu Gln Lys Ile Glu Lys Ile Lys<br>    1030                      1035                      1040 | 3655 |
| AAC ACG GAG GAA TAGTTAAGAA ACACACACGC AGACGTACTT TTTAATGAAA<br>Asn Thr Glu Glu<br>1045 | 3707 |
| CCATCGGATA GTGACGTGTC GGGAAAGGAG GACGGACGGA GGGTCAGGGA TGGGGAGACG | 3767 |
| TGAGAAAGTT GTCCGCGGGC AATTGCATGT CGCCCAGAAA GAACGTGGTT GTTCCGGCGG | 3827 |
| CGTGCATCTG CCGAAACACC GTGTGGTGGT TGTACGAGTA CACGTTACCG TCGCCCTCGG | 3887 |
| TAATTTGATA CAACGTGGCG ATGGGGTGC CCTGCGGGAT CACGATGGAA CGCGTGCGCG | 3947 |
| TCCACAGCGT GACTTTGAGC GGCTCGCCGC CGCGCCACAC GCTGAGCCCC GTGTAAAAGG | 4007 |
| CGTCCTCGTG TGGCAAGTTG CCACCAAGA AACACCGGTC TGTGATCTGC ACGTAGCGCA | 4067 |
| AGTCCAACTC CACCGTCTGC CGCGGTTGCA CCCCGAAGTG GATATCGTAA GGCGCGTGCA | 4127 |
| CCGTGAGCGA AAACACGTTG GGCTCATTGA GAAGCGGACA GTTGAGCGCG TCGCCGCTAA | 4187 |
| AAAAGAGTGA CGGGTTGCGG CTGAATCGCA GGTCGTACCC GCGCTGCGCG CTCGTCAGCA | 4247 |
| GGTAGAAGGA AAAAGCGCGC GGCATGTTGC GCGCCGTGAT CTTGTCCGAG ACGCGGTGAC | 4307 |
| AGAAGGAGGT GGCCACGGTG CCCAGCAGTT GGCGCTGTTC CGCGTCCACG CATAGTGAAT | 4367 |
| CCACGTTGAC GGTGAAAATG AGACCCATGA ATTCGTACTG CACGTTTTTG GACGCGATCC | 4427 |
| ACGCTTCGTC CTCGCCGGGT AGCGCTGCCT CGTCGTCGTC CATCGTGCCG CGGAACTGCG | 4487 |
| CGAGGTAGCG CGTAATTTTT TTGTGTCCGT ACGTGGTTAC GCGCTTACTG ATCCAGGTCA | 4547 |
| GATGGTCCAC GCGACATAGC AGCGTCGCGC CATGCCGCGT GACGCTGACC CGTCCAAAGG | 4607 |
| GCGCCGCCTC CTCCAACCCC GCAACGCCGC TCGGAGCACC GCCGCAGCCC GGCTTTCCCG | 4667 |
| GCGTCGTGAA AGGCACGGCG TAATGCGGGC AGGCGTGCGG CACGAAGGGC ACCATGACCA | 4727 |
| GTTGTGTGTG CAGAAAACCG ATCTGCACCG CCTGCGACTG CCGCATGGTT TCCTCGTCGT | 4787 |
| AAACCGCCAT GGACGAGCAG AGCCCGCCCT TGGTGATGAG CGGTTGCAGC ACCACGGAGC | 4847 |
| TCTCGCTGGT GGAGCAGAGC AGAAAGAAGA GCTCGGCGTA CGCCGCCTTG GCGTCACCA | 4907 |
| CGTTGGACCA GTCGTACTTG TAGCCGCAGC CCTGCGTGTT GTTGTAAATG ACGGGAAACG | 4967 |
| AGAGAAAGAT GCAGCCCTGC ACGTACGAAG CTTTCTCCGT CACGTTCGAG GCCGTGTTGT | 5027 |
| ACTGCTCGGT GATGGACACC AAGTACGACT CGTAGGCCGT CAGGTGCGAG GCCGAACGGT | 5087 |
| GAATCTTGGC GTGGCGCACG CAGCGACCGT AGTTGTCGCG GTCCGCGTCG CGTAGCGCTT | 5147 |
| CGATCCACGA GGTCACCACG TCCTGCGCCG GCAGACGATA GTCCTGCTCG GGTCCATGT | 5207 |
| GGCGGCACAG CCGCAGGCGC TCTGCCAGTT GGCGAGGGAT ACCGTCGTGC GACCTTTTGA | 5267 |
| CCGCGGTGGT GCCTGTCGTC CTCGTCTCCC CTCCTTCGTT CTCCCTGTTT TCTCTTCTCT | 5327 |
| CATTCCCGGT CTCCGGATCC GCAGCCGCTA CCTCTTGCTC CGCGGTTTTC TCGCCCACCT | 5387 |
| CGCTCGTCGC TGTCGCCGCC ACCGCAGCGG CGGCGACGGA CGGCGGCGGT AACAACAGCT | 5447 |
| CCGTGAAGCT GACGAGCGGC AGCGGCGACG ACGGTGGCGG CGACGACACG GCGACGGTCA | 5507 |
| ACAGGGTCAC AAGCGTGGGT TTGTCCCCCA TAATCTGGTC GCCGCCACCG CCGTCGTTGC | 5567 |
| CGGTCCCCGT TTCCTCCGGC GTCGCGGTTT CCGCCGTCTC CGGATGAGCG GCCGCGGCGC | 5627 |

```
GGGCTCGGCG TCCCGCCGTC CGAGACGGTG TATATAAACC GCGTCGGCCT CGCCGGCCCG       5687

AGCGCGCCGG GGAGAAGAAC CTCTTCCCGG GCCCCGCGTT CAAGACGGCG TGCCGTGACG       5747

CTCGATGGGT CCGCTTCATC AGACTGCGTA CGCTTTGGAG CGTCAGACCC AGGGCGCATG       5807

TAGCCGACTT GGAGGACTTT GCCGCCTTTT ATCGCACCCT CTCGGACAGT GAGCAGCAGG       5867

AGTTCGAGCA AGAAGCCGAA CTCGCCTCCC GCTCACAACG CGTGCAACAC CTGCGCGAGG       5927

CCCGGCGCCA GCTCAAGATG GACCTGATGT GTCACGGCGG TTGAAAACGC GCATGATCTC       5987

GCGAAGCCAT CTACGCGCCT GTCAGGGCGA TGACGACATC AGCGATGACG GCTCCTGATA       6047

CGCGCCGGCA GCTGCAGCAC GTGGAGACGC TGCGTCGGTT TCTGCGCGGC GACAGCTGCT       6107

TTGTGCACGA TCTCCCGGGC ATGATGGACT ATCACGACGG GCTCTCGCGC CGTCAACAGC       6167

GTGCCTTTTG CCGCGCGAGT CGCGTGTTGA CGGACCCGGA GCCCATCCAG AGCGAAGCGG       6227

AGGGGGAGAA TAAACAGTTT ACGGAGCACA CACACAAAGT AGTCTCGTTT TTTATTAAAA       6287

GTGTCTTTGT ATTTCCCTAT CTTGTGTTGC CCAACTGCTG TCAGGTCTCC GTAGATCGCT       6347

CCCGGGTGCC CGA                                                        6360
```

(2) INFORMATION FOR SEQ ID NO: 10:

(i) SEQUENCE CHARACTERISTICS:
        (A) LENGTH: 1048 amino acids
        (B) TYPE: amino acid
        (D) TOPOLOGY: linear (ii) MOLECULE TYPE: protein (xi) SEQUENCE DESCRIPTION: SEQ ID NO: 10:

```
Met Ser Leu Gln Phe Ile Gly Leu Gln Arg Arg Asp Val Val Ala Leu
 1               5                  10                  15

Val Asn Phe Leu Arg His Leu Thr Gln Lys Pro Asp Val Asp Leu Glu
            20                  25                  30

Ala His Pro Lys Ile Leu Lys Lys Cys Gly Glu Lys Arg Leu His Arg
        35                  40                  45

Arg Thr Val Leu Phe Asn Glu Leu Met Leu Trp Leu Gly Tyr Tyr Arg
    50                  55                  60

Glu Leu Arg Phe His Asn Pro Asp Leu Ser Ser Val Leu Glu Glu Phe
65                  70                  75                  80

Glu Val Arg Cys Val Ala Val Ala Arg Arg Gly Tyr Thr Tyr Pro Phe
                85                  90                  95

Gly Asp Arg Gly Lys Ala Arg Asp His Leu Ala Val Leu Asp Arg Thr
            100                 105                 110

Glu Phe Asp Thr Asp Val Arg His Asp Ala Glu Ile Val Glu Arg Ala
        115                 120                 125

Leu Val Ser Ala Val Ile Leu Ala Lys Met Ser Val Arg Glu Thr Leu
    130                 135                 140

Val Thr Ala Ile Gly Gln Thr Glu Pro Ile Ala Phe Val His Leu Lys
145                 150                 155                 160

Asp Thr Glu Val Gln Arg Ile Glu Glu Asn Leu Glu Gly Val Arg Arg
                165                 170                 175

Asn Met Phe Cys Val Lys Pro Leu Asp Leu Asn Leu Asp Arg His Ala
            180                 185                 190

Asn Thr Ala Leu Val Asn Ala Val Asn Lys Leu Val Tyr Thr Gly Arg
        195                 200                 205

Leu Ile Met Asn Val Arg Arg Ser Trp Glu Glu Leu Glu Arg Lys Cys
```

```
            210                 215                 220
Leu Ala Arg Ile Gln Glu Arg Cys Lys Leu Leu Val Lys Glu Leu Arg
225                 230                 235                 240

Met Cys Leu Ser Phe Asp Ser Asn Tyr Cys Arg Asn Ile Leu Lys His
                245                 250                 255

Ala Val Glu Asn Gly Asp Ser Ala Asp Thr Leu Leu Glu Leu Leu Ile
                260                 265                 270

Glu Asp Phe Asp Ile Tyr Val Asp Ser Phe Pro Gln Ser Ala His Thr
                275                 280                 285

Phe Leu Gly Ala Arg Ser Pro Ser Leu Glu Phe Asp Asp Ala Asn
290                 295                 300

Leu Leu Ser Leu Gly Gly Gly Ser Ala Phe Ser Ser Val Pro Lys Lys
305                 310                 315                 320

His Val Pro Thr Gln Pro Leu Asp Gly Trp Ser Trp Ile Ala Ser Pro
                325                 330                 335

Trp Lys Gly His Lys Pro Phe Arg Phe Glu Ala His Gly Ser Leu Ala
                340                 345                 350

Pro Ala Ala Glu Ala His Ala Ala Arg Ser Ala Ala Val Gly Tyr Tyr
                355                 360                 365

Asp Glu Glu Glu Lys Arg Arg Glu Arg Gln Lys Arg Val Asp Asp Glu
                370                 375                 380

Val Val Gln Arg Glu Lys Gln Gln Leu Lys Ala Trp Glu Glu Arg Gln
385                 390                 395                 400

Gln Asn Leu Gln Gln Arg Gln Gln Pro Pro Pro Ala Arg Lys
                405                 410                 415

Pro Ser Ala Ser Arg Arg Leu Phe Gly Ser Ser Ala Asp Glu Asp Asp
                420                 425                 430

Asp Asp Asp Asp Glu Lys Asn Ile Phe Thr Pro Ile Lys Lys Pro
                435                 440                 445

Gly Thr Ser Gly Lys Gly Ala Ala Ser Gly Gly Val Ser Ser Ile
                450                 455                 460

Phe Ser Gly Leu Leu Ser Gly Ser Gln Lys Pro Thr Ser Gly Pro
465                 470                 475                 480

Leu Asn Ile Pro Gln Gln Gln Arg His Ala Ala Phe Ser Leu Val
                485                 490                 495

Ser Pro Gln Val Thr Lys Ala Ser Pro Gly Arg Val Arg Arg Asp Ser
                500                 505                 510

Ala Trp Asp Val Arg Pro Leu Thr Glu Thr Arg Gly Asp Leu Phe Ser
                515                 520                 525

Gly Asp Glu Asp Ser Asp Ser Ser Asp Gly Tyr Pro Pro Asn Arg Gln
                530                 535                 540

Asp Pro Arg Phe Thr Asp Thr Leu Val Asp Ile Thr Asp Thr Glu Thr
545                 550                 555                 560

Ser Ala Lys Pro Pro Val Thr Thr Ala Tyr Lys Phe Glu Gln Pro Thr
                565                 570                 575

Leu Thr Phe Gly Ala Gly Val Asn Val Pro Ala Gly Ala Gly Ala Ala
                580                 585                 590

Ile Leu Thr Pro Thr Pro Val Asn Pro Ser Thr Ala Pro Ala Pro Ala
                595                 600                 605

Pro Thr Pro Thr Phe Ala Gly Thr Gln Thr Pro Val Asn Gly Asn Ser
                610                 615                 620

Pro Trp Ala Pro Thr Ala Pro Leu Pro Gly Asp Met Asn Pro Ala Asn
625                 630                 635                 640
```

-continued

```
Trp Pro Arg Glu Arg Ala Trp Ala Leu Lys Asn Pro His Leu Ala Tyr
            645                 650                 655
Asn Pro Phe Arg Met Pro Thr Thr Ser Thr Ala Ser Gln Asn Thr Val
            660                 665                 670
Ser Thr Thr Pro Arg Arg Pro Ser Thr Pro Arg Ala Ala Val Thr Gln
            675                 680                 685
Thr Ala Ser Arg Asp Ala Ala Asp Glu Val Trp Ala Leu Arg Asp Gln
690                 695                 700
Thr Ala Glu Ser Pro Val Glu Asp Ser Glu Glu Asp Asp Asp Ser
705                 710                 715                 720
Ser Asp Thr Gly Ser Val Val Ser Leu Gly His Thr Thr Pro Ser Ser
                    725                 730                 735
Asp Tyr Asn Asn Asp Val Ile Ser Pro Pro Ser Gln Thr Pro Glu Gln
                    740                 745                 750
Ser Thr Pro Ser Arg Ile Arg Lys Ala Lys Leu Ser Ser Pro Met Thr
                    755                 760                 765
Thr Thr Ser Thr Ser Gln Lys Pro Val Leu Gly Lys Arg Val Ala Thr
770                 775                 780
Pro His Ala Ser Ala Arg Ala Gln Thr Val Thr Ser Thr Pro Val Gln
785                 790                 795                 800
Gly Arg Leu Glu Lys Gln Val Ser Gly Thr Pro Ser Thr Val Pro Ala
                    805                 810                 815
Thr Leu Leu Gln Pro Gln Pro Ala Ser Ser Lys Thr Thr Ser Ser Arg
                    820                 825                 830
Asn Val Thr Ser Gly Ala Gly Thr Ser Ser Ala Ser Ser Ala Arg Gln
                    835                 840                 845
Pro Ser Ala Ser Ala Ser Val Leu Ser Pro Thr Glu Asp Asp Val Val
850                 855                 860
Ser Pro Ala Thr Ser Pro Leu Ser Met Leu Ser Ser Ala Ser Pro Ser
865                 870                 875                 880
Pro Ala Lys Ser Ala Pro Pro Ser Pro Val Lys Gly Arg Gly Ser Arg
                    885                 890                 895
Val Gly Val Pro Ser Leu Lys Pro Thr Leu Gly Gly Lys Ala Val Val
                    900                 905                 910
Gly Arg Pro Pro Ser Val Pro Val Ser Gly Ser Ala Pro Gly Arg Leu
                    915                 920                 925
Ser Gly Ser Ser Arg Ala Ala Ser Thr Thr Pro Thr Tyr Pro Ala Val
                    930                 935                 940
Thr Thr Val Tyr Pro Pro Ser Ser Thr Ala Lys Ser Ser Val Ser Asn
945                 950                 955                 960
Ala Pro Pro Val Ala Ser Pro Ser Ile Leu Lys Pro Gly Ala Ser Ala
                    965                 970                 975
Ala Leu Gln Ser Arg Arg Ser Thr Gly Thr Ala Ala Val Gly Ser Pro
                    980                 985                 990
Val Lys Ser Thr Thr Gly Met Lys Thr Val Ala Phe Asp Leu Ser Ser
                    995                 1000                1005
Pro Gln Lys Ser Gly Thr Gly Pro Gln Pro Gly Ser Ala Gly Met Gly
        1010                1015                1020
Gly Ala Lys Thr Pro Ser Asp Ala Val Gln Asn Ile Leu Gln Lys Ile
1025                1030                1035                1040
Glu Lys Ile Lys Asn Thr Glu Glu
                    1045
```

HUMAN CYTOMEGALOVIRUS DNA CONSTRUCTS AND USES THEREFOR

CROSS-REFERENCE TO OTHER APPLICATIONS

This application is a §371 of International Patent Application No. PCT/US97/06866 filed Apr. 22, 1997, which claims the benefit of priority of U.S. provisional patent application No. 60/015,717, filed Apr. 23, 1996.

FIELD OF THE INVENTION

This invention relates generally to compositions useful in preventing and treating human cytomegalovirus infection.

BACKGROUND OF THE INVENTION

Cytomegalovirus (CMV) is one of a group of highly host specific herpes viruses that produce unique large cells bearing intranuclear inclusions. The envelope of the human cytomegalovirus (HCMV) is characterized by a major glycoprotein complex termed gB or gCI, which was previously referred to as gA.

Infection with HCMV is common and usually asymptomatic. However, the incidence and spectrum of disease in newborns and immunocompromised hosts establishes this virus as an important human pathogen. HCMV has also been suggested to be an important co-factor in the development of atherosclerosis and restenosis after angioplastic surgery.

Several HCMV vaccines have been developed or are in the process of development. Vaccines based on live attenuated strains of HCMV have been described. [See, e.g., S. A. Plotkin et al, *Lancet,* 1:528–30 (1984); S. A. Plotkin et al, *J. Infect. Dis.,* 134:470–75 (1976); S. A. Plotkin et al, "Prevention of Cytomegalovirus Disease by Towne Strain Live Attenuated Vaccine", in Birth Defects, Original Article Series, 20(1):271–287 (1984); J. P. Glazer et al, *Ann. Intern. Med.;* 91:676–83 (1979); and U.S. Pat. No. 3,959,466.] A proposed HCMV vaccine using a recombinant vaccinia virus expressing HCMV glycoprotein B has also been described. [See, e.g., Cranage, M. P. et al, *EMBO J.,* 5:3057–3063 (1986).] However, vaccinia vaccines are considered possible causes of encephalitis. Other recombinant HCMV vaccines have been described. See, e.g., G. S. Marshall et al, *J. Infect. Dis.,* 162:1177–1181 (1990); K. Berencsi et al, *J. Gen. Virol.,* 74:2507–2512 (1993), which describe adenovirus-HCMV recombinants.

There remains a need in the art for additional compositions useful in preventing CMV infection by enhancing immune responses to HCMV vaccines and generating neutralizing antibody and/or cellular responses to CMV in the human immune system.

SUMMARY OF THE INVENTION

The present invention provides a series of DNA molecules expressing human cytomegalovirus (HCMV) genome fragments, which are particularly useful in inducing HCMV-specific immune responses.

Thus, in one aspect, the invention provides a DNA molecule which is non-replicating in mammals and which comprises at least one human cytomegalovirus antigen which is operably linked to regulatory sequences which express the antigen in the mammal. Advantageously, the antigen elicits an immune response in said mammal. In one preferred embodiment, the DNA molecule is a plasmid.

In another aspect, the invention provides a plasmid, pTet-gB, containing the portion of the HCMV genome (UL55) encoding gB. This plasmid further contains a tetracycline regulatable HCMV-immediate early promoter, which is useful in controlling expression of gB. Another plasmid of the invention encoding the full-length gB subunit protein is a pΔRC-gB plasmid.

Yet another plasmid of the invention, pΔRC-gB$_{680}$, contains the portion of the HCMV genome encoding the N-terminal 680 amino acids of the gB protein (gB$_{1-680}$).

The pΔRC-pp65 plasmid of the invention contains the portion of the HCMV genome (UL83) encoding the HCMV pp65 tegument protein. The pΔRC-pp150 plasmid contains the portion of the HCMV genome (UL32) encoding the HCMV pp150 tegument protein.

The pΔRC-exon-4 contains the portion of the HCMV genome (truncated UL123) encoding HCMV immediate-early (IE) exon-4.

In yet another aspect, the present invention provides an immunogenic composition of the invention comprising at least one of the DNA molecules of the invention and a carrier.

In still another aspect, the present invention provides a method of inducing HCMV-specific immune responses in an animal by administering to the animal an effective amount of an immunogenic composition of the invention. Preferably, this composition contains pΔRC-gB$_{680}$, pTet-gB and/or pΔRC-pp65.

In yet a further aspect, the present invention provides a method of priming immune responses to a selected human cytomegalovirus immunogenic composition by administering an immunogenic composition of the invention prior to administration of the second immunogenic or vaccine composition.

Other aspects and advantages of the present invention are described further in the following detailed description of the preferred embodiments thereof.

BRIEF DESCRIPTION OF THE DRAWINGS

FIGS. 3A–3E provides the full-length DNA and amino acid sequences [SEQ ID NO:1 and 2] of a human cytomegalovirus virus gB gene.

FIGS. 4A–B provide the full-length DNA and amino acid sequences [SEQ ID NO:3 and 4] of a human cytomegalovirus immediate-early exon-4.

FIG. 5 provides the full-length DNA and amino acid sequences of a human cytomegalovirus phosphoprotein (pp) 65 gene Towne strain on the top line [SEQ ID NO: 5 and 6], and, on the bottom line, the sequence of the pp65-AD169 strain where it differs from the Towne strain [SEQ ID NO: 7 and 8].

FIG. 6A–6I provide the full-length DNA and amino acid sequences [SEQ ID NO: 9 and 10] of a human cytomegalovirus phosphoprotein (pp) 150 gene, AD169 strain.

DETAILED DESCRIPTION OF THE INVENTION

Figure 1:
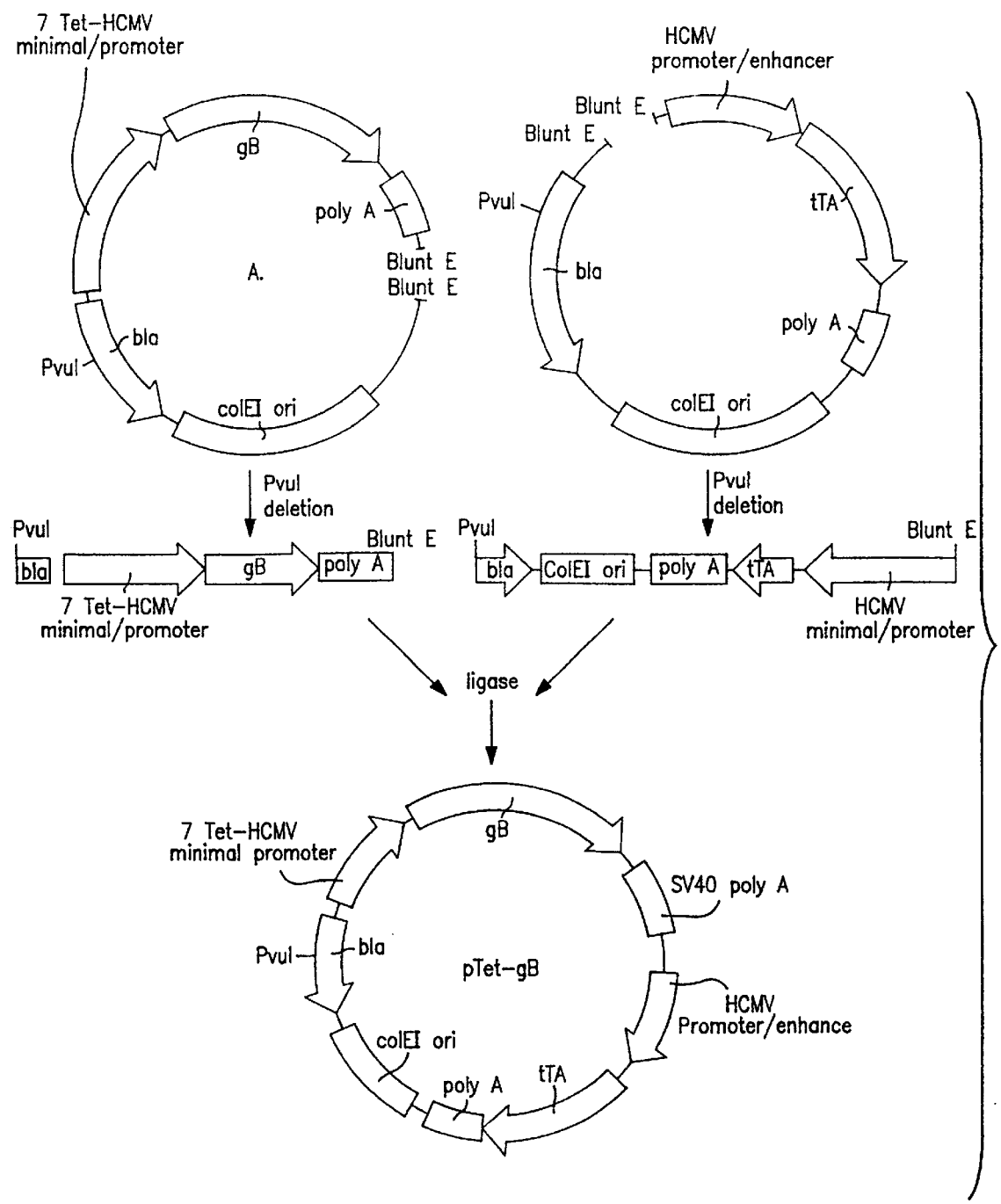
FIG. 1 illustrates the construction of the pTet-gB plasmid.

The present invention provides DNA molecules useful for in vitro and in vivo expression of antigenic fragments of the HCMV genome. Particularly desirable antigens include full-length and transmembrane-deleted fragments of gB such as $gB_{1-680}$, pp65, pp150, and IE-exon-4. Preferably, the DNA molecules of the invention are plasmids. The inventors have found that these DNA molecules induce HCMV-specific immune responses, including ELISA and neutralizing antibodies and cytotoxic T lymphocytes (CTL), and are further useful in priming immune responses to subsequently administered HCMV immunogens and vaccines.

Thus, in one embodiment, the present invention provides a DNA molecule containing at least one HCMV antigen under the control of regulatory sequences which express the antigen in vivo or in vitro. Desirably, the DNA molecule is incapable of replicating in mammals. In a particularly desirable aspect of this embodiment, the DNA molecule is a plasmid.

As defined herein, an HCMV antigen includes a portion of the HCMV genome or a protein or peptide encoded thereby which induces an immune response in a mammal. Desirably, the immune response induced is HCMV-specific and protective. However, non-protective immune responses are also useful according to the invention, e.g., for priming immune responses. Currently, preferred HCMV antigens include full-length gB, a fragment or derivative of gB which lacks at least the transmembrane domain, pp65, pp150, and the immediate-early exon-4. Other suitable antigens may be readily selected by one of skill in the art.

The exemplary DNA molecules of invention, described herein, have been constructed using gene fragments derived from the Towne strain of HCMV. The Towne strain of HCMV, is particularly desirable because it is attenuated and has a broad antigenic spectrum. This strain is described in *J. Virol.*, 11 (6): 991 (1973) and is available from the ATCC under accession number VR-977. The Ad169 strain is also available from the ATCC, under accession number VR-538. However, other strains of CMV useful in the practice of this invention may be obtained from depositories like the ATCC or from other institutes or universities, or from commercial sources.

Thus, the CMV gene fragment encoding the desired protein (e.g., gB, pp65, pp150) or protein fragment (e.g., $gB_{1-680}$ or IE-exon-4) may be isolated from known HCMV strains. See, e.g., Mach et al, *J. Gen. Virol.*, 67:1461–1467 (1986); Cranage, M. P. et al, *EMBO J.*, 5:3057–3063 (1986); and Spaete et al, *Virol.*, 167:207–225 (1987), which provide isolation techniques. For example, using a known HCMV sequence, the desired HCMV gene or gene fragment [e.g., pp65 (UL83)] is PCR amplified, isolated, and inserted into the plasmid vector or other DNA molecule of the invention using known techniques. Alternatively, the desired CMV sequences can be chemically synthesized by conventional methods known to one of skill in the art, purchased from commercial sources, or derived from CMV strains isolated using known techniques.

If desired, the DNA molecules of the invention may contain multiple copies of the HCMV gene or gene fragment. Alternatively, the recombinant plasmid may contain more than one HCMV gene/gene fragment, so that the plasmid may express two or more HCMV proteins. For example, as shown herein, the presence of both gB- and pp65-specific ELISA antibodies and pp65-specific CTL in the mice inoculated with pTet-gB and pΔRC-pp65 in a mixture indicates that gB and pp65 do not mutually block antigen presentation or B and T cell stimulation when expressed in the same cells or in close proximity. Thus, gB (or $gB_{680}$) and pp65 proteins are particularly well suited for incorporation into a plasmid which expressed both protein (termed herein a chimeric vector). Thus, one particularly desirable embodiment of the present invention provides a DNA molecule containing the gB and the pp65 antigens. In another particularly desirable embodiment, the DNA molecule contains a transmembrane-deleted gB fragment or derivative (e.g., $gB_{680}$ or gBΔtm) and the pp65 antigens.

In the construction of the DNA molecules of the invention, one of skill in the art can readily select appropriate regulatory sequences, enhancers, suitable promoters, secretory signal sequences and the like. In the examples below, the plasmids have been provided with a tetracycline repressor from *E. coli*. However, if desired, the plasmid or other DNA molecule may be engineered to contain another regulatable promoter, which "turns on" expression upon administration of an appropriate agent (e.g., tetracycline), permitting regulation of in vivo expression of the HCMV gene product. Such agents are well known to those of skill in the art. The techniques employed to insert the HCMV gene into the DNA molecule and make other alterations, e.g., to insert linker sequences and the like, are known to one of skill in the art. See, e.g., Sambrook et al, "Molecular Cloning. A Laboratory Manual" (2d edition), Cold Spring Harbor Laboratory, Cold Spring Harbor, N.Y. (1989).

In one embodiment, the DNA molecules of the invention are plasmids. One exemplary plasmid is pTet-gB. Construction of this plasmid is described in more detail below. Plasmid TetotTA-gB contains the gene from HCMV (the unique long (UL) 55) encoding the full-length gB subunit protein and a tetracycline regulatable HCMV-immediate early promoter which controls expression of gB. For convenience, the sequences of the HCMV gene fragment encoding the full-length gB protein which were used in the examples below are provided in FIGS. 3A–3E [SEQ ID NO: 1 and 2]. As discussed herein, this invention is not limited to this strain of HCMV. pTet-gB has been found to be useful alone, and in conjunction with the other DNA molecules of the invention, and particularly the pΔRC-pp65 plasmid described below. pTet-gB is also particularly useful for priming immune responses to subsequently administered HCMV immunogenic compositions and vaccines.

The pTetotTA-gB plasmid has been deposited pursuant to the Budapest Treaty, in the American Type Culture Collection (ATCC), 12301 Parklawn Drive, Rockville, Md., U.S.A. This deposit, designated ATCC 98029, was made on Apr. 23, 1996 and is termed herein, pTet-gB.

Other plasmids provided herein, pΔRC-gB and pCBgB, also contain the HCMV gene encoding the gB protein. As demonstrated below, these DNA plasmids have been found to be highly potent immunogens for HCMV. See Examples 8 and 14.

Another plasmid of the invention, pΔRC-$gB_{680}$ contains the portion of the HCMV gene encoding the N-terminal 680 amino acids of the gB protein and is capable of expressing this fragment in vivo or in vitro. This gB fragment is designated herein $gB_{1-680}$. As illustrated in FIGS. 3A–E

[SEQ ID NO:2], the full-length gB subunit protein consists of 907 amino acids. This plasmid, which expresses a secreted form of gB, has been found to be a more potent immunogen than the plasmids expressing the full-length gB.

Also provided herein is plasmid pCDgBΔtm, which contains a deletion of the gB transmembrane region. This plasmid has been found to induce HCMV-specific neutralizing antibodies (see Example 14) and to be a more potent immunogen than the corresponding DNA plasmid encoding full-length gB.

Plasmid pΔRC-exon-4 plasmid contains the portion of the HCMV immediate-early (IE) gene encoding HCMV IE-exon-4 and is capable of expressing the gene product. The HCMV IE-exon-4 gene fragment has been described in international patent application PCT/US94/02107, published Aug. 18, 1994, which is incorporated by reference herein. The IE gene and the intron/exon junctions for Towne strain HCMV are provided in Stenberg et al, *J. Virol.*, 49:190–199 (1984), and are available from GenBank under accession number K01484, M11828-30. The sequences of the IE-exon-4 gene fragment, Towne strain, are provided in FIGS. 4A–B [SEQ ID NO: 3 and 4], for convenience. This invention is not limited to the use of the IE-exon-4 sequences from this viral strain.

Plasmid pΔRC-pp65 contains the HCMV gene encoding the HCMV phosphoprotein (pp) 65 tegument protein and is capable of expressing pp65 in vivo or in vitro. As described herein, immunization with pΔRC-pp65 induced a reduction of virus titers in the mouse lung after intranasal challenge with vaccinia recombinants carrying the pp65 gene, suggesting the protective function of cell-mediated immunity in lung after DNA immunization. Further, in contrast to a prior art pp65-containing plasmid construct which induced ELISA antibodies in only about 60% of inoculation mice, nearly 100% of mice inoculated with pΔRC-pp65 responded with pp65-specific ELISA antibodies. The sequences of the pp65 gene, Towne and AD169 strains, have been described in H. Pande et al, *Virol.*, 181(1):220–228 (1991) and are provided in FIG. 5 [SEQ ID NO: 5–8] for convenience. pp65 sequences may be readily isolated using known techniques from other HCMV strains, or obtained from commercial sources. The strain from which the pp65 sequences are derived is not a limitation on the present invention.

Plasmid pΔRC-pp150 contains the portion of the HCMV gene encoding the HCMV pp150 tegument protein and is capable of expressing pp150 *in vivo* or *in vitro*. The sequences of the pp150 gene, Ad169 strain, have been described in G. Jahn et al, *J. Virol.*, 61(5):1358–1367 (1987) and are provided in FIGS. 6A–6I for convenience [SEQ ID NO: 9 and 10]. pp150 sequences may be readily isolated using known techniques from another HCMV strain, or obtained from commercial sources. The strain from which the pp150 sequences are derived is not a limitation on the present invention.

The DNA molecules, and particularly the plasmids described herein, may be used for expression of the gB, $gB_{1-680}$ fragment, pp65, pp150, or IE-exon-4 in vitro. The molecules are introduced by conventional means into the desired host cell [see, Sambrook et al, cited above]. Suitable host cells include, without limitation, bacterial cells, mammalian cells and cell lines, e.g., A549 (human lung carcinoma) or 293 (transformed human embryonic kidney) cells.

The host cell, once transfected with the recombinant plasmid (or other DNA molecule) of the present invention, is then cultured in a suitable medium, such as Minimal Essential Medium (MEM) for mammalian cells. The culture conditions are conventional for the host cell and allow the expressed HCMV protein, e.g., gB, to be produced either intracellularly, or secreted extracellularly into the medium. Conventional protein isolation techniques are employed to isolate the expressed subunit from the selected host cell or medium.

Alternatively, transfected host cells are themselves used as antigens, e.g., in in vitro immunological assays, such as enzyme-linked immunosorbent assays (ELISA). Such assay techniques are well known to those of skill in the art.

In yet another embodiment, one or more of the DNA molecules (e.g., plasmids) described herein may be used directly as immunogens in an immunogenic composition or directly for priming the immune response to a subsequently administered immunogenic or vaccine composition. According to this embodiment of the invention, the DNA molecule (e.g., plasmid) containing the HCMV gene or gene fragment is introduced directly (i.e., as "naked DNA") into the animal by injection. The DNA molecule of the invention, when introduced into an animal, transfects the host's cells and produces the CMV protein in those cells. Methods of administering so-called 'naked DNA', are known to those of skill in the art. [See. e.g., J. Cohen, *Science*, 259:1691–1692 (Mar. 19, 19930; E. Fynan et al, *Proc. Natl. Acad. Sci.*, 90:11478–11482 (December 1993); J. A. Wolff et al, *Biotechniques*, 11:474–485 (1991); International Patent Application PCT WO94/01139, which are incorporated by reference herein for purposes of described various 'naked DNA' delivery methods.]

The preparation of a pharmaceutically acceptable immunogenic composition, having appropriate pH, isotonicity, stability and other conventional characteristics is within the skill of the art. Currently, in a preferred embodiment, one or more of the recombinant plasmids (or other DNA molecules) of the invention is suspended in an acceptable carrier such as isotonic water, phosphate buffered saline, or the like. Optionally, although currently less preferred, such a composition may contain other components, such as adjuvants, e.g., aqueous suspensions magnesium hydroxides.

An effective amount of an immunogenic composition of the invention preferably contains between 10 μg and 10 μg, and preferably between about 80 μg and 150 μg of DNA of the invention per inoculation. Desirably, for each inoculation, the DNA of the invention is formulated in about 100 μl of a suitable carrier. In a particularly preferred embodiment, each patient is administered 100 μg DNA, which is administered three times at about 4 week intervals. Alternatively, the dosage regimen involved in the method for immunizing with the recombinant DNA molecule (e.g., plasmid) of the present invention can be determined considering various clinical and environmental factors known to affect vaccine administration. For example, following a first administration of an immunogenic composition of the invention, boosters may be administered approximately 2- to 15-weeks later. These boosters may involve an administration of the same immunogenic composition as was first administered, or may involve administration of an effective amount of another immunogenic composition of the invention. Additional doses of the vaccines of this invention may also be administered where considered desirable by the physician.

In another aspect, the present invention provides a method of inducing HCMV-specific immune responses in an animal. The method involves administering to an animal an effective amount of an immunogenic composition containing one or more of the DNA molecules of the invention, as described above. The immunogenic composition is administered by any suitable route, including oral, nasal routes, subcutaneous and intraperitoneal. However, currently preferred are the intramuscular and intradermal routes of administration.

In a particularly preferred embodiment of this aspect, the method of inducing an HCMV-specific immune response of the invention involves the administration of one or more immunogenic compositions of the invention. These compositions may be formulated so as to contain a single DNA molecule of the invention, or may contain mixtures of the DNA molecules of the invention. In one desirable embodiment, the composition contains pARc-gB$_{680}$ or pCBgBΔtm. In another desirable embodiment, the composition contains a plasmid containing pp65 according to the invention. As illustrated in the examples below, administration of pΔRC-pp65 has been found to induce a potent HCMV-specific immune response. In another desirable embodiment of the invention, the combined administration of pTet-gB and pΔRC-pp65 invention (which may be formulated in a single composition, or preferably, administered separately) induces potent HCMV-specific ELISA and neutralizing antibodies to both proteins. In yet another desirable embodiment, the present invention provides a composition containing a chimeric plasmid which expresses pp65 and gB$_{680}$ or gB. Yet another desired embodiment involves combined administration of pΔRC-gB$_{680}$ and pΔRC-pp65.

In another aspect of this invention, a method of priming immune responses to a human cytomegalovirus immunogenic or vaccinal composition is provided. This method involves administering an immunogenic composition of the invention prior to administration of a second immunogenic or vaccinal composition. Desirably, an effective amount of an immunogenic composition of the invention, e.g., containing pTet-gB, is administered between about 4 and 15 weeks prior to administration of the immunogenic or vaccinal composition. The second immunogenic or vaccinal composition, for which the immune response is enhanced or primed by the method of the invention, may be an immunogenic composition of the invention or a conventional immunogenic or vaccine composition. For example, such a composition may contain one or more HCMV proteins (e.g., the isolated, purified gB protein described in the examples below), a whole virus (e.g., semipurified Towne strain HCMV virion), or recombinant HCMV viruses. Suitable recombinant viruses are well known to those of skill in the art and include, e.g., the Ad-gB virus [G. Marshall et al, (1990), cited above, and EP 389 286; the Ad-gB-IE-exon-4 virus [WO 94/17810]; the Ad-gB fragment viruses [WO 94/23744]. Other suitable HCMV vaccinal compositions are well known to those of skill in the art.

These examples illustrate the preferred methods for preparing and using the plasmids of the invention. These examples are illustrative only and do not limit the scope of the invention.

EXAMPLE 1

Construction of pTet-gB Plasmid

The full-length HCMV-gB gene was obtained from the plasmid pAd-gB [Marshall et al., *J. Infect. Dis.*, 162:1177–1181 (1990)] by XbaI—XbaI-digestion.

The full length HCMV-gB was inserted into the plasmid pUHD10-3 [Gossen and Bujard, *Proc. Natl. Acad. Sci. USA*, 12:5547–5551 (1992)]. This plasmid contains:

(a) a tetracycline regulatable promoter (HCMV minimal promoter, −53 relative to the start site, with heptamerized tet-operon derived from the regulatory region of tet$^R$—gene of transposon −10);

(b) a multiple cloning site (including an XbaI site); and (c) an SV40 polyadenylation signal downstream of the polycloning site.

After inserting the HCMV-gB (referred to as pTetO-gB), the plasmid was digested with Hind III followed by blunt-ending, then digested with PvuI and the fragment containing the tetracycline regulatable promoter-HCMV-gB-SV40 polyA signal sequences was isolated and inserted into the plasmid pUHD15-1 [Gossen and Bujard, cited above]. This latter plasmid (hereafter referred to as ptTA) contains the HCMV-IE promoter-enhancer which constitutively drives the tTAgene followed by the SV40 polyA signal. The tTA-gene codes for a fusion protein consisting of the tetracycline repressor from *E. coli* and the carboxy-terminal 130 amino acids of the herpes simplex virus protein 16 gene (HSV VP-16). This fusion protein is a powerful transactivator of the tetracycline regulatable promoter of pTeto (which drives the HCMV-gB gene), because of the specific and high affinity attachment of the tetracycline repressor to the tetracycline operator sequences ensures the activation of transcription from the minimal HCMV promoter by the transactivator domain of HSV VP-16 gene (fused to the tetracycline repressor). The gene activation is specific for the pteto promoter. In the presence of low, non-toxic concentration of tetracycline (1 µg/ml or less), however, the transactivation is switched off, since tetracycline prevents the attachment of the tetracycline repressor to the teto sequences and no or very low gene expression is allowed (i.e., only the minimal HCMV promoter basal activity which is negligible in almost all cell types investigated so far).

To obtain the gB-expression plasmid regulatable by tetracycline, ptTA was cut just upstream of the HCMV-IE promoter/enhancer by XhoI, blunt-ended and cut with PvuI. The large fragment containing the HCMV-IE promoter-enhancer-tTA fusion protein gene followed by the SV40 polyA signal and the *E. coli* sequences of the plasmid (i.e., the replication origin and the beta-lactamase genes) were isolated. This isolated fragment was ligated with the fragment of pUHD10-3 containing the gB gene by the competent blunt-end and PvuI ends, resulting in the plasmid pteto-gB-tTA. The resulting plasmid contains both the transactivator and the HCMV-gB gene. The structure of the plasmid is, in addition to the *E. coli*-part, tetracycline-regulatable promoter (7 teto+minimal HCMV promoter) followed by the HCMV-gB gene, followed by the SV40 polyA signal, followed by the HCMV-IE promoter-enhancer, followed by the tTA gene and ending with the SV40 polyA signal.

The tetracycline-controllable expression system has been found to work correctly in vivo in the mouse as well [J. Dhawan et al, *Somatic Cell and Molecular Genetics*, 21:233–240 (1995)]. The pTet-gB plasmid is suitable to control naked DNA immunization. It is possible to give tetracycline to mice in their drinking water in concentrations not toxic for the animals but reaching sufficient levels able to regulate expression in muscle tissues [J. Dhawan et al., *Somatic Cell and Molecular Genetics*, 21: 233–240 (1995)]. By tetracycline treatment of transfected cultures or inoculated mice the time of antigen exposure can be manipulated. The silent presence of the inoculated plasmid can be tested. Without tetracycline treatment, however, this plasmid simply serves as a plasmid DNA immunogen or vaccine.

EXAMPLE 2

Construction of Further Plasmids

A. Construction of pRC-gB pRC/CMV (Invitrogen Corporation) contains the HCMV-IE promoter. The full length gB gene (XbaI—XbaI fragment from pAd5-gB) was obtained using conventional techniques [SEQ ID NO:1] and inserted into pRC/CMV according to manufacturer's directions. The resulting plasmid is termed herein pRC-gB.

B. Construction of pΔRC-gB pΔRC/CMV was derived from pRC/CMV plasmid by deleting the PvuII 1290–PvuII 3557 fragment to obtain more unique restriction sites. The full gB [SEQ ID NO:1], derived from the plasmid pAd-gB [Marshall et al., *J. Infect. Dis.*, 162:1177–1181 (1990)], was subcloned using conventional techniques, inserted into pUC-8 (commercially available), then obtained as a HindIII-BamHI fragment and inserted into the HindIII-BamHI digested pΔRC/CMV vector. The resulting plasmid is termed pΔRC-gB.

C. Construction of pΔRC-gB$_{680}$ pΔRC-gB$_{680}$ expresses the N-terminal 680 amino acids of the gB protein [SEQ ID NO:2]. The plasmid was derived from pΔRC-gB, by deleting the C-terminal 227 amino acids of the gB by Xho-digestion, Klenow polymerase filling, removing the C-terminal portion of the gB gene, and religation of the 5400 bp fragment. The insert is approximately 2200 bp.

EXAMPLE 3

Construction of pΔRC-pp65 and pΔRC-pp150

A. pΔRC-pp65

The plasmid pΔRC-pp65, which expresses the pp65 tegument protein of HCMV, was constructed as follows. H. Pande et al, *Virology*, 182(1):220–228 (1991), which provides the nucleotide sequences of the pp65 gene, is incorporated by reference herein [SEQ ID NO: 5 and 6].

The pp65 gene was isolated from the HCMV genome using conventional polymerase chain reaction techniques and inserted into a suitable expression plasmid. In this experiment, the 1696-bp pp65 gene was excised from the pUC-8-pp65 expression plasmid [Virogenetics] by NruI-BamHI digestion. The vector was blunt-ended with Klenow polymerase, digested with BamHI, and the pp65 gene inserted.

B. pΔRC-pp150

The plasmid, pΔRC-pp15O, which expresses the pp150 tegument protein of HCMV, was constructed as follows. The pp150 gene was isolated from the HCMV genome using conventional polymerase chain reaction techniques and inserted into a suitable expression plasmid. One of skill in the art can readily isolate this gene from a desired HCMV strain making use of the published sequences in G. Jahn et al, *J. Virol.*, 61(5):1358–1367 (1987) (which provides the nucleotide sequences of the Ad169 HCMV pp150 gene and is incorporated by reference herein). See, also FIGS. 6A–6I herein [SEQ ID NO: 9 and 10].

In this experiment, the isolated HCMV-pp150 gene was inserted into the XbaI-restricted pΔRCd [Virogenetics]. The insert is approximately 3200 bp [SEQ ID NO: 10].

EXAMPLE 4

Construction of pΔRC-IE-Exon-4

The plasmid, pΔRC-IE-Exon-4, which expresses the HCMV-IE exon4 product [SEQ ID NO:4], was constructed as follow. The gene was obtained from pAd5-IE-Exon-4 [International Patent Application WO94/17810, published Aug. 18, 1994 and Berencsi et al., *Vaccine*, 14:369–374 (1996)], by XbaI-digestion [SEQ ID NO:3]. The insert is 1230 bp.

EXAMPLE 5

Production of Plasmid Preparation Stocks

*E. coli* DH5alfa competent cells (Gibco BRL, Gaithersburg, Md.) were transformed with the constructed plasmids. Purified plasmid preparations were prepared on Plasmid Giga Kits (Qiagen Inc. Chatsworth, Calif.).

EXAMPLE 6

Expression of HCMV-proteins After Transient Transfection of 293 Cells With the Purified Plasmid Preparations Transient transfections were performed by the purified plasmid preparations, 1.5 μg/3×10$^5$ cells, using lipofectamine (Gaithersburg, Md.). Cells were tested for HCMV-protein expression 2 days after transfection by an immunofluorescence test as described in E. Gonczol et al, *Science*, 224:159–161 (1984). The antibodies used in this test include the monoclonal pp65-specific Ab [VIROSTAT, Portland, Me., stock # 0831], monoclonal gB-specific Ab [Advanced Biotechnologies, Columbia, Md.], and anti-pp150 monoclonal Ab [Virogenetics Corporation]. The IE-Exon-4-specific monoclonal Ab P63-27 was provided by W. Britt, University of Alabama at Birmingham.

The pTet-gB plasmid expresses the full-length HCMV-gB gene under the control of a tetracycline regulatable HCMV-IE promoter. The other plasmids express the inserted gene in transfected 293 cells under the control of the HCMV-IE promoter. Expression of gB, pp65 and pp150 was found to be strong using all plasmids.

After transfection with pTet-gB, 10–12% and <1% of cells expressed gB protein in the absence and presence, respectively, of 1 μg tetracycline [Tetracycline hydrochloride, Sigma, St. Louis, Mo.]. Sixty to seventy percent and 40–50% of cells transfected with pΔRC-gB and pΔgB$_{680}$ plasmids, respectively, expressed gB. pp65 protein was expressed in 70–80% of cells transfected with pΔRC-pp65.

EXAMPLE 7

Immunization Procedures and Assay Methods

A. Immunization Procedure

BALB/c or CBA mice were first pretreated i.m. with 100 μl of Bupivacaine HCl [0.25% Sensorcaine-MPF (ASTRA Pharmaceutical Products, Inc. Westborough, Mass.)]. In some experiments, identified below, no Bupivicaine pretreatment was used. One day later DNA was inoculated i.m. on the site of Bupivacaine infiltration. The dose for mice was 50–80 μg plasmid DNA/ inoculation. Booster inoculations were given i.m. 2×, without pretreatment with Bupivacaine. Mice immunized with pΔRC-gB plasmid were boosted 1×. Mice were bled by retroorbital puncture at the indicated times.

B. ELISA

Semipurified HCMV virions and purified gB proteins may be prepared by immunoaffinity column chromatography as described in E. Gonczol et al, *J. Virol.*, 58:661–664 (1986).

Alternatively, one of skill in the art can readily obtain suitable virions and gB proteins by alternative techniques.

Semipurified HCMV virions (Towne strain) or purified gB protein preparation were used as coating antigen for detection of gB-specific antibodies. OD values higher than mean OD values±2SD of preimmune sera were considered positive, or OD values >0.05, whichever was higher. Lysates of 293 cells transiently transfected with pΔRC-pp65 were used as coating antigen for detection of pp65-specific antibodies, lysates prepared from untransfected 293 cells served as control antigen. OD values obtained on control antigen-coated wells were subtracted from OD values obtained on pp65 antigen-coated wells and were considered positive if the resulting value was higher than 0.05.

C. Microneutralization assay

This assay was performed as described in E. Gonczol et al., *J. Virol. Methods,* 14:37–41 (1986). A neutralizing titer higher than 1:8 was considered positive.

D. Cytotoxic T lymphocyte assay

This assay was performed as described in K. Berencsi et al., *J. Gen Virol.,* 74:2507–2512 (1993). Briefly, spleen cells of immunized nice were restimulated in vitro with VacWR-pp65-infected (m.o.i.=0.2–0.5) autologous spleen cells (effector:stimulator ratio, 2.:1) for 5 days in 24-well plates. Cytolytic activity of nonadherent spleen cells was tested in a 4-h $^{51}$Cr-release assay. Target cells (P815 MHC class I-matched, MC57 MHC class I-mismatched) were infected with VacWR-pp65 or VT-Vac WR (m.o.i.=4–8). Percentage of specific $^{51}$Cr-release was calculated as [(cpm experimental release−cpm spontaneous release)/(cpm maximal release−cpm spontaneous release)×100]. A pp65-specific cytotoxicity higher than 10% was considered positive.

EXAMPLE 8

Induction of HCMV-Specific Immune Responses by the Plasmid Constructs Expressing the gB Protein BALB/c mice were inoculated 2 times at 0 and 5 weeks with 80 μg pΔRC-gB preparation. Serum samples at 5, 9 and 19 weeks after the first inoculation were tested for HCMV-specific ELISA antibodies and neutralizing antibodies (NA). The results are provided in Table 1 below, in which the ELISA antigen used was semipurified virions. The OD of responders is provided as the mean±SD at a serum dilution of 1:80. Mean±2SD of the 6 preimmunization sera at a dilution of 1:80 gave an OD value of 0.080. "GM" indicates the geometric mean.

TABLE 1 pΔRC-gB induces HCMV-specific ELISA and neutralizing antibodies (antigen: semipurified virion).

| weeks after first inoculation | No. of ELISA responders/ total | OD of resp. dil 1:80 | No. of NA resp. resp. | GM of NA |
|---|---|---|---|---|
| 0 | 0/6 | 0.036 ± 0.022 | 0/6 | NA |
| 5 | 5/6 | 0.314 ± 0.188 | 2/2 | 19 |
| 9 | 6/6 | 1.387 ± 0.810 | 6/6 | 34 |
| 19 | ND | ND | 4/4 | 22 |

These data demonstrate that all mice responded with both ELISA antibody and NA after the booster inoculation. The pΔRC-gB plasmid seems to be a highly potent immunizing construct.

TABLE 2 pTet-gB and pΔRC-pp65 induces insert-specific ELISA antibodies

| Mice Immunized With: | Weeks after first Inoc. | # ELISA responders/ total | OD* responders |
|---|---|---|---|
| pTet-gB | 4 | 1/10 | 0.062 |
| | 8 | 9/10 | 0.277 ± 0.257 |
| | 13 | 7/7 | 0.530 ± 0.625 |
| | 21 | 6/6 | 0.503 ± 0.682 |
| | 31 | 5/6 | 0.451 ± 0.505 |
| pΔRC-pp65 | 4 | 5/10 | 0.168 ± 0.070 |
| | 8 | 10/10 | 0.568 ± 0.387 |
| | 13 | 4/4 | 1.076 ± 0.216 |

*Mean OD ± SD of serum samples at dilution 1:40.

HCMV-specific ELISA antibodies were detected in 9 of 10 mice at 8 weeks after the first inoculation with pTet-gB (Table 2). HCMV neutralizing antibodies were detected in 4 of 10 mice, with titers between 1:16 and 1:48 (not shown). All mice immunized with the pΔRC-pp65 responded with pp65-specific ELISA antibodies. At 13 weeks (pp65- and gB-specific) and up to 31 weeks (gB-specific), OD values remained positive. In a separate experiment pp65-specific ELISA antibodies were also detected during the whole observation period (31 weeks) in 10 of the 10 immunized mice.

EXAMPLE 9

Induction of HCMV-Specific Immune Responses by the Plasmid Constructs Expressing pp65

To test whether the combination of the pTet-gB and pΔRC-pp65 results in reduced responses to the individual components, mice were immunized with both plasmids mixed together or inoculated separately. Groups of mice were inoculated with Bupivacaine (100 μl/mouse, 50 μl/leg), and 2 days later, with either a mixture of both plasmids (80 μg of each DNA/mouse, 40 μg of each DNA/leg, 160 μg DNA/mouse) or each plasmid inoculated into two different legs (80 μg DNA of each plasmid/mouse, a total of 160 μg DNA/mouse inoculated in left and right legs). A similar booster was given 4 weeks later. The time course of both the gB- and pp65-specific ELISA antibody response was very similar in both groups, with nearly all mice developing antibodies by 8 or 13 weeks after the first inoculation (Table 3). In another experiment using the combination of the two plasmids, comparable OD values were observed up to 31 weeks after the first inoculation.

TABLE 3 pTet-gB and pΔRC-pp65 inoculated into the same animal induce gB and pp65-specific antibodies

| Antigen, Inocula- tion | Weeks after 1st Inoc. | # gB- ELISA resp./ Total | OD* of responders | # pp65- ELISA resp./ Total | OD of Responders |
|---|---|---|---|---|---|
| pTet-gB + pΔRC- pp65, mixed | 4 | 4/10 | 0.087 ± 0.024 | 5/10 | 0.078 ± 0.033 |
| | 8 | 10/10 | 0.220 ± 0.143 | 10/10 | 0.400 ± 0.321 |
| | 13 | 10/10 | 0.392 ± 0.152 | 9/10 | 0.303 ± 0.224 |
| pTet-gB + pΔRC- | 4 | 8/10 | 0.076 ± 0.021 | 6/10 | 0.210 ± 0.124 |
| | 8 | 9/10 | 0.202 ± 0.268 | 8/10 | 0.452 ± 0.333 |

TABLE 3-continued pTet-gB and pARC-pp65 inoculated into the same animal induce gB and pp65-specific antibodies

| Antigen, Inocula- tion | Weeks after 1st Inoc. | # gB- ELISA resp./ Total | OD* of responders | # pp65- ELISA resp./ Total | OD of Responders |
|---|---|---|---|---|---|
| pp65, separately | 13 | 10/10 | 0.309 ± 0.202 | 8/10 | 0.308 ± 0.212 |

*The mean OD ± SD of serum samples at dilution 1:40.

Figure 2:
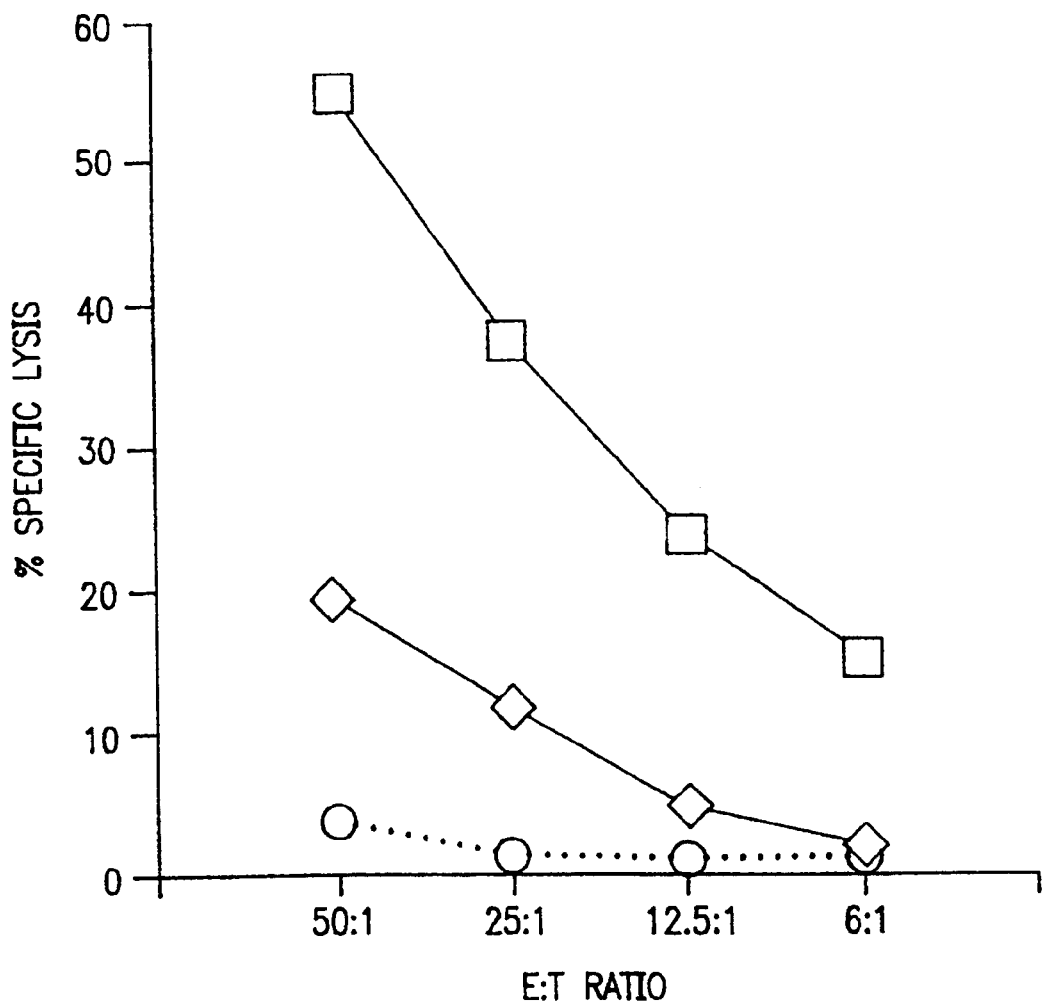
FIG. 2 is a graph illustrating the results of pp65-specific CTL responses in BALB/c mice immunized with pΔRC-pp65. The circle represents VacWR-pp65-infected MC57 (MHC-mismatched) target cells; the diamond represents WT-Vac-infected P-815 cells; and the square represents VacWR-pp65-infected P-815 (MHC-mismatched) target cells.

Of six mice inoculated with pARC-pp65 alone at a single site, 3 mice responded with pp65-specific lysis of target cells (FIG. 2). In a second similar experiment, 3 of 9 mice immunized with pARC-pp65 alone showed strong pp65-specific CTL responses. pp65-specific CTL were also detected in 4 of 5 tested nice inoculated with the mixture of pARC-pp65 and pTet-gB. When the pARC-pp65 and pTet-gB were inoculated separately into two different legs, 4 of 6 mice tested developed pp65-specific CTL response. These results establish that: 1) pp65-specific CTL responses are induced after DNA immunization; 2) there is no antigenic competition between the gB and pp65 proteins in the induction of antibody and CTL responses; and 3) gB protein expression in the cells at the inoculation site does not interfere with the presentation of pp65-specific T cell epitopes by MHC class I molecules to T cells.

EXAMPLE 10

Priming Effect of pTet-gB

One inoculation of naked plasmid DNA in mice did not result significant antibody responses in a high percentage of mice. To find out whether the immune system of the non-responder mice was specifically primed by the DNA inoculation, mice inoculated with pTet-gB were boosted 4 weeks later with either purified gB protein (5 µg gB/mouse in Alum s.c.) or with the Towne strain of HCMV (20 µg/mouse in Alum s.c.).

TABLE 4

Inoculation of mice with pTet-gB primes the immune system

| Antigen | wks after priming | No. of NA responder/all | GM of NA/ responder |
|---|---|---|---|
| Teto-gB/* | 4 | 0/10 | 5 |
| Teto-gB | 8 | 4/10 | 21 |
| Teto-gB/* | 4 | 0/10 | 4 |
| gB + Alu | 8 | 8/10 | 77 |
| —/* | 4 | 0/10 | NA |
| gB + Alu | 8 | 1/10 | 16 |
| Teto-gB/** | 12 | 1/5 | 16 |
| Towne + Alu | 14 | 5/5 | 97 |
| —/** | 12 | 0/5 | NA |
| Towne + Alu | 14 | 3/5 | 25 |

*second inoculations were given 4 weeks after the first inoculation
**Towne was given 12 weeks after the first inoculation This data demonstrates that pTet-gB inoculation primes immune-responses. In other words, the combination of Teto-gB priming and gB+Alu or Towne+Alu booster gave higher number of responder mice and slightly higher NA titers than TetotTA-gB given 2 times.

EXAMPLE 11

DNA Immunization Decreases Replication of the Corresponding Vaccinia Recombinant in Mice Vaccinia virus recombinants expressing either HCMV-gB or pp65 were prepared using the methods described in WO 94/17810, published Aug. 18, 1994. Briefly, the VacWR-gB and VacWR-pp65 recombinants were constructed as described [Gonczol et al, *Vaccine*, 9:631–637 (1991)], using the L variant of the neurovirulent WR strain of vaccinia virus as vector [Panicali et al, *J. Virol.*, 37(3):1000–1010 (1981)] and the gB or pp65 genes (HCMV Towne strain) as inserts cloned into the nonessential BamHI site in the HindIII F region [Panicali and Paoletti, *Proc. Natl. Acad. Sci.*, 79:4927–4931 (1982)] under the control of the vaccinia H6 early/late promoter. Vaccinia recombinant viruses and the parental wild-type WR strain were grown on Vero cells and purified as described [Gonczol et al, cited above].

After plasmid immunization, vaccinia virus recombinants expressing either HCMV-gB or pp65 were used for challenge in the model described in WO 94/23744, published Oct. 27, 1994. Vaccinia virus WR strain replicates in mouse lung after intranasal inoculation and immune protection can be evaluated by virus titrations of the lung. Eight-week old female CBA and BALB/c mice were first pretreated with Bupivicaine, then 1 day later immunized either with pARC-gB or pARC-pp65 (80 µg/mouse). Mice were boosted 8 days later with DNA. Eight days after the second DNA dose mice were i.n. challenged either with 5×10$^6$ pfu of Vaccinia WR-gB or Vaccinia WR-pp65. Lungs were taken at the time of virus challenge (day 0) and at days 1, 3, 4, 5, and 7 after challenge for virus titration. Lungs were homogenized, freeze-thaw 3 times and virus titer determined on Vero cells by plaque titration.

TABLE 5

Virus titers in the lungs of BALB/c mice immunized with pARC-gB or pARC-pp65 and challenged i.n. with Vac-gB

| days after challenge | Vac-aB titer (loa+SD) in lungs* | | |
|---|---|---|---|
| | pARC-gB- immunized | pARC-pp65- immunized | Diff. in titer (log) |
| 0 | 3.29 ± 2.83 | 3.29 ± 2.83 | 0 |
| 1 | 2.24 ± 2.9 | 2.76 ± 2.51 | −0.25 |
| 3 | 4.86 ± 4.61 | 5.60 ± 5.45 | 0.53 |
| 4 | 4.54 ± 4.47 | 5.24 ± 4.9 | 1.13 |
| 5 | 4.33 ± 3.82 | 5.03 ± 4.9 | 1.43 |
| 7 | 2.85 ± 2.84 | 4.17 ± 4.27 | 1.04 |

*Mean of titer (log) ± SD of 3 or 4 mice

TABLE 6

Virus titers in the lungs of BALB/c mice immunized with pARC-gB or pARC-pp65 and challenged i.n. with Vac-pp65

| days after challenge | Vac - pp 65 titer (log ± SD) in lungs* | |
|---|---|---|
| | pARC-gB- immunized | pARC-pp65- immunized |
| 0 | 5.52 ± 4.83 | 5.52 ± 4.83 |
| 1 | 4.31 ± 4.3 | 4.56 ± 3.5 |
| 3 | 7.68 ± 6.75 | 7.15 ± 7.11 |
| 4 | 7.7 ± 7.66 | 6.57 ± 6.56 |
| 5 | 7.45 ± 6.79 | 6.02 ± 6.14 |
| 7 | 7.17 ± 6.17 | 6.23 ± 6.08 |

*Mean of titer (log) ± SD of 3 or 4 mice

This data demonstrate that immunization with either plasmid reduced the titer of the corresponding challenge virus by 0.5–1.4 log on days 3, 4, 5 and 7 after the challenge.

EXAMPLE 12

Secreted Form of gB is More Potent Immunogen Than Membrane-bound gB

To test whether gB bound to the membranes of gB-expressing cells or truncated form of gB lacking the transmembrane region of the molecule (it is secreted from the cell) induce stronger immune responses, mice were immunized with pΔRC-gB (expressing membrane-bound gB) or with pΔRCgB$_{680}$ (expressing the secreted form of gB) and ELISA and neutralizing antibody responses were evaluated as follows.

Plasmids pΔRC-gB (expressing the whole gB) and ΔRC-gB$_{680}$ (expressing N-terminal 680 amino acids of the gB molecule and lacking the transmembrane region) were used in the following immunization protocol. Groups of 10 mice (BALB/c, female, 8 weeks old, purchased from HSD), were inoculated i.m. in the left leg with 50 µg plasmid DNA/mouse/inoculation. Mice were not inoculated with bupivacaine prior to DNA inoculation. Two months later a booster immunization was given (same dose, route).

Sera were tested in the gB-specific ELISA assay described above before the booster inoculation and 1 month after booster. The results are shown in Table 7, which shows the OD values of serum dilutions of 1:40 of individual mice. Preimmune serum samples of 40 mice were included. Cut off value: OD=0.15.

TABLE 7

HCMV ELISA antibodies induced by plasmids expressing membrane-bound or secreted form of gB
OD of sera of mice immunized with

| pΔRC-gB | | | pΔRC-gB$_{680}$ | | |
|---|---|---|---|---|---|
| # of mouse | before booster | after booster | # of mouse | before booster | after booster |
| 1 | 0.31 | 0.55 | 1 | 0.83 | >3.00 |
| 2 | 0.09 | 0.10 | 2 | 0.52 | >3.00 |
| 3 | 0.09 | 0.13 | 3 | 1.65 | >3.00 |
| 4 | 0.06 | 0.08 | 4 | 0.06 | 0.09 |
| 5 | 0.07 | 0.07 | 5 | 1.29 | >3.00 |
| 6 | 0.04 | 0.04 | 6 | 1.92 | >3.00 |
| 7 | 0.08 | 0.17 | 7 | 2.31 | >3.00 |
| 8 | 0.51 | 1.88 | 8 | 1.22 | >3.00 |
| 9 | 0.07 | 0.07 | 9 | 0.62 | >3.00 |
| 10 | 0.06 | 0.06 | 10 | 1.50 | >3.00 |

The results in Table 7 show that ten mice immunized with the pΔRC-gB$_{680}$ were positive for stronger gB-specific antibody responses than mice immunized with pΔRC-gB.

Table 8 provides the results following the immunization protocol above, where the mice had been boosted after 2 months using the same protocol as described for the first immunization. Sera obtained 1 and 2 month after the booster were tested in a HCMV-microneutralization assay. Preimmune sera were included as negative controls, NA titers≧12 are considered positive.

TABLE 8 pΔRC-gB$_{680}$ expressing secreted form of gB induce stronger neutralizing antibody responses than pΔRC-gB expressing membrane-bound gB
NA titers of sera of mice 1 and 2 month after booster immunized with

| pΔRC-gB | | pΔRC-gB680 | |
|---|---|---|---|
| 1M | 2M | 1M | 2M |
| 16 | 24 | 128 | 64 |
| 8 | <8 | 64 | 32 |
| 4 | <4 | 256 | 192 |
| 4 | 8 | <4 | 12 |
| 8 | 4 | 128 | 96 |
| 4 | 4 | 64 | 64 |
| 8 | 24 | 64 | 32 |
| 48 | 48 | 48 | ND |
| 6 | 4 | 96 | 96 |
| <6 | 4 | 16 | 24 |

As shown in Table 8, nine of the pΔRC-gB$_{680}$-immunized mice developed gB-specific antibodies, but only 3 of 10 responded in the pΔRC-gB-immunized group. HCMV-neutralizing antibody titers were also higher in the pΔRC-gB$_{680}$-immunized mice, 9 of 10 developed significant NA responses versus 3 of 10 in the pΔRC-gB-immunized group (Table 8).

These data show that the pΔRC-gB$_{680}$ plasmid expressing the N-terminal 680 amino acids of gB (lacking the transmembrane region of the protein) given intramuscularly induces more potent antibody responses to gB than the pΔRC-gB plasmid expressing the full gB.

EXAMPLE 13 pΔRC-gB$_{680}$ Mixed with pΔRC-pp65 and Given At One Site or Inoculated Separately Induce Both gB- and pp65-Specific Antibodies As shown above, pTet-gB and pΔRC-pp65 plasmids mixed and inoculated at one site induced immune responses to both gB and pp65 indicating that there is no antigenic competition between gB and pp65. In this experiment whether the pΔRC-gB$_{680}$ (expressing the secreted form of gB) is suitable for immunization in a mixture with pΔRC-pp65 was tested.

Groups of 10 BALB/c mice (female, HSD, 9–10 weeks old) were inoculated either with a mixture of two plasmids containing 50 µg of each in 200 µl: 100 µl (50 µg) into the left leg, 100 µl (50 µg) into the right leg; or the two different plasmids were inoculated separately: one kind of DNA (100 µl/50 µg) into the left leg, the other kind of plasmid (100 µl/50 µg) into the right leg. A booster immunization was given 1 month later. The plasmids used in this study were pΔRC-pp65, pΔRC-gB, and pΔRC-gB$_{680}$. Table 9 shows results obtained with sera taken 8 days after booster. The ELISA antigen was purified gB. Cut off value: 0.081.

The results show that mice immunized with mixtures of pΔRC-gB and pΔRC-pp65 developed both gB and pp65 ELISA antibodies. Similar responses were observed in mice immunized with the two plasmids given at separate sites (Table 10 below). HCMV-gB-specific antibody, responses in mice immunized with pΔRC-gB$_{680}$ either given in mixture with pΔRC-pp65 or at separate sites were stronger than in mice immunized with the full-gB-expressing pΔRC-gB (these results confirm that the secreted form of gB is a stronger immunogen than the membrane-bound form).

TABLE 9 pΔRC-gB$_{680}$ mixed with pΔRC-pp65 and given at one site or inoculated separately induce gB-specific antibodies
gB-specific antibody (OD at serum dilutions of 1:40)

| | mice inoculated with pΔRC-gB and pΔRC-pp65 | | | mice inoculated with PΔRC-gB$_{680}$ and pΔRC-pp65 | | |
|---|---|---|---|---|---|---|
| mouse | at one site | mouse | at two sites | mouse | at one site | mouse | at two sites |
| #326 | 0.085 | #356 | 0.115 | #341 | 1.280 | #336 | 1.058 |
| #327 | 0.193 | #357 | 0.082 | #342 | 1.070 | #337 | 0.550 |
| #328 | 0.121 | #358 | 0.099 | #343 | 1.385 | #338 | 0.193 |
| #329 | 0.060 | #359 | 0.107 | #344 | 1.190 | #339 | 1.039 |
| #330 | 0.115 | #360 | 0.107 | #345 | 2.588 | #340 | 0.207 |
| #331 | 0.093 | #361 | NT | #351 | 1.037 | #346 | 0.288 |
| #332 | 0.061 | #362 | 0.092 | #352 | 0.771 | #347 | 0.220 |
| #333 | 0.089 | #363 | 0.065 | #353 | 0.493 | #348 | 0.513 |
| #334 | 0.078 | #364 | 0.152 | #354 | 0.560 | #349 | 0.223 |
| #335 | 0.088 | #365 | 0.082 | #355 | 0.933 | #350 | 0.719 |
| Mean OD: | 0.098 | | 0.100 | | 1.130 | | 0.521 |

Mice immunized as above with the mixture, of pΔRC-gB$_{680}$ and pΔRC-pp65 showed gB-specific antibody responses similar to those observed in mice immunized with the two kinds of plasmids given at separate sites. Results of pp$^{65}$-specific antibody responses showed that mice responded to the pp65 antigen regardless of immunization with a mixture or with plasmids given at separate sites (Table 10). Table 10 shows results obtained with sera taken 8 days after booster (cut off value: 0.050).

TABLE 10 pΔRC-gB$_{680}$ mixed with pΔRC-pp65 and given at one site or inoculated separately induce pp65-specific antibodies
pp65-specific antibody (OD at serum dilutions of 1:40)

| | mice inoculated with pΔRC-gB and pΔRC-PP65 | | | mice inoculated with pΔRC-gB$_{680}$ and pΔRC-pp65 | | |
|---|---|---|---|---|---|---|
| mouse | at one site | mouse | at two sites | mouse | at one site | mouse | at two sites |
| #326 | 0.037 | #356 | 0.000 | #341 | 0.389 | #336 | 0.276 |
| #327 | 0.149 | #357 | 0.000 | #342 | 0.238 | #337 | 0.295 |
| #328 | 0.002 | #358 | 0.508 | #343 | 0.440 | #338 | 0.000 |
| #329 | 0.000 | #359 | 0.008 | #344 | 0.077 | #339 | 0.009 |
| #330 | 0.009 | #360 | 0.176 | #345 | 0.008 | #340 | 0.030 |
| #331 | 0.007 | #361 | dead | #351 | 0.081 | #346 | 0.051 |
| #332 | 0.014 | #362 | 0.009 | #352 | 0.077 | #347 | 0.124 |
| #333 | 0.000 | #363 | 0.028 | #353 | 0.049 | #348 | 0.281 |
| #334 | 0.000 | #364 | 0.097 | #354 | 0.016 | #349 | 0.118 |
| #335 | 0.008 | #365 | 0.201 | #355 | 0.178 | #350 | 0.014 |
| Mean OD: | 0.014 | | 0.109 | | 0.154 | | 0.111 |

The data show that mice develop significant immune responses both to gB and pp65 after immunization with a mixture of pΔRC-gB$_{680}$ and pΔRC-pp65, indicating that these two HCMV antigens are able to induce parallel immune responses when introduced by expression plasmids to the immune system.

EXAMPLE 14

Immunization Studies in Mice Immunized with HCMV Plasmid Vectors Expressing Full-Length and Transmembrane-Deleted gB As shown in the studies described above, full-length gB and transmembrane-deleted gB have been found to induce a strong and long-term antibody response when delivered by plasmid DNA. The following experiments provide further evidence of this effect.

A. pCBgB and pCB-gBΔtm

Figure 7A:
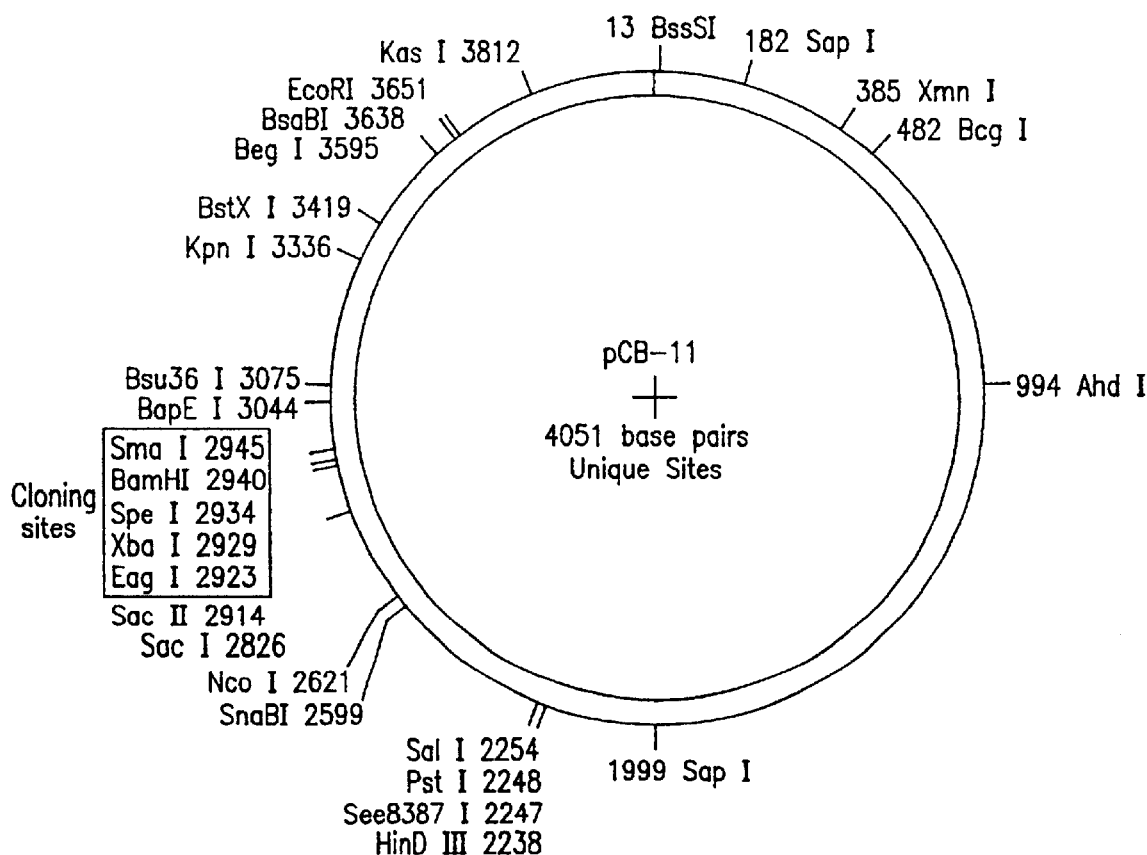
FIG. 7A provides a circular map of the eukaryotic expression vector pCB11.
Figure 7B:
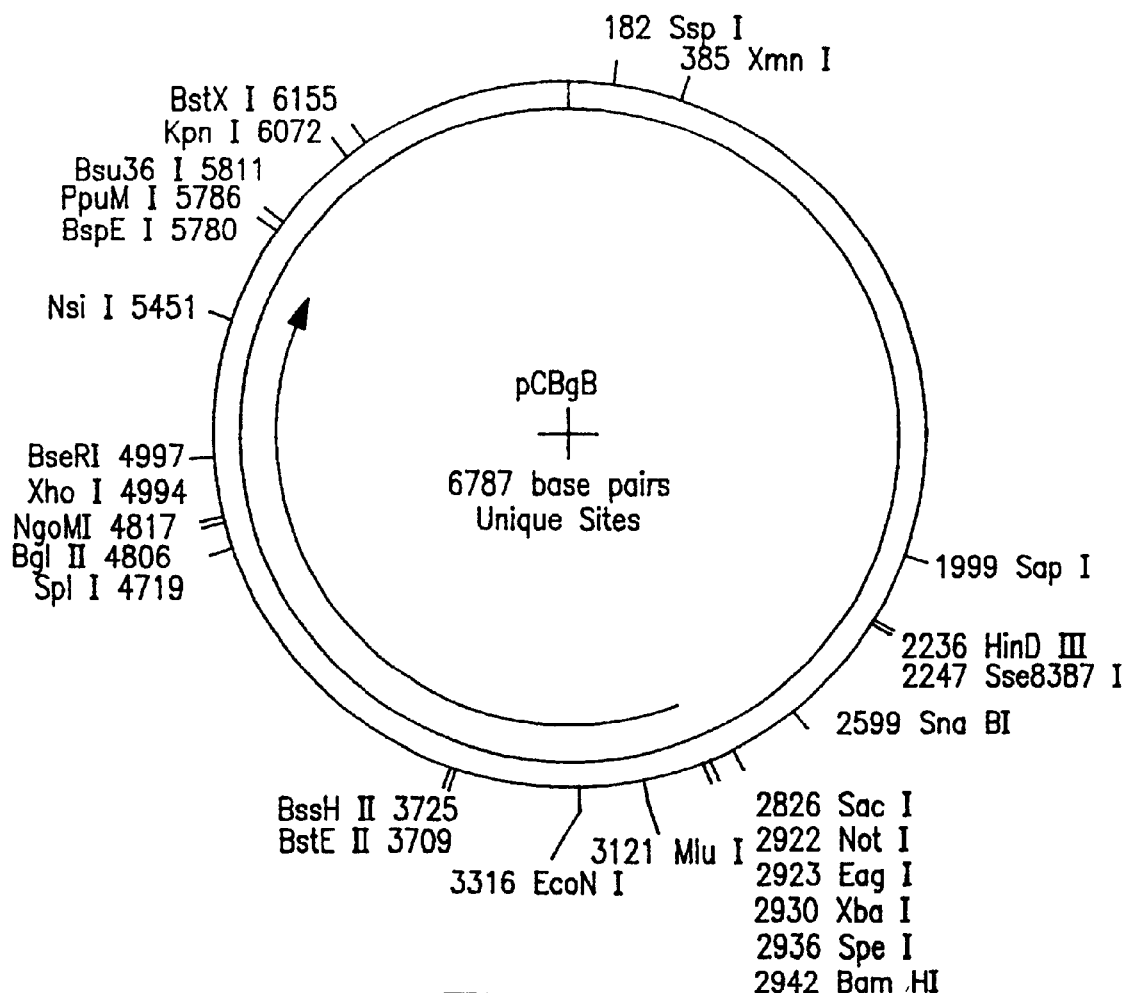
FIG. 7B provides a circular map of pCBgB.
Figure 7C:
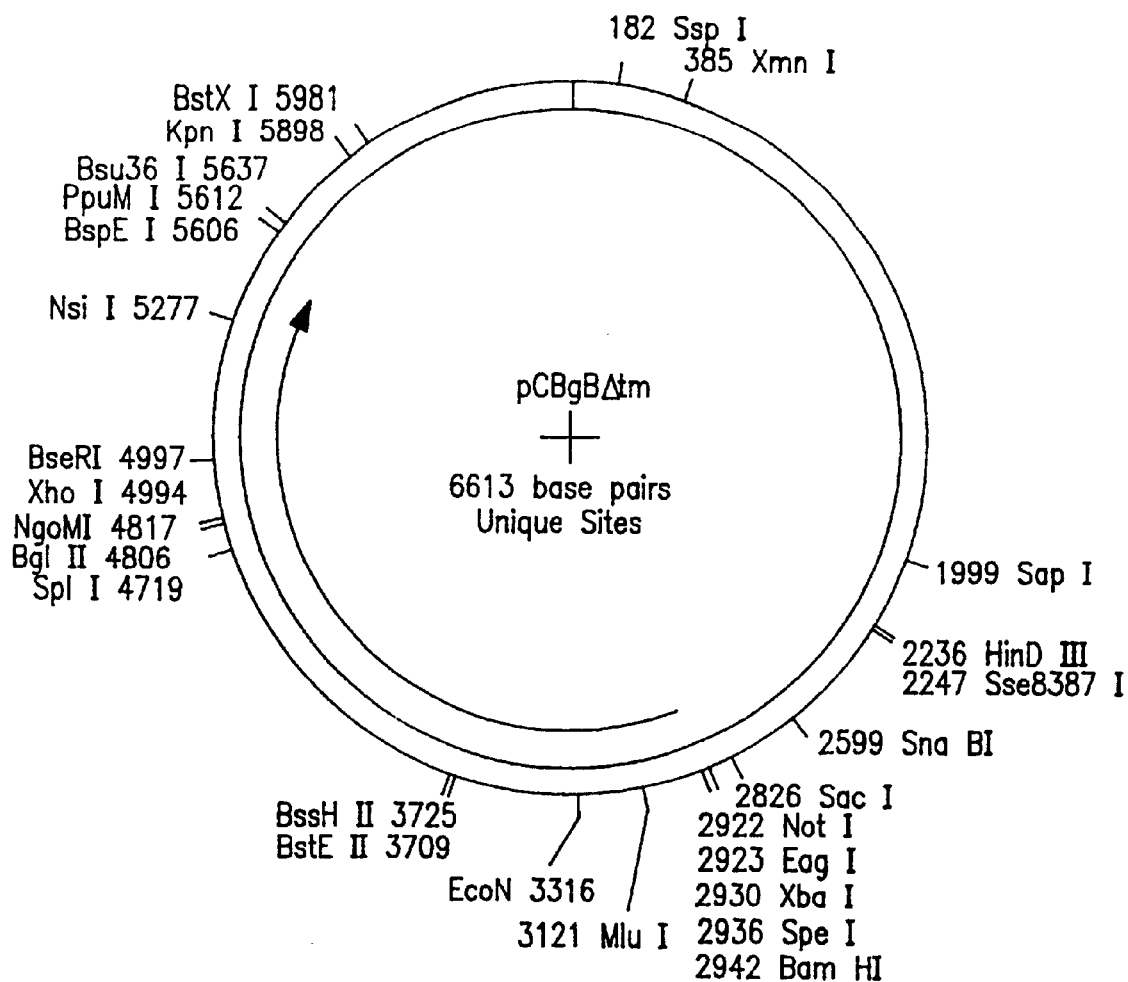
FIG. 7C provides a circular map of pCBgBΔtm.
Figure 8:
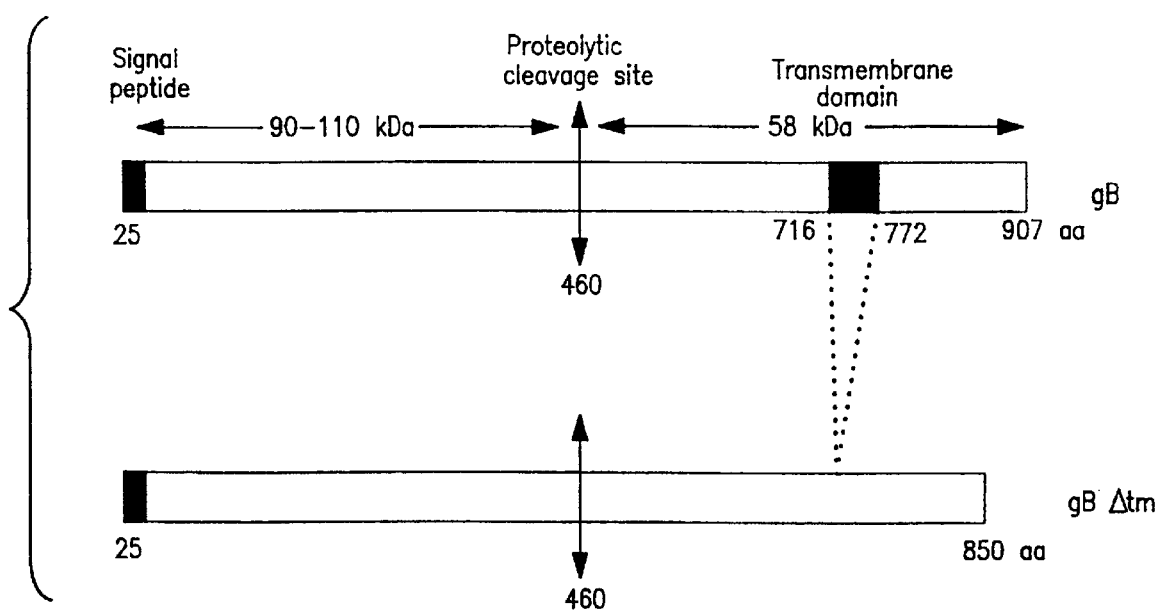
FIG. 8 provides a schematic representation of the gB protein (top line) and of its homolog which is deleted of the transmembrane domain (bottom line).

The gB open reading frame (ORF, nucleotides 1–2724) was obtained from the CMV Towne strain [SEQ ID NO: 1] using conventional techniques. The gBΔtm (transmembrane-deleted gB) was obtained from the wild type gene by deleting in frame the sequences coding for the hydrophobic transmembrane domain of the protein [nucleotides 2143–2316 were deleted from the gB ORF, SEQ ID NO:1]. These two coding sequences were introduced into the polylinker of the eukaryotic expression vector pCB11 corresponding to a commercially available pUC backbone with the HCMV IE1 promoter/enhancer sequences and the terminator sequences from the bovine growth hormone gene (FIG. 7A). The resulting plasmids, pCBgB and pCBgBΔtm expressing the full-length gB and its truncated version, respectively, are shown in FIG. 8. Protein expression from pCBgB and from pCBgBΔtm was confirmed by immunofluorescence and immunoprecipitation after transfection into cultured CHO-K1 cells. The immunoprecipitation experiment indicated that only pCBgBΔtm gave rise to a secreted form of gB which could be recovered from the cell culture medium.

B. Immunization

The study described below was performed with pCBgB and pCBgBΔtm in 6–8 week old female BALB/c mice. Anesthetized (xylazine+ketamine) mice (8 per group) received three administrations of 50 μg pCBgB or pCBgBΔtm at three week intervals (days 0, 21 and 42) either intramuscularly (IM) or intradermally (ID). For IM administration, DNA in 50 μl of saline was injected into the quadriceps with a Hamilton syringe equipped with a 20 gauge needle. For ID administration, DNA in a total volume of 100 μl of saline was injected into 5 sites of shaved dorsal skin with a pneumatic jet injector.

In each group, mice were labeled and bled on days 14 (following 1 injection), 35 (following 2 injections), 56 (following 3 injections), 116 and 202. The anti-urease IgG antibody response was followed by ELISA against recombinant gB produced in MRC5 cells infected with ALVAC-gB. The sera collected on days 116 and 202 were analyzed for HCMV neutralization in complement dependent microneutralization assay [Gonczol et al, cited above (1986)]. The data is provided in Table 11 and summarized in FIG. 9.

TABLE 11

INDIVIDUAL ELISA TITERS
IN MICE IMMUNIZED WITH HCMV GB PLASMID VECTORS

| | | Intramuscular | | Intradermal | | neg. |
|---|---|---|---|---|---|---|
| Day | # Mouse | pCBgB ELISA | pCBqBΔtm ELISA | pCBgB ELISA | pCBgBΔtm ELISA | serum ELISA |
| 14 | 1 | 50 | 50 | <50 | <50 | <50 |
| | 2 | <50 | 200 | <50 | <50 | <50 |
| | 3 | 100 | 9600 | 100 | <50 | |
| | 4 | <50 | 300 | <50 | <50 | |
| | 5 | 100 | 100 | <50 | <50 | |
| | 6 | <50 | 75 | <50 | 50 | |
| | 7 | 100 | 75 | <50 | <50 | |
| | 8 | 50 | <50 | <50 | <50 | |
| 35 | 1 | 100 | 100 | 75 | 50 | <50 |
| | 2 | 150 | 900 | 150 | 600 | <50 |
| | 3 | 200 | 12800 | 6400 | 2400 | |
| | 4 | 150 | 3200 | 1600 | 200 | |

TABLE 11-continued

INDIVIDUAL ELISA TITERS
IN MICE IMMUNIZED WITH HCMV GB PLASMID VECTORS

| Day | # Mouse | Intramuscular | | Intradermal | | neg. serum ELISA |
|---|---|---|---|---|---|---|
| | | pCBgB ELISA | pCBgBΔtm ELISA | pCBgB ELISA | pCBgBΔtm ELISA | |
| | 5 | 400 | 1200 | 100 | 1600 | |
| | 6 | 100 | 1200 | 1200 | 6400 | |
| | 7 | 150 | 300 | 75 | 100 | |
| | 8 | 150 | 100 | 200 | 150 | |
| 56 | 1 | 150 | 1600 | 200 | 1200 | <50 |
| | 2 | 200 | 2400 | 200 | 38400 | <50 |
| | 3 | 200 | 38400 | 6400 | 12800 | |
| | 4 | 75 | 61200 | 6400 | 12800 | |
| | 5 | 400 | 2400 | 1200 | 4800 | |
| | 6 | 100 | 38400 | 3200 | 9600 | |
| | 7 | 200 | 19200 | 600 | 1600 | |
| | 8 | 600 | 4800 | 1200 | 4800 | |
| 116 | 1 | <50 | 1200 | 75 | 600 | <50 |
| | 2 | 1600 | 800 | 37.5 | 12800 | <50 |
| | 3 | 400 | 9600 | 1200 | 640 | |
| | 4 | <50 | 25600 | 2400 | 4800 | |
| | 5 | 25 | 1600 | 150 | 800 | |
| | 6 | <50 | 25600 | 1600 | 4800 | |
| | 7 | <50 | 6400 | 300 | 800 | |
| | 8 | 200 | 1200 | 200 | 800 | |
| 202 | 1 | <50 | 1000 | 50 | 250 | <50 |
| | 2 | 400 | 1000 | 25 | 8000 | <50 |
| | 3 | 1600 | 8000 | 800 | 3000 | |
| | 4 | <50 | 64000 | 1600 | 1500 | |
| | 5 | 25 | 1500 | 50 | 500 | |
| | 6 | <50 | 24000 | 1200 | 3000 | |
| | 7 | <50 | 4000 | 200 | 375 | |
| | 8 | | 1000 | 150 | 375 | |

Figure 9:
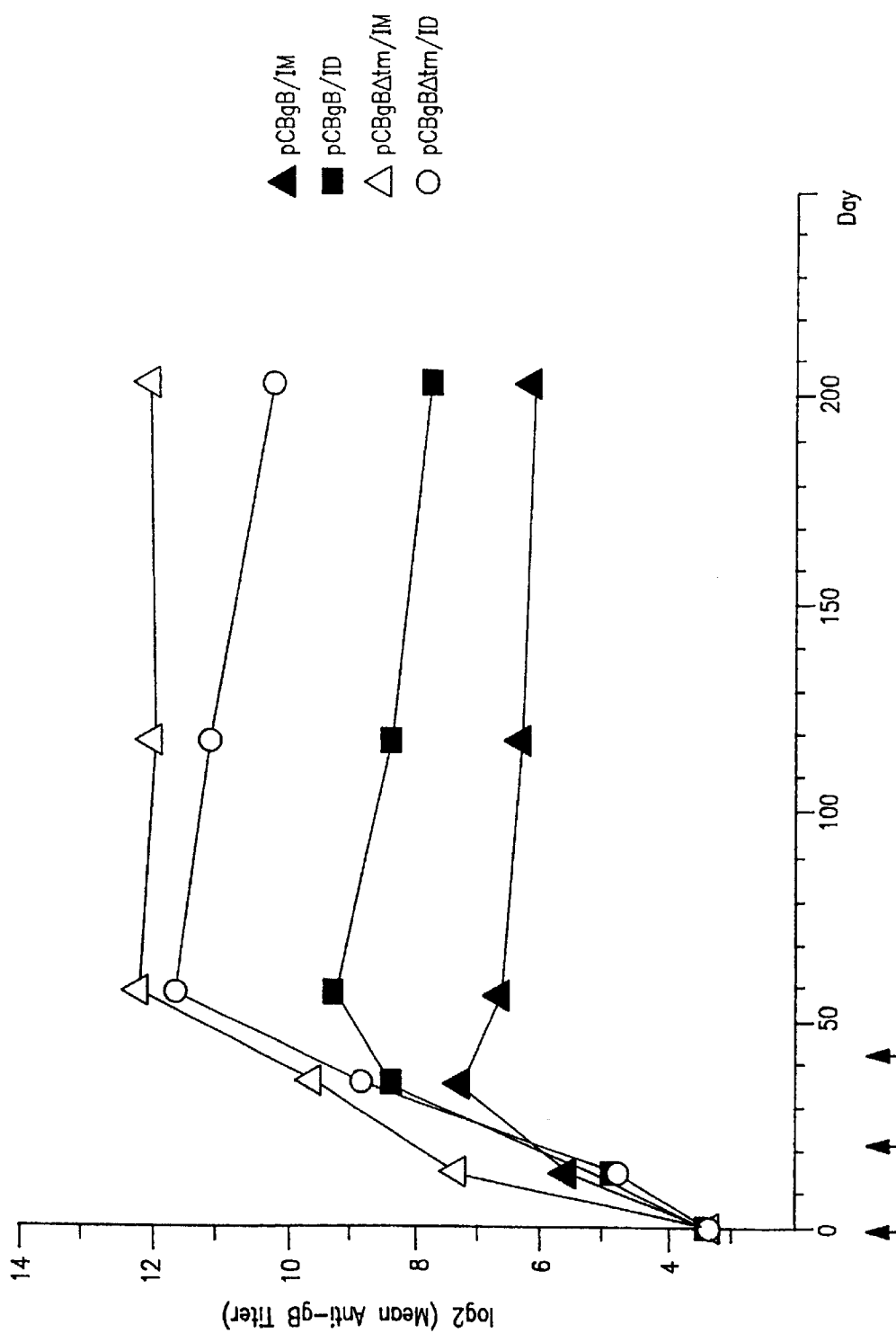
FIG. 9 is a graph illustrating the anti-gB titers in sera of BALB/c mice immunized with plasmids pCBgB and pCBgBΔtm intramuscularly (IM) and intradermally (ID).

As illustrated in Table 11 above and in FIG. 9, pCBgB and pCBgBΔtm plasmids induced serum IgGs against recombinant gB protein after IM or ID administration in BALB/c mice [pCBgBΔtm/ID≧pCBgBΔtm/IM>>pCBgB/ID≧pCBgB/IM]. pCBgB and pCBgBΔtm plasmids induced detectable neutralizing antibodies to hCMV (in vitro assay) after IM or ID administration in BALB/c mice [pCBgBΔtm>pCBgB].

pCB-gB and pCB-gBΔtm have been observed to induce a strong and long-term antibody response. pCBgB and especially pCB-gBΔtm induce neutralizing antibodies.

The nature of the response ($IgG_1/IgG_{2a}$) differs between pCB-gB and pCB-gBΔtm. Particularly, pCB-gB has been observed to induce an $IgG_1$ ($T_{H2}$) response which is approximately equivalent to the $IgG_{2a}$ ($T_{H1}$) response induced. In contrast, pCB-gBΔtm has been observed to induce an $IgG_1$ response that is significantly stronger that the $IgG_{2a}$ response induced.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A pΔRC-pp65 plasmid, said plasmid comprising the human cytomegalovirus (HCMV) gene encoding the HCMV pp65 tegument protein under the control of regulatory sequences which direct expression of the pp65 antigen in mammalian cells.

2. A composition comprising a carrier and a DNA molecule pΔRC-pp65.

3. The composition according to claim 2, wherein the carrier is selected from the group consisting of saline and isotonic water.

* * * * *

UNITED STATES PATENT AND TRADEMARK OFFICE
CERTIFICATE OF CORRECTION

PATENT NO. : 6,448,389 B1
DATED : September 10, 2002
INVENTOR(S) : E. Gonczol et al.

It is certified that error appears in the above-identified patent and that said Letters Patent is hereby corrected as shown below:

Column 11,
Line 23, replace "nice" with -- mice --.

Column 13,
Line 18, replace "nice" with -- mice --.

Column 14,
Line 32, replace "Vac-aB titer (1oa+SD)" with -- Vac-gB titer (1og + SD) --.

Column 16,
Line 33, replace "Mixed" with -- mixed --.

Signed and Sealed this

Twenty-fifth Day of February, 2003

JAMES E. ROGAN
*Director of the United States Patent and Trademark Office*